(12) United States Patent
Zhang et al.

(10) Patent No.: US 6,972,013 B1
(45) Date of Patent: Dec. 6, 2005

(54) ENHANCED DELIVERY OF NAKED DNA TO SKIN BY NON-INVASIVE IN VIVO ELECTROPORATION

(75) Inventors: Lei Zhang, San Diego, CA (US); Dietmar P. Rabussay, Solana Beach, CA (US)

(73) Assignee: Genetronics, Inc., San Diego, CA (US)

( * ) Notice: Subject to any disclaimer, the term of this patent is extended or adjusted under 35 U.S.C. 154(b) by 560 days.

(21) Appl. No.: 10/233,007

(22) Filed: Aug. 30, 2002

Related U.S. Application Data

(63) Continuation-in-part of application No. 10/165,657, filed on Jun. 7, 2002, now Pat. No. 6,678,556, which is a continuation-in-part of application No. 09/625,825, filed on Jul. 26, 2000, now Pat. No. 6,654,636, and a continuation-in-part of application No. 09/352,809, filed on Jul. 13, 1999, now Pat. No. 6,697,669.

(60) Provisional application No. 60/397,313, filed on Jul. 19, 2002, provisional application No. 60/126,058, filed on Mar. 25, 1999, provisional application No. 60/109,324, filed on Nov. 20, 1998, provisional application No. 60/092,544, filed on Jul. 13, 1998.

(51) Int. Cl.$^7$ ............................................. A61N 1/30
(52) U.S. Cl. ......................................... 604/501; 604/20
(58) Field of Search .............................. 604/19–21, 49, 604/313–316, 501; 606/41, 42, 44, 48–50; 607/115, 120

(56) References Cited

U.S. PATENT DOCUMENTS

| | | | |
|---|---|---|---|
| 6,520,950 B1 * | 2/2003 | Hofmann et al. | 604/503 |
| 6,654,636 B1 * | 11/2003 | Dev et al. | 604/21 |
| 6,678,556 B1 * | 1/2004 | Nolan et al. | 604/21 |
| 6,697,669 B2 * | 2/2004 | Dev et al. | 604/21 |
| 2002/0099323 A1 * | 7/2002 | Dev et al. | 604/21 |
| 2004/0147964 A1 * | 7/2004 | Nolan et al. | 607/3 |
| 2005/0054594 A1 * | 3/2005 | Zhang et al. | 514/44 |

* cited by examiner

Primary Examiner—Sharon Kennedy
(74) Attorney, Agent, or Firm—Daniel M. Chambers; Douglas C. Murdock; Bio Technology Law Group

(57) ABSTRACT

In vivo methods are provided for using an electric field to delivery therapeutic or immunizing treatment to a subject by applying non-invasive, user-friendly electrodes to the surface of the skin. Thus, therapeutic or immunizing agents can be delivered into cells of skin for local and systemic treatments or for immunization with optimal gene expression and minimal tissue damage. In particular, therapeutic agents include naked or formulated nucleic acid, polypeptides and chemotherapeutic agents.

24 Claims, 34 Drawing Sheets

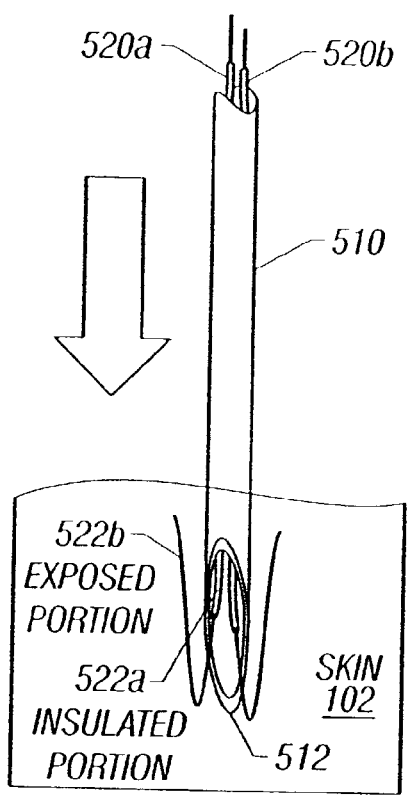
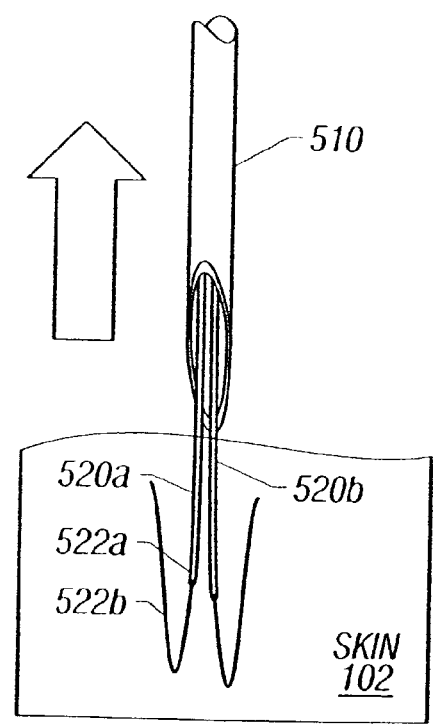
FIG. 5A
FIG. 5B

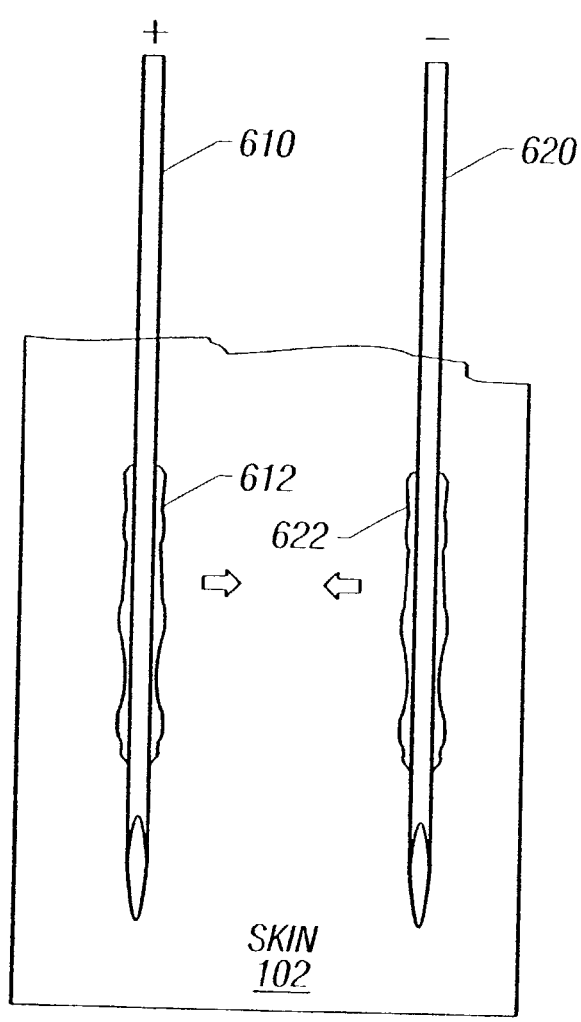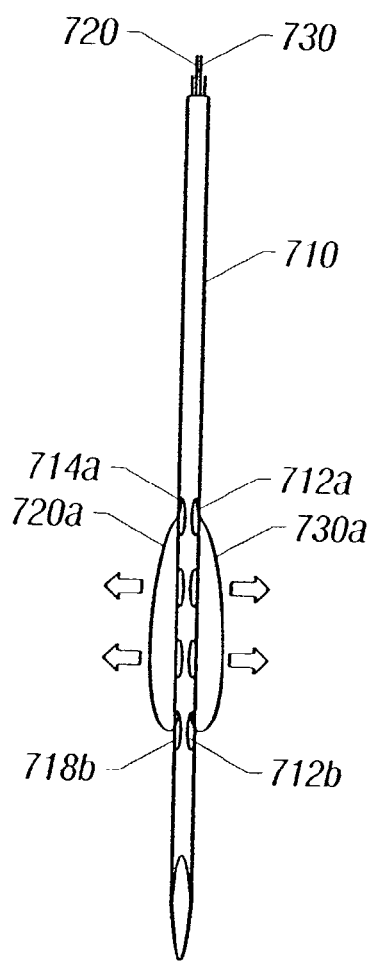
FIG. 6
FIG. 7

ELECTRODES

PARRALLEL ELECTRODES

FIG. 13A Pressure only
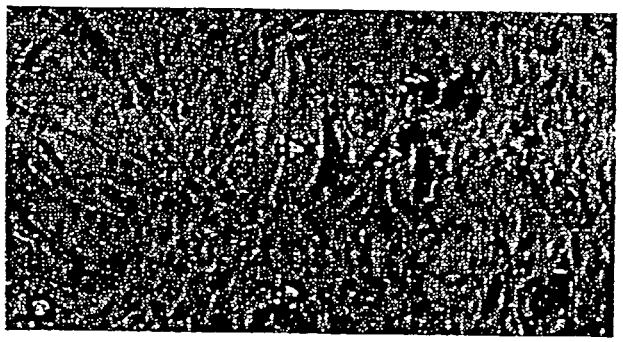
FIG. 13B EP (10 ms) + 1 min
FIG. 13C EP (10 ms) + 10 min
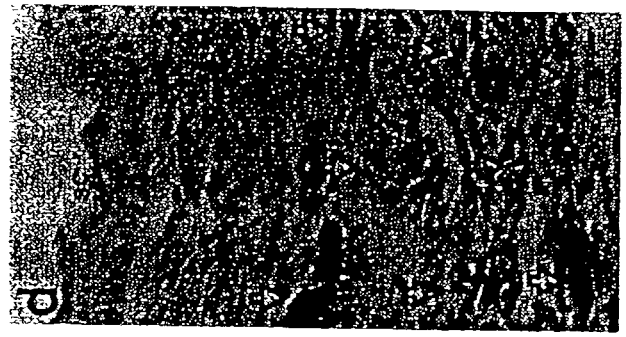
FIG. 13D EP (20 ms) + 10 min

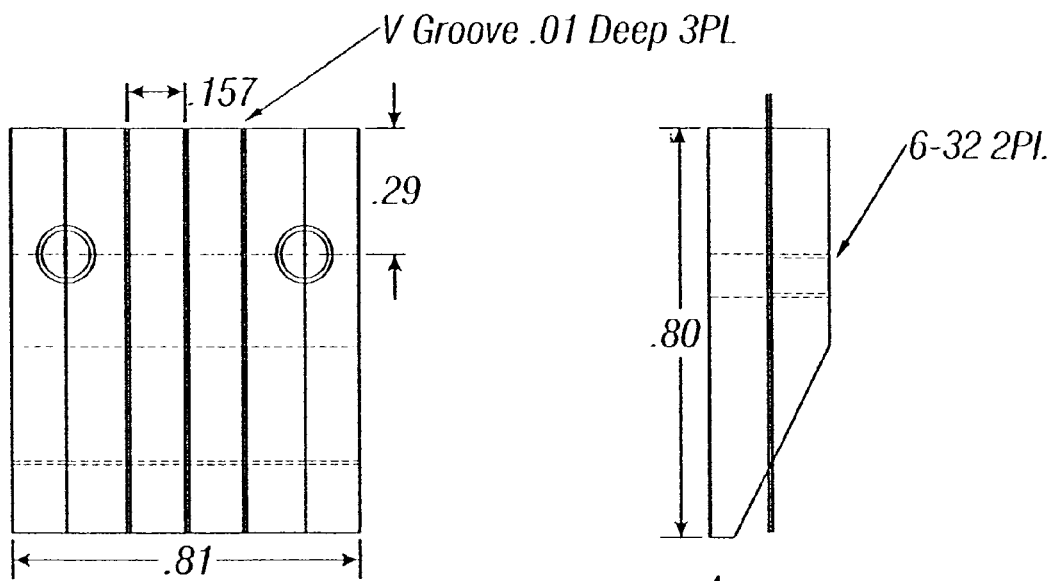
FIG. 20A
FIG. 20B
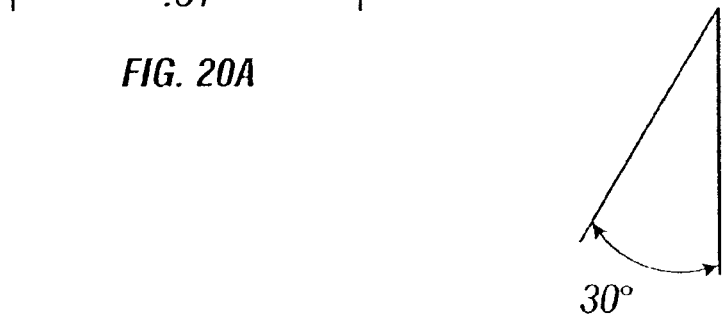
FIG. 20C
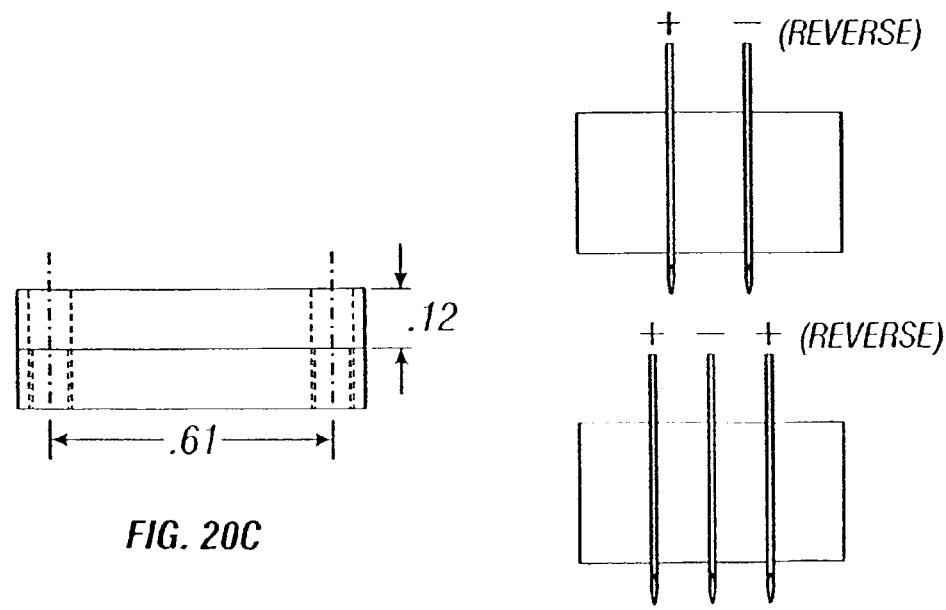
FIG. 20D

Electroporation-enhanced delivery of secreted plsmid DNA (1 mg via 4 injections) in porcine muscle(200V, 60ms, 6-stainless steel needle array electrode, n=4)

Electroporation-enhanced delivery of luciferase plasmid in porcine muscle at two time points (100V, 60ms, 2 pulses, 4-gold needle array electrode, n=6)

Change of inflammatory score in porcine muscle histology over time after delivery of luciferase plasmid DNA using different pulsing conditions (4-gold needle array electrode, n=9)

Effect of Pulse Conditions on Long Term Histological Changes in Porcine Muscle

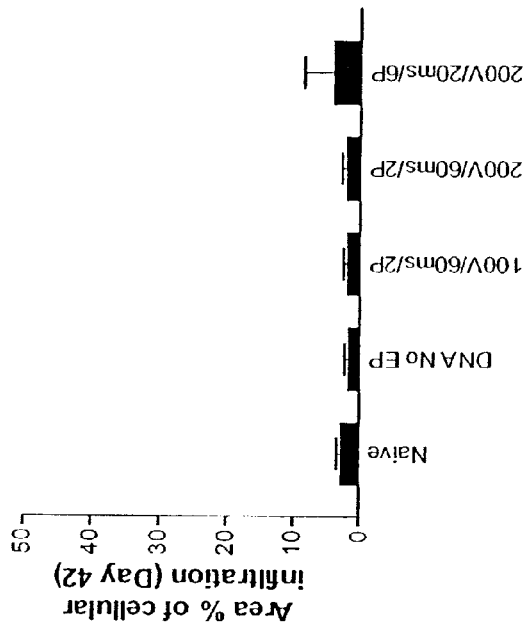

FIGURE 32A

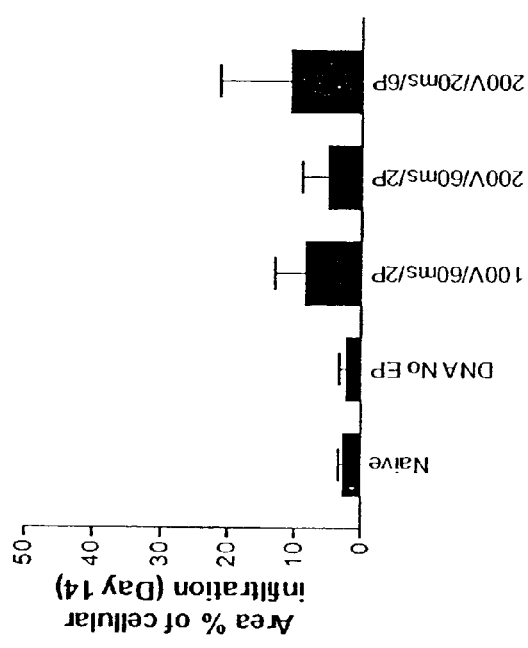

FIGURE 32B

Male or female outbread pigs, age four to six weeks; 600 ug DNA in 500 ul PBS were administered to hind limb quadriceps muscle; Electroporation was as described above; after punch biopsy, H&E stained tissue samples (n=6) were analyzed (blinded) using computer imaging software to calculate the % area of blue stained mononuclear infiltrating cells in a standard 2.5 mm² square
(S.Babiuk, L.Babiuk, VIDO, Saskatoon, SK, Ca; G.W., D.P.R.)

FIGURE 32

ENHANCED DELIVERY OF NAKED DNA TO SKIN BY NON-INVASIVE IN VIVO ELECTROPORATION

RELATED APPLICATIONS

This application relies for priority under 35 U.S.C. 119(e) on U.S. provisional application Ser. No. 60/397,313, filed Jul. 19, 2002 and is a Continuation-in-Part Application of U.S. application Ser. No. 10/165,657, filed Jun. 7, 2002, which is a Continuation-in-Part Application of Ser. No. 09/625,825, filed Jul. 26, 2000, and U.S. application Ser. No. 09/352,809, filed Jul. 13, 1999, which relies for priority under 35 U.S.C. §119(e)(1) on Provisional Application Ser. No. 60/126,058, filed Mar. 25, 1999, Provisional Application Ser. No. 60/092,544, filed Jul. 13, 1998, and Provisional Application Ser. No. Ser. No. 60/109,324, filed Nov. 20, 1998.

FIELD OF THE INVENTION

The invention relates generally to the use of electric pulses to increase the permeability of cells, and more specifically to a method and apparatus for the application of controlled electric fields for in vivo delivery of pharmaceutical compounds and genes into cells by electroporation therapy (EPT), also known as cell poration therapy (CPT) electrogene therapy (EGT) and electrochemotherapy (ECT).

BACKGROUND OF THE INVENTION

The skin is an especially attractive target for gene therapy. In particular, the ability to target genes to the epidermis of the skin could be used to correct skin-specific disorders as well as for the production of proteins secreted into the skin to correct certain systemic diseases. For example, genes expressing cytokines, interferons or other biologically active molecules could be used to treat skin tumors or other lesions. In addition, keratinocytes and fibroblasts or stem cells in the skin can secrete protein factors which circulate to treat systemic conditions such as hemophilia A or B. Despite the clear potential in using skin as a target for gene therapy, the major technical problem of an in vivo method of gene delivery remains largely unresolved. Since the stratum corneum (SC) acts as a significant physical barrier to gene transfer into the skin, the technical problem of how to deliver genes through this layer persists.

Similarly, muscle cells are also useful targets for gene therapy due to their ubiquity. Nonetheless, as with skin, there exists a need for a method to reliably introduce exogenous therapeutic material into muscle cells.

Gene therapy does not include only intrinsically therapeutic genetic material (i.e., genes that encode a missing or underexpressed gene product), but also genetic material which elicits an immune response when the gene product is recognized by the immune system. One of the oldest and most effective forms of preventative care against infectious diseases is vaccination. Safe and effective vaccines are available to protect against a variety of bacterial and viral diseases. These vaccines consist of inactivated pathogens, recombinant or natural subunits, and live attenuated or live recombinant microorganisms.

DNA immunization, a novel method to induce protective immune responses, was recently introduced into the scientific community and proven to be very effective in animal models. This technology is currently in safety and efficacy trials in human volunteers. DNA immunization entails the direct, in vivo administration of plasmid-based DNA vectors that encode the production of defined microbial antigens. The de novo production of these antigens in the host's own cells results in the elicitation of antibody (i.e., humoral) and cellular immune responses that provide protection against live virus challenge and persist for extended periods in the absence of further immunizations. The unique advantage of this technology is its ability to mimic the effects of live attenuated vaccines without the safety and stability concerns associated with the parenteral administration of live infectious agents. Because of these advantages, considerable research efforts have focused on refining in vivo delivery systems for naked DNA that result in maximal antigen production and resultant immune responses.

The most widely used administration of vaccine DNA is direct injection of the DNA into muscle or skin by needle and syringe. This method is effective in inducing immune responses in small animals, such as mice, but even here it requires the administration of relatively large amounts of DNA, ca. 50 to 100 ug per mouse. To obtain immune responses in larger animals, such as rabbits, non-human primates, and humans, very large amounts of DNA have to be injected. It has to be seen whether this requirement for very large amounts of vaccine DNA turns out to be practical, for safety and commercial reasons, in human applications. A need exists for methods of vaccine DNA delivery that require less DNA and are more efficacious than commonly used methods.

A cell has a natural resistance to the passage of molecules through its membranes into the cell cytoplasm. Scientists in the 1970's first discovered "electroporation", where electrical fields are used to create pores in cells without causing permanent damage to the cells. Electroporation made possible the insertion of large molecules directly into the cell cytoplasm by temporarily creating pores in the cells which allow the molecules to pass into the cell.

Electroporation techniques (both in vitro and in vivo) function by applying a brief high voltage pulse to electrodes positioned around the treatment region. The electric field generated between the electrodes causes the cell membranes to temporarily become porous, whereupon molecules of the implant agent enter the cells.

Electroporation has been used to implant materials into liposomes and many different types of cells. Such cells, for example, include eggs, platelets, human cells, red blood cells, mammalian cells, plant protoplasts, plant pollen, bacteria, fungi, yeast, and sperm. Furthermore, electroporation has been used to deliver a variety of different materials, including nucleic acids, polypeptides, and various chemical agents into cells.

Electroporation has been used in both in vitro and in vivo procedures to introduce foreign material into living cells. With in vitro applications, a sample of live cells is first mixed with the implant agent and placed between electrodes such as parallel plates. Then, the electrodes are energized to apply an electrical field to the cell/implant mixture, which causes the cells to become transiently permeable, and the implant agent enters the cell. With in vivo applications of electroporation, electrodes are provided in various configurations such as, for example, a non-invasive caliper electrode that grips a fold of tissue whose cells are to be treated or a similarly non-invasive meander electrode that is placed on the surface of skin or of an organ. Electric charge is applied to such non-invasive electrodes and an electric field is generated in the underlying tissue. Alternatively, needle-shaped electrodes may be inserted into the patient (i.e., invasive electrodes), to access more deeply located cells. In either case, after the therapeutic agent is introduced into the treatment region, by injection or otherwise, e.g., jet injection, puncture mediated transfer, ballistic particle bombardment, the electrodes when energized apply an electrical field to the region. In some electroporation applications, this electric field comprises a single square wave pulse on the order of 100 to 500 V/cm, of about 10 to 60 ms duration. Such a pulse may be generated, for example, in known applications of the Electro Square Porator T820 or ECM830, made by the BTX Division of Genetronics, Inc.

Electroporation has been recently suggested as an alternate approach to aid in the treatment of certain diseases such as cancer by introducing a chemotherapy drug directly into the cell. For example, in the treatment of certain types of cancer with chemotherapy it is necessary to use a high enough dose of a drug to kill the cancer cells without killing an unacceptably high number of normal cells. If the chemotherapy drug could be inserted directly inside the cancer cells, this objective could be achieved. Some of the best anti-cancer drugs, for example, standard formulation bleomycin, normally cannot penetrate the membranes of certain cancer cells effectively. However, electroporation makes it possible to insert the bleomycin into the cells.

Despite the suitability of the skin as a target tissue for gene therapy, there are significant barriers to safe, easy, efficient, and economical gene delivery. In particular, the lipid-rich stratum corneum ("SC"), which is composed of dead keratinocytes surrounded by multiple, parallel bilayer membranes, represents a formidable physical barrier to gene transfer into or through skin. To overcome this barrier a novel, non-viral approach, involving the basic concept of electroporation to introduce genes into the epidermis is provided by the invention.

As described above, the technique of electroporation is now a well-established physical method that allows introduction of marker molecules, drugs, genes, antisense oligonucleotides and proteins intracellularly. However, there still exists a need for improved methods to introduce therapeutic agents directly into skin cells or through the skin and into muscle cells.

BRIEF DESCRIPTION OF THE INVENTION

The invention describes an in vivo method, using a pulsed electric field to deliver therapeutic agents into cells of the skin.

In one embodiment the invention provides in vivo methods for enhancing expression of a therapeutic polypeptide encoded by an isolated polynucleotide to be delivered into skin cells in vivo in a subject, said method comprising:
 a) introducing about 0.05 µg to about 100 µg per skin tissue site of at least one isolated polynucleotide encoding a therapeutic polypeptide into one or more skin tissue sites of a subject;
 b) applying at least two non-invasive electrodes to the skin tissue site;
 c) generating a total charge transfer at the skin tissue site of about one mCoulomb (mC) to about 1000 mC per skin tissue site by introducing one or more electric pulses to generate said total charge transfer at the skin tissue site, at substantially the same time as the introduction of the polynucleotide so as to result in the polynucleotide entering cells of the skin tissue for expression of the therapeutic polypeptide therein;
thereby enhancing the expression of the therapeutic polypeptide as compared to expression of the therapeutic polypeptide achieved by other methods for generating an electric field in target skin tissue.

BRIEF DESCRIPTION OF THE FIGURES

FIGS. 5A and 5B show a needle applicator having a hollow needle 510 and two electrical wires 520A and 520B that are held in the hollow portion of the needle 510.

FIG. 6 shows a pair of needle electrodes 610 and 620 that have substance-releasing sections 612 and 622 near the needle tips.

FIG. 7 shows a single needle applicator having a hollow center portion and at least four holes 712A, 712B, 714A, and 714B on the sidewalls near the needle tip.

FIG. 13, panels a–d, depict photomicrographs of skin samples stained with X-gal 3 days post application of lacZ DNA and: (a) no pulse (caliper pressure only); (b) pulsing (i.e., three exponential decay pulses of amplitude 120 V and pulse length of 10 ms administered from a BTX ECM 600 pulse Generator within about 1 minute) and caliper pressure treatment for 1 min.; (c) and (d) after the same treatment as panel (b) but with pulse length and post-pulse pressure times of 10 ms with 10 min. pressure and 20 ms with 10 min. pressure, respectively.

FIG. 16A shows GFP expressing cells are visible as well as small green fluorescent dots that indicate TOTO-1 labeled plasmid within cells that are not expressing the plasmid (100× magnification, fluorescent light only). FIG. 16B shows white light from a tungsten source added to the fluorescent light to simultaneously illuminate the GFP positive and negative cells (460× magnification).

FIG. 20 depicts an alternative embodiment of a shallow needle electrode array.

FIGS. 32A and 32B are graphs showing the effect of different electroporation pulse conditions on long term histological changes in porcine muscle following delivery of DNA to porcine hind limb quadriceps muscle. FIG. 32A shows area % of cellular infiltration by mononuclear infiltrating cells at the treatment site on day 14 post treatment and FIG. 32B shows the same on day 42 post treatment.

DETAILED DESCRIPTION OF THE INVENTION

Figure 1:
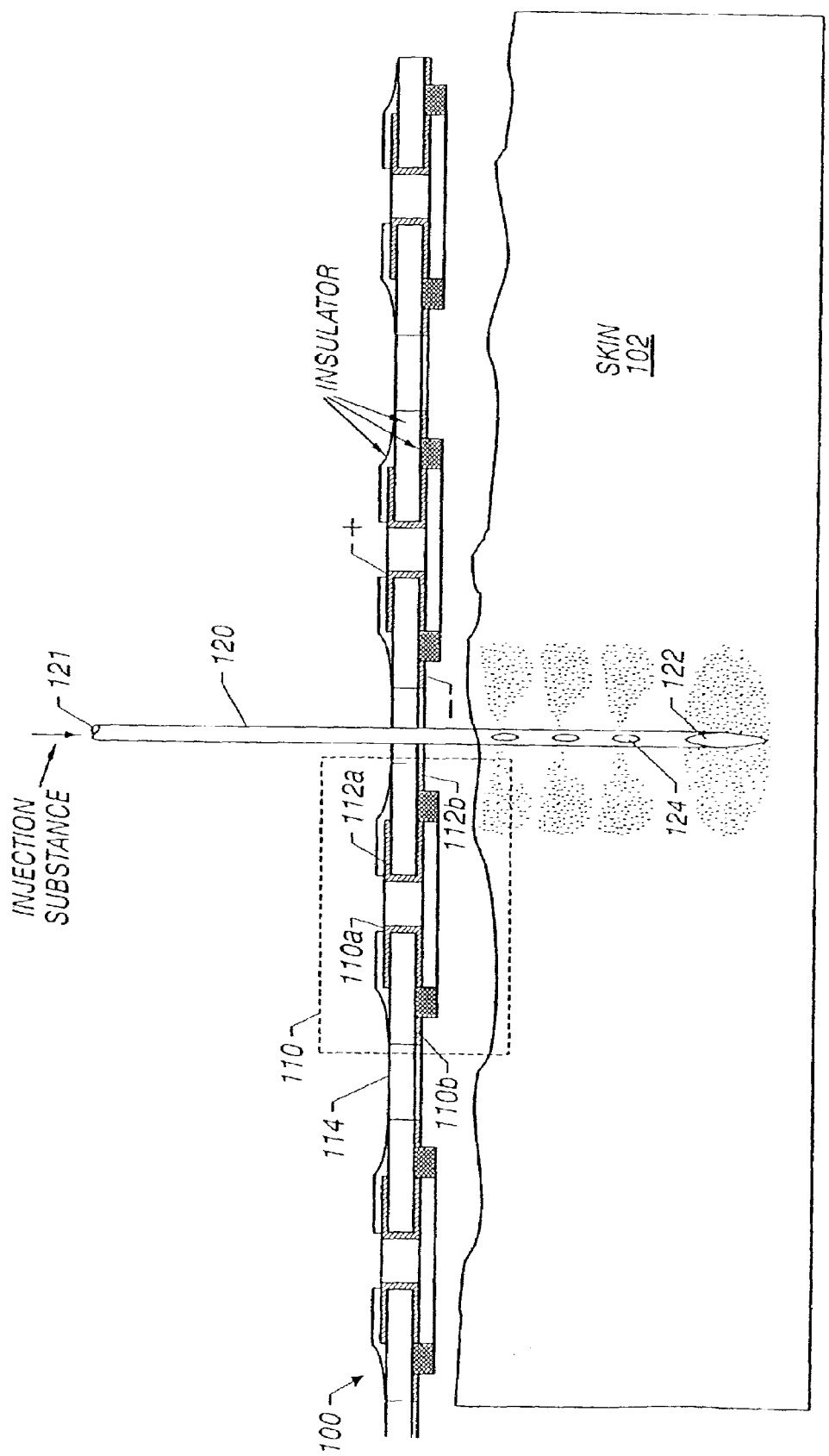
FIG. 1 shows a micropatch electroporation applicator that has a micropatch member 110 and an injection needle 120.

In accordance with the invention, there are provided in vivo methods for introducing a therapeutic agent into skin or muscle cells of a subject, said method comprising applying an electric field to said skin or muscle cells substantially contemporaneously with the application of said therapeutic agent to said skin or muscle cells, such that said therapeutic agent is introduced into said skin or muscle cells respectively.

The term "substantially contemporaneously" means that the molecule and the electroporation treatment are administered reasonably close together with respect to time. The administration of the molecule or therapeutic agent can be at any interval, depending upon such factors, for example, as the nature of the tumor, the condition of the patient, the vascularization of the tissue, the size and chemical characteristics of the molecule and half-life of the molecule.

As used herein, the terms "impulse," "pulse," "electrical impulse," "electrical pulse," "electric pulse," "electropulse" and variations thereof are interchangeable and all refer to an electrical stimulus. Although the various terms are frequently used herein in the singular, the singular forms of the terms include multiple pulses. Preferred electrical impulses are electric fields applied via electroporation. The pulse can be unipolar, bipolar, exponential or square waveform. Electric pulses contemplated for use in the practice of the invention include those pulses of sufficient voltage and duration to cause electroporation.

As used herein, the term "therapeutic agent" as used herein refers to drugs (e.g., chemotherapeutic agents), nucleic acids (e.g., polynucleotides), peptides and polypeptides, including antibodies and agents that have a cosmetic effect on the skin, e.g., agents that enhance the texture or appearance of skin and/or confer "anti-aging" benefits. The term "polynucleotides" include DNA, cDNA and RNA sequences, as further elaborated herein.

Therefore, in accordance with another embodiment, the invention provides a method for the introduction of nucleic acid into the cells of the skin and/or muscle, preferably human, by contacting the skin with nucleic acid and applying an electrical pulse to the targeted region. The electrical pulse is of sufficient voltage and duration to cause electroporation to happen so that the nucleic acid can penetrate into the cells of the skin and/or muscle and be expressed as a transgenic molecule. The biological expression of the nucleic acid component results in the transcription and translation of the delivered gene so that the targeted cells synthesize gene product de novo. Therapeutic applications include, for example, the augmentation of missing or underexpressed genes; the expression of genes that have a therapeutic value (e.g., inhibiting the action of harmful gene products by expressing a receptor to bind the product of an over-expressed gene); the expression of genes, the product of which elicits a desired immune response; and the like.

As will be understood by those of skill in the art, efficient expression of a nucleic acid encoding a therapeutic polypeptide generally requires that the nucleic acid sequence be operably associated with a regulatory sequence. Regulatory sequences contemplated for use in the practice of the invention include promoters, enhancers, and the like. As those of skill in the art will also appreciate, even when a promoter sequence is operably associated with the therapeutic nucleic acid, expression may be further augmented by operably associating an enhancer element or the like.

Promoters contemplated for use in the practice of the invention include the CMV, RSV LTR, MPSV LTR, SV40, the group of keratin specific promoters (e.g., the keratin and involucrin group of promoters). Presently, it is preferred that the promoters employed in the practice of the invention as applied to skin are specifically active in skin cells. The transcriptional promoters of a number of genes expressed in the epidermis have been characterized. Furthermore, such promoters tend to restrict expression to either the basal compartment or the suprabasal compartment. Keratin 14, for example, is expressed by basal keratinocytes, whereas involucrin is expressed by suprabasal keratinocytes. In addition, the keratin 14 and involucrin genes are highly expressed in keratinocytes, thus use of their promoters to drive transgene transcription yields not only target specificity, but also high levels of expression. The promoters for both genes have been successfully used to direct compartment-specific expression to the epidermis of transgenic mice.

Chemotherapeutic agents contemplated for use in the method of the invention typically have an antitumor or cytotoxic effect. Such drugs or agents include bleomycin (and alternative bleomycin formulations, including but not limited to peplomycin, bleomycin A5, and bleomycin A6), neocarcinostatin, suramin, doxorubicin, carboplatin, taxol, mitomycin C, cisplatin, and the like. Other chemotherapeutic agents will be known to those of skill in the art (see, for example The Merck Index). In addition, chemotherapeutic agents that are "membrane-acting" agents are also included in invention methods. These agents may have palliative effects as those listed above, or alternatively, they may be agents which act primarily by damaging the cell membrane. Examples of membrane-acting agents include N-alkylmelamide and para-chloro mercury benzoate. The chemical composition of the agent will dictate the most appropriate time to administer the agent in relation to the administration of the electric pulse. For example, while not wanting to be bound by a particular theory, it is believed that a drug having a low isoelectric point (e.g., neocarcinostatin, IEP=3.78), would likely be more effective if administered post-electroporation in order to avoid electrostatic interaction of the highly charged drug with the field. Further, such drugs as the standard bleomycin formulation, which have a very negative log P, (P being the partition coefficient between octanol and water), are very large in size (MW1400), and are hydrophilic, thereby associating closely with the lipid membrane, diffuse very slowly into a tumor cell and are typically administered prior to or substantially simultaneous with the electric pulse. In addition, certain agents may require modification in order to allow more efficient entry into the cell. For example, an agent such as taxol can be modified to increase solubility in water, which would allow more efficient entry into the cell. Electroporation facilitates entry of bleomycin or other similar drugs into the tumor cell by creating pores in the cell membrane.

In one embodiment of the invention, there is provided a method for the therapeutic application of electroporation to skin and/or muscle of a subject for introducing applied molecules into cells therein, comprising providing an array of electrodes, at least one of the electrodes having a needle configuration for penetrating tissue; inserting the needle electrode into selected tissue; positioning a second electrode of the array of electrodes in conductive relation to the selected tissue; applying pulses of high amplitude electric signals to the electrodes, proportionate to the distance between the electrodes, for electroporation of the tissue, such that said applied molecules are introduced into said skin or muscle cells. In another aspect of the invention, there is provided a method for the therapeutic application of electroporation to skin of a subject for introducing applied molecules into cells therein, comprising providing a non-invasive electrode, such as a caliper or meander electrode, and applying it to the skin and applying pulses of high amplitude electric signals to the electrodes, proportionate to the distance between the electrodes, for electroporation of the tissue, such that said applied molecules are introduced into said skin cells. In one aspect of these inventions, the molecules to be introduced are topically applied. In another aspect of these inventions, the molecules to be introduced are applied by other means such as injection, or the like. It should be understood that the electroporation of tissue can be performed in vitro, in vivo, or ex vivo. Electroporation can also be performed utilizing single cells, e.g., single cell suspensions or in vitro or ex vivo in cell culture.

It may be desirable to modulate the expression of a gene in a cell by the introduction of a molecule by the method of the invention. The term "modulate" envisions the suppression of expression of a gene when it is over-expressed, or augmentation of expression when it is under-expressed. Where a cell proliferative disorder is associated with the expression of a gene, for example, nucleic acid sequences that interfere with expression of the gene at the translational level can be used. This approach utilizes, for example, antisense nucleic acid, ribozymes, or triplex agents to block transcription or translation of a specific mRNA, either by masking that mRNA with an antisense nucleic acid or triplex agent, or by cleaving it by nucleolytic action.

Nucleic acids contemplated for use in the practice of the invention include naked DNA, naked RNA, naked plasmid DNA, either supercoiled or linear, and encapsulated DNA or RNA (e.g., in liposomes, microspheres, or the like). As will be understood by those of skill in the art, particles mixed with plasmid so as to "condense" the DNA molecule may also be employed.

Antisense nucleic acids are DNA or RNA molecules that are complementary to at least a portion of a specific mRNA molecule (see, e.g., Weintraub, *Scientific American*, 262:40, 1990). In the cell, the antisense nucleic acids hybridize to the corresponding mRNA, forming a double-stranded molecule. The antisense nucleic acids interfere with the translation of the mRNA, since the cell will not translate a mRNA that is double-stranded. Antisense oligomers of about 15 nucleotides are preferred, since they are easily synthesized and are less likely to cause deleterious effects than larger molecules when introduced into the target cell. The use of antisense methods to inhibit the in vitro translation of genes is well known in the art (see, e.g., Marcus-Sakura, *Anal. Biochem.*, 172:289, 1988).

Use of an oligonucleotide to stall transcription is known as the triplex strategy since the oligomer winds around double-helical DNA, forming a three-strand helix. Therefore, these triplex compounds can be designed to recognize a unique site on a chosen gene (Maher, et al., *Antisense Res. and Dev.*, 1(3):227, 1991; Helene, C., *Anticancer Drug Design*, 6(6):569, 1991). Accordingly, electroporation of nucleic acids useful for triplex formation is also contemplated as within the scope of the invention.

Ribozymes are RNA molecules possessing the ability to specifically cleave other single-stranded RNA or double-stranded DNA in a manner analogous to DNA restriction endonucleases. Through the modification of nucleotide sequences that encode these RNAs, it is possible to engineer molecules that recognize specific nucleotide sequences in an RNA molecule and cleave it (Cech, *J. Amer. Med. Assn.*, 260:3030, 1988). A major advantage of this approach is that, because they are sequence-specific, only mRNAs with particular sequences are inactivated.

There are two basic types of ribozymes namely, tetrahymena-type (Hasselhoff, *Nature*, 334:585, 1988) and "hammerhead"-type. Tetrahymena-type ribozymes recognize sequences that are four bases in length, while hammerhead-type ribozymes recognize base sequences in the range of 11–18 bases in length. The longer the recognition sequence, the greater the likelihood that the sequence will occur exclusively in the target mRNA species. Consequently, hammerhead-type ribozymes are preferable to tetrahymena-type ribozymes for inactivating a specific mRNA species and 18-based recognition sequences are preferable to shorter recognition sequences.

The invention also provides methods of gene therapy for the treatment of cell proliferative or immunologic disorders mediated by a particular gene or absence thereof. The term "cell proliferative disorder" denotes malignant as well as non-malignant cell populations, which often appear to differ from the surrounding tissue both morphologically and genotypically. Such therapy would achieve its therapeutic effect by introduction of a specific sense or antisense polynucleotide into cells having the disorder. Delivery of polynucleotides can be achieved using a recombinant expression vector such as a chimeric virus, or the polynucleotide can be delivered as "naked" DNA for example.

The polynucleotide sequences of the invention are DNA or RNA sequences having a therapeutic effect after being taken up by a cell. Nucleic acids contemplated for use in the practice of the invention can be double stranded DNA (e.g., plasmid, cosmid, phage, viral, YACS, BACS, other artificial chromosomes, and the like), single stranded DNA or RNA. The nucleic acids may be uncomplexed (i.e., "naked") or complexed (e.g., with chemical agents such as lipids (e.g., cationic), dendrimers, or other polyplexes that facilitate DNA penetration into tissues and through cell membranes, and the like). The DNA may also be encapsulated or formulated with protein complexes.

Examples of polynucleotides that are themselves therapeutic are anti-sense DNA and RNA; DNA coding for an anti-sense RNA; or DNA coding for tRNA or rRNA to replace defective or deficient endogenous molecules, and the like. The polynucleotides of the invention can also code for therapeutic polypeptides. As used herein, "polypeptide" is understood to be any translation product of a polynucleotide regardless of size, and whether glycosylated or not. Therapeutic polypeptides contemplated for use in the practice of the invention include, as a primary example, those polypeptides that can compensate for defective or deficient species in an animal, or those that act through toxic effects to limit or remove harmful cells from the body.

Also included are polynucleotides that encode metabolic enzymes and proteins, such as blood coagulation compounds (e.g., Factor vm or Factor IX), and the like.

In accordance with another embodiment of the invention, there are provided methods for inducing an immune response in a subject. Invention methods of this embodiment comprise applying an electric field to skin or muscle cells of the subject substantially contemporaneously with the application of an immune response-inducing agent to the skin or muscle cells, such that the immune response-inducing agent is introduced into the skin or muscle cells thereby inducing in the subject an immune response. As used herein, "immune response-inducing agent" means any agent, which upon introduction into the skin or muscle cells of a subject, results in an immune response, whether the response be a cellular response, a humoral response, or both. Immune response-inducing agents contemplated for use in the practice of the invention include expressible nucleic acids, and polypeptides.

Expressible DNA and mRNA can be delivered to cells to form therein a polypeptide translation product. If the nucleic acids are operatively associated with the proper regulatory sequences, enhanced synthesis of the encoded protein is achievable. DNA or RNA encoded polypeptides contemplated for use in the practice of the invention include immunizing polypeptides, pathogen-derived proteins, blood coagulation factors, peptide hormones, and the like. Peptide hormones include, for example, calcitonin (CT), parathyroid hormone (PTH), erythropoietin (Epo), insulin, cytokines, growth hormone, growth factors, and the like). Lymphokines contemplated for use in the practice of the invention include tumor necrosis factor, interleukins 1, 2, and 3, lymphotoxin, macrophage activating factor, migration inhibition factor, colony stimulating factor, alpha-interferon, beta-interferon, gamma-interferon and subtypes thereof. Blood coagulation factors contemplated for use in the practice of the invention include Factor VIII or Factor IX.

When the DNA or mRNA delivered to the cells codes for an immunizing peptide, invention methods can be applied to achieve improved and more effective immunity against infectious agents, including bacteria, intracellular viruses, tumor cells, and the like. Therapeutic polynucleotides provided by the invention can also code for immunity-conferring polypeptides, which can act as endogenous immunogens (i.e., antigen-containing polypeptides) to provoke a humoral immune response, a cellular immune response-inducing agent response, or both. Methods for inducing such responses and targeting specific cells for specific responses are described, for example, in U.S. Pat. No. 5,589,466. The polynucleotides employed in accordance with the invention can also code for an antibody. In this regard, the term "antibody" encompasses whole immunoglobulin of any class, chimeric antibodies and hybrid antibodies with dual or multiple antigen or epitope specificities, and fragments, such as $F(ab)_2$, Fab', Fab, and the like, including hybrid fragments thereof. Also included within the meaning of "antibody" are conjugates of such fragments, and so-called antigen binding proteins (single chain antibodies) as described, for example, in U.S. Pat. No. 4,704,692, hereby incorporated by reference herein in its entirety.

Thus, an isolated polynucleotide coding for variable regions of an antibody can be introduced, in accordance with the invention, to enable the treated subject to produce antibody in situ. For illustrative methodology relating to obtaining antibody-encoding polynucleotides, see Ward et al. *Nature*, 341:544–546 (1989); Gillies et al., *Biotechnol.* 7:799–804 (1989). The antibody in turn exerts a therapeutic effect, for example, by binding a surface antigen associated with a pathogen. Alternatively, the encoded antibodies can be anti-idiotypic antibodies (antibodies that bind other antibodies) as described, for example, in U.S. Pat. No. 4,699,880. Such anti-idiotypic antibodies could bind endogenous or foreign antibodies in a treated individual, thereby ameliorating or preventing pathological conditions associated with an immune response, (e.g., in the context of an autoimmune disease such as lupus and the like).

It is presently preferred that polynucleotide sequences used in the practice of the invention code for therapeutic or immunogenic polypeptides. These polynucleotide sequences may be used in association with other polynucleotide sequences coding for regulatory proteins that control the expression of the therapeutic or immunogenic polypeptides. The regulatory protein(s) so employed can act in any number of regulatory manners known to those of skill in the art, such as by binding to DNA so as to regulate its transcription, by binding to messenger RNA to increase or decrease its stability or translation efficiency, and the like.

The polynucleotide material delivered to the cells in vivo can take any number of forms, and the invention is not limited to any particular polynucleotide coding for any particular polypeptide. Plasmids containing genes coding for a large number of physiologically active peptides and antigens or immunogens are contemplated for use in the practice of the invention and can be readily obtained by those of skill in the art.

Various viral vectors can also be utilized in the practice of the invention and include adenovirus, herpes virus, vaccinia, RNA virus, and the like. It is presently preferred that the virus be an RNA virus such as a retrovirus. Preferably, the retroviral vector is a derivative of a murine or avian retrovirus. Examples of retroviral vectors in which a single foreign gene can be inserted include, but are not limited to: Moloney murine leukemia virus (MoMuLV), Harvey murine sarcoma virus (HaMuSV), murine mammary tumor virus (MuMTV), and Rous Sarcoma Virus (RSV). When the subject is a human, a vector such as the gibbon ape leukemia virus (GaLV), or the like can be utilized. A number of additional retroviral vectors can incorporate multiple genes. All of these vectors can transfer or incorporate a gene for a selectable marker so that transduced cells can be identified and generated.

Therapeutic peptides or polypeptides may also be included in the therapeutic method of the invention. For example, immunomodulatory agents and other biological response modifiers can be administered for incorporation by a cell. As used herein, the term "biological response modifiers" encompasses substances that are involved in modifying the immune response. Examples of immune response modifiers include such compounds as lymphokines, and the like. Lymphokines include, for example, tumor necrosis factor, interleukins 1, 2, and 3, lymphotoxin, macrophage activating factor, migration inhibition factor, colony stimulating factor, alpha-interferon, beta-interferon, gamma-interferon and their subtypes.

Administration of a chemotherapeutic agent, polynucleotide or polypeptide, in the practice of invention methods may be by topical application. Accordingly, a "permeation enhancer" also can be included with electropulsing to increase introduction of a composition. As used herein, the term "permeation enhancer" refers to any action (e.g., mechanical, physical, chemical) or any composition that can increase or "augment" introduction of a composition into skin and/or muscle cells. The term "augment," when used herein as a modifier of introduction, means that the rate (over time) or amount of composition introduced into skin and/or muscle cells via electropulsing is greater than that produced by electropulsing in the absence of the permeation enhancer. Thus, administering a permeation enhancer prior to, substantially contemporaneously with or after topical application of a therapeutic agent serves to "augment" electrically induced introduction of the composition into skin and/or muscle cells. Alternatively, a permeation enhancer can be mixed with the composition in the pharmaceutical formulation to be introduced. Permeation enhancer compositions that increase the permeability of skin and/or muscle cells include, for example, alcohols (e.g., methanol), alkyl methyl sulfoxides (e.g., DMSO), pyrrolidones (e.g., 2-pyrrolidone), surfactants, urea, glycerol monolaurate, polyethylene glycol monolaurate, glycerol monolaurate, docainehydrochloride, hydrocortisone, menthol, methyl salicylate, and the like. Permeation enhancers further include mechanical or physical actions that function in association with an electrical impulse (e.g., abrasion, vibration, ultrasound, and the like).

Depending on the nature of the therapeutic agent, the desired depth of penetration, the target tissue type, and the like, it may be desirable to conduct electroporation in combination with other electrically-based treatment modalities. Electropulsing conducted substantially contemporaneously with iontophoresis (IPH), can produce a greater therapeutic effect than either applying the pulse or iontophoresis alone. Furthermore, electroincorporation (EI) (see, e.g., U.S. Pat. No. 5,464,386, which is hereby incorporated by reference herein in its entirety), or electropulsing in combination with IPH and liposomal formulation can enhance delivery significantly. (see, e.g., Badkar, et al., Drug Delivery 6 (1999) 111–115). Accordingly, in another embodiment of the invention, electropulsing is used in conjunction with one or more of iontophoresis and electroincorporation.

As used herein, the term "transdermally introducing" and grammatical variations thereof, refers to the delivery of a composition into the skin, through/across the skin, or a combination thereof.

Targeting the cells of the skin for gene therapy has several advantages. First of all, the epidermis is an accessible tissue, which simplifies approaches for introduction of a transgene. Also, if necessary, large areas of skin can be treated. Keratinocytes, the predominant cell type in the epidermis and hence the cellular target for some gene transfer, form the outer-most barriers of the skin, making them amenable to in vivo manipulation. The accessibility of the epidermis raises the potential for use of non-invasive, topical methods for gene transfer. The epidermis is a stratified squamous epithelium consisting of a basal proliferating compartment and a suprabasal, differentiating compartment. By targeting gene transfer to the basal compartment, genes can be introduced into epidermal stem cells. Although gene expression may be limited to certain types of skin cells, the transgene product may exert a systemic effect. For example, keratinocytes function as synthetic and secretory cells, and transgene products generated in the epidermis are known to enter systemic circulation [Wang et al., PNAS 94:219–226; 1997; Fakharzadah et al., Blood 95:2799–2805, 1997]. As an advantage for DNA vaccination, the skin contains potent antigen presenting cells (APCs), critical to an effective immune response [Falo, L. D., Proc. Assoc. Am. Physicians 111:211–219, 1999]. Finally, epidermal cells slough off after a relatively short life span, thereby eliminating the bulk of the foreign DNA from the patient's body. This may help to lower the real or perceived risk of negative long-term effects of transfecting cells with foreign DNA. Of course, the latter approach is only useful for treatments that require relatively short periods of gene expression, e.g., DNA vaccination, or the treatment of drug-induced anemia.

Various treatment regimens are thus made possible. For example, single gene recessive disorders such as lamellar ichthyosis (LI) or X-linked ichthyosis (XLI) could be treated using the gene transglutaminase 1, or the gene for the steroid sulfatase arylsulfatase C, respectively. Epidermal stem cells give rise to basal, transiently amplifying cells, which have a limited capacity to divide. In turn, these cells give rise to the differentiating keratinocytes of the suprabasal epidermis. Thus, by achieving transgene expression in progenitor basal keratinocytes, methods for long-term, sustained gene therapy are provided.

Keratinocytes function well as synthetic and secretory cells. Keratinocytes have been shown to synthesize and secrete in-vivo the products of transfected genes. Circulating transgene-derived proteins such as growth hormone (GH) (22 kD), ApoE (34 kD), and FIX (57 kD) have been detected in athymic mice bearing grafts of keratinocytes. This demonstrates that transgene products expressed in the epidermis can penetrate the basement membrane zone and reach the systemic circulation.

Noninvasive EP of skin involves two distinct processes, namely the perforation of the stratum corneum and the transmembrane delivery of DNA into the skin cells. Poration of the stratum corneum is preferably achieved with high voltage pulses, whereas DNA delivery into cells is preferably accomplished with pulses of lower voltage and longer duration [Aihara and Miyazaki, Nat. Biotechnol. 16:867–870, 1998; Weaver and Chizmadzhev, in C. Polk, E. Postow (Eds), Handbook of Biological Effects of Electromagnetic Fields, $2^{nd}$ edn. CRC Press, Boca Raton, Fla., pp. 247–274, 1996]. Invasive skin EP with needle electrodes circumvents the need for electroporating the stratum corneum but has some drawbacks. The EP conditions disclosed in Example 14 herein lower the resistance of the stratum corneum by a factor of about 200 while allowing efficient DNA delivery and gene expression. Thus, the invented conditions permit efficient introduction of DNA into cells without application of an invasive electrode and without application of numerous electric pulses.

The design of the electrodes used for skin EP is important in several aspects. Electrodes must deliver an electrical field of sufficient strength and three-dimensional distribution to exert effective electroporation while keeping potential tissue damage to a minimum. Preferably, electrodes should also be easy to apply, be patient-friendly, hygienic, and inexpensive. The types of electrodes used can be grouped into invasive and noninvasive models.

Figure 10A:
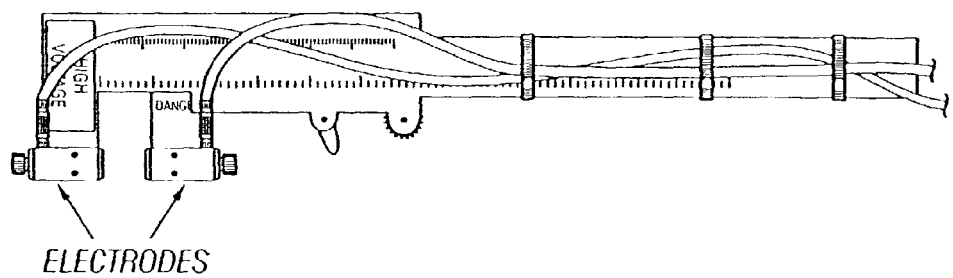
FIG. 10A depicts an example of a caliper type electrode (P/N 384, available from Genetronics, Inc.) comprising of two brass electrodes, each measuring about 1 cm×1 cm, mounted on a caliper scale which allows for accurate measurement of the inter-electrode

Invasive designs use arrays of needle electrodes of various complexity [Drabick et al., Mol. Ther. 3:249–255, 2001; Glasspool-Malone et al., Mol. Ther. 2:140–146, 2001; Ilie et al., J. Invest. Dermatol. 116:40–49, 2001]. Noninvasive electrodes include plate or "caliper"-type electrodes (see FIGS. 10 and 33) [Heller et al., DNA Cell Biol. 20:21–26, 2001; Dev et al., IEEE Trans. Plasma Sci. 28:206–223, 2000; Hofmann, in M. J. Jaroszeski et al. (Eds.), Electochemotherapy, Electrogenetherapy, and Transdermal Drug Delivery, Humana Press, Totwn, N.J., 2000, pp. 37–62; Zhang et al., Bioelectrochem. Bioenerg. 42:283–292, 1997], parallel wire electrodes [Heller et al., DNA Cell Biol. 20:21–26, 2001], and meander-type electrodes (see FIGS. 10 and 33) [Hofmann, in M. J. Jaroszeski et al. (Eds.), Electochemotherapy, Electrogenetherapy, and Transdermal Drug Delivery, Humana Press, Totwn, N.J., 2000, pp. 37–62; Hofmann et al., Bioelectrochem. Bioenerg. 38:209–222, 1995]. Noninvasive electrodes have the advantage of being more readily accepted by the patient (no fear of needles, no pain of insertion), and provide less opportunity for infection.

In one embodiment, the electrode is a wire electrode (useful for in vitro studies, and the like). In another embodiment, the electrode is a plurality of electrodes (e.g., a micropatch electrode as described in U.S. Pat. No. 6,192,270, which is hereby incorporated herein in its entirety by reference). In still yet another embodiment, the electrode comprises a meander electrode (e.g., an array of interweaving electrode fingers, with a typical electrode width in the range of about 0.2 up to about 1 mm, and an electrode gap of about 0.2 mm, wherein the gap can be filled with an electrically insulating substance) or a caliper electrode; see FIGS. 10 and 33. In an additional embodiment, the electrode is a porous electrode. The various electrodes used herein are preferably insulated to protect against excess heat or burning, current leakage, shock, etc. Appropriate electric pulsing parameters are set forth herein or can be determined using the teachings herein and, in view of these parameters, the skilled artisan can select among various suitable electrode types (e.g., ceramic, metal, etc.) and configurations (single wire, multiple wire, etc.) available in the art. In one embodiment of the invention, a square wave pulse is applied, wherein the pulse is at least 50 V for about 10 up to 20 ms. Of course other pulse types, voltages and times may be appropriate, as will be understood by those of skill in the art.

In accordance with additional embodiments of the invention, there are provided a number of improved electroporation devices that may be advantageously used in different applications. Examples of these additional embodiments are described below, with reference to attached figures.

FIG. 1 shows a micropatch electroporation applicator 100 that has a micropatch member 110 and an injection needle 120. The micropatch 100 includes a plurality of patch elements 110 that are positioned relative to one another to form a substantially planar array. Each patch element 110 includes two pairs of electrodes, a first pair having electrodes 110A and 110B and a second pair having electrodes 120A and 120B. The two electrodes 110A and 110B (or 112A and 112B) in each pair are electrically insulated from each other and are applied with different electrical potentials to produce a voltage therebetween. For example, the electrode 110A may be at a positive voltage and the electrode 110B may be at a negative voltage. An electrical control circuit (not shown) may be connected to the micropatch member 100 to produce desired electrical pulses at each patch element 110. One embodiment of the micropatch member 100 is disclosed in pending U.S. application Ser. No. 08/905,240, "Method and Apparatus for Using Electroporation Mediated Delivery of Drugs and Genes," filed on Aug. 1, 1997, which is incorporated herein by reference in its entirety. The micropatch member 100 can be placed upon a tissue surface 102 such as a person's skin to apply electrical pulses to the tissue surface 102.

The micropatch member 100 also includes a plurality of gaps 114 between adjacent patch elements 110. Such gaps 114 are formed of an electrically insulating material and can be penetrated by sharp objects such as the injection needle 120. The injection needle 120 is configured to include a conduit 121 for transporting an injection substance to the needle tip 122. One or more holes 124 are optionally formed on the side walls of the needle 120 near the needle tip 122 so that the injection substance can be released not only from the needle tip 122 but also from these holes 124. The injection needle 120 may be formed of a metal but may also be formed of a suitably rigid insulating material. In operation, the injection needle 120 supplies injection substance to a target tissue area and the micropatch member 100 operates in conjunction with a power supply to cause electroporation of the target tissue.

Figure 2:
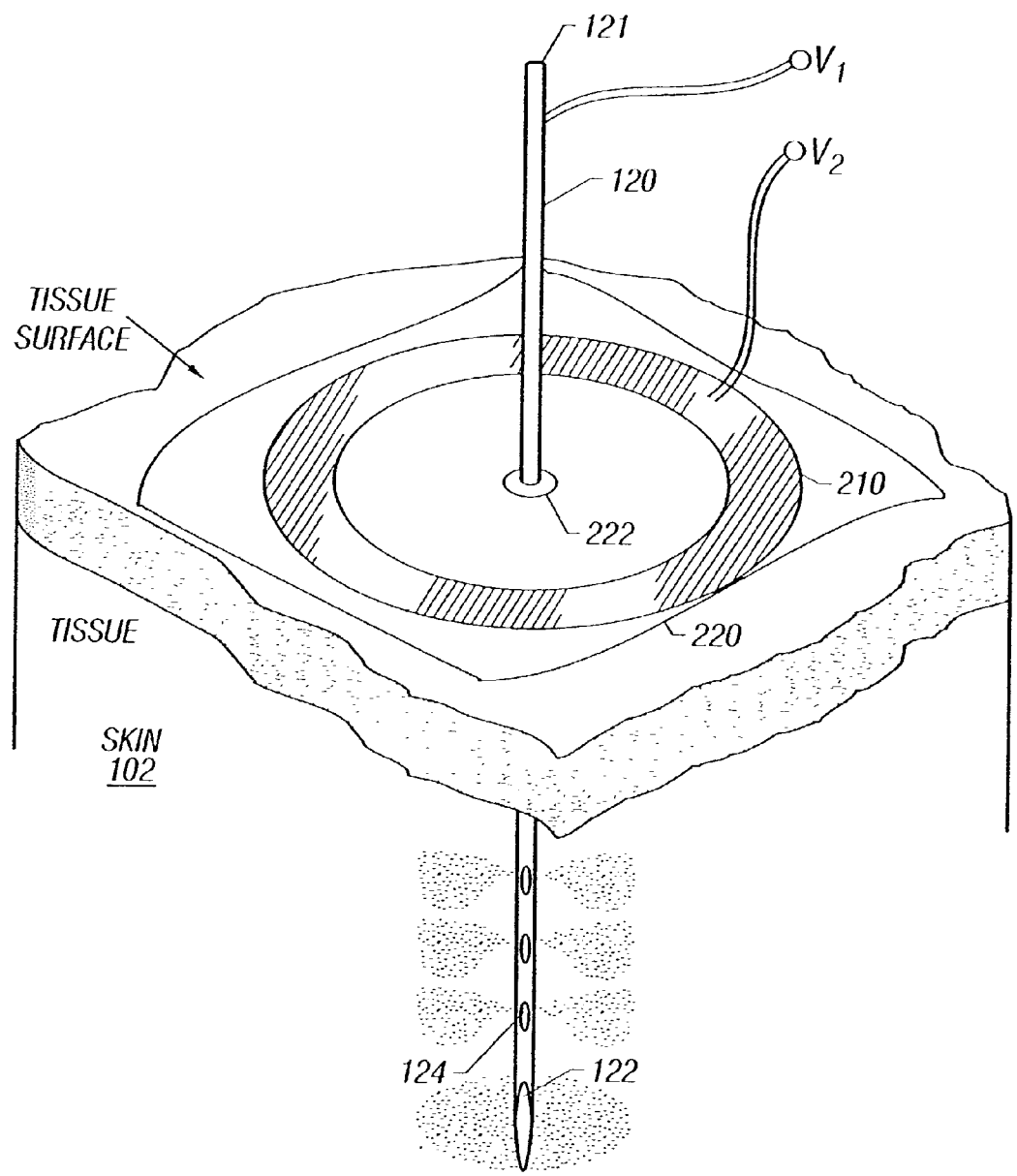
FIG. 2 shows an electroporation applicator that replaces the micropatch member 100 in FIG. 1 with a ring-shaped electrode 210.

FIG. 2 shows an electroporation applicator wherein the micropatch member 100 depicted in FIG. 1 is replaced with a ring-shaped electrode 210. Unlike the applicator shown in FIG. 1, the injection needle 120 in this embodiment also functions as an electrode. Hence, at least a part of the injection needle 120 must be formed of an electrical conductor. In the embodiment illustrated in FIG. 2, the needle 120 is formed of a metal. The ring-shaped electrode 220 may be in any shape, including but not limited to, a circular ring as shown, a square ring, or the like. An electrical insulating shield 220 is implemented to provide a support to the ring-shaped electrode 200 and to electrically insulate a tissue under treatment from the electrode 200. A through hole 222 is formed on shield 220 within the center opening of the ring-shaped electrode 200 for positioning the injection needle 120. The needle electrode may be modified to provide for radial delivery of an injection substance, for example, by providing one or more holes disposed along its length and proximal to the needle tip, wherein said holes are in fluid communication with the hollow interior of the injection needle.

An electrical control circuit (not shown) is connected to both the injection needle 120 and the ring-shaped electrode 210 to produce desired electrical pulses, causing electroporation and augmented delivery of the injection substance to the target tissue.

Figure 3:
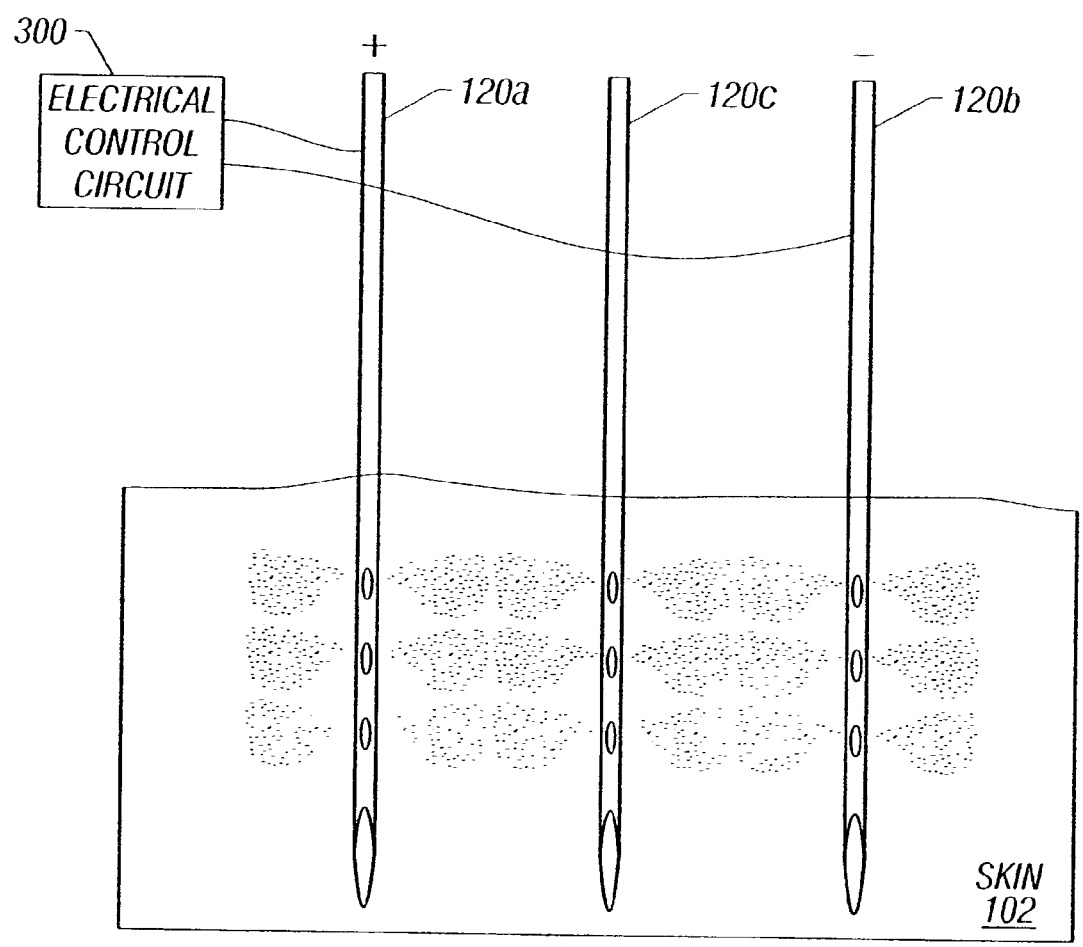
FIG. 3 shows a device having three injection needles 120A, 120B, and 120C connected to an electrical control circuit 300 to function as a pair of electrodes.

FIG. 3 shows a device having a plurality of paired electrode needles and at least one injection needle. In the embodiment depicted in FIG. 3, the electrode has three needles 120A, 120B, and 120C. Needles 120A and 120B are connected to an electrical control circuit 300 to function as a pair of electrodes. Additional paired electrode needles may be employed. The needle 120C is not used to apply electrical pulses to the tissue under treatment but is used as an injection port to supply injection substance to the electroporated tissue area. Substantially contemporaneously with the injection of an injection substance, voltage difference is applied between the needle electrodes 120 to produce desired electrical pulses, causing electroporation and augmented delivery of the injection substance to the target tissue. The injection needle may be modified to provide for radial delivery of an injection substance, for example, by providing one or more holes disposed along its length and proximal to the needle tip, wherein said holes are in fluid communication with the hollow interior of the injection needle.

Figure 4B:
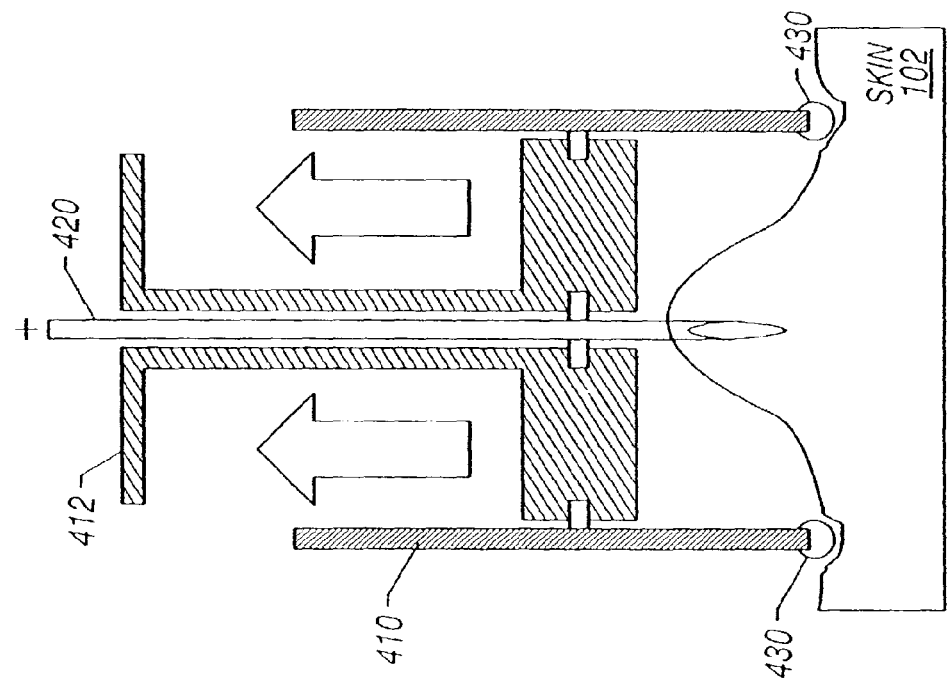
FIG. 4A shows an electroporation device based on the device shown in FIG. 2. A syringe 410 is implemented to hold an injection needle electrode 420 and a ring electrode 430.
Figure 4A:
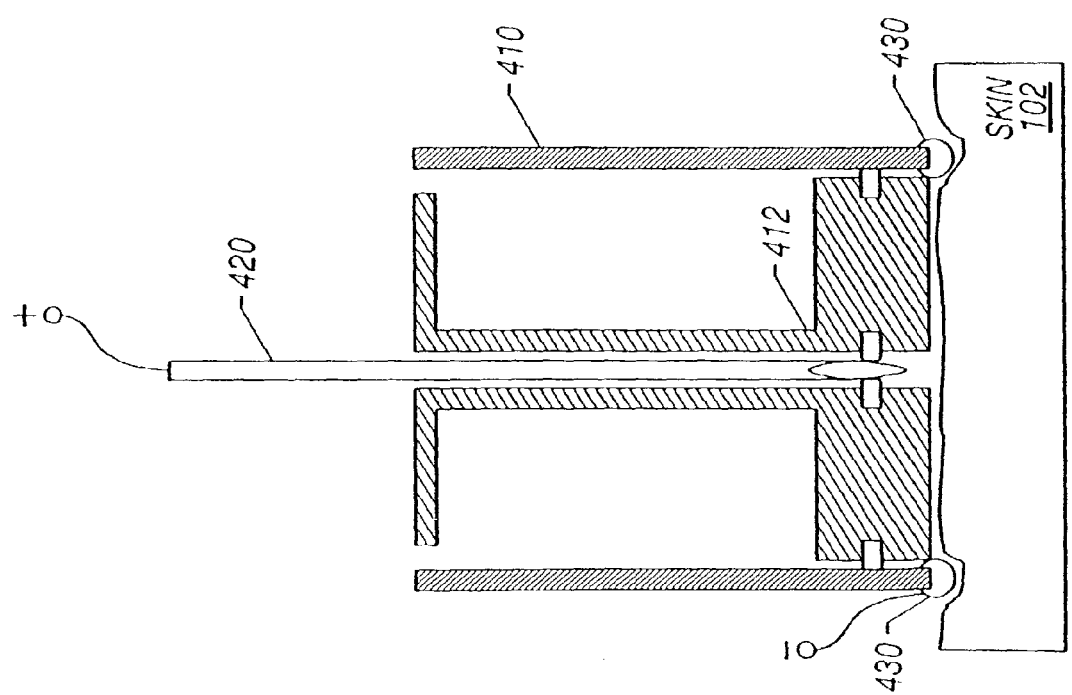

FIG. 4A shows an electroporation device based on the device shown in FIG. 2. A suction generating device such as a syringe 410 is implemented to hold an injection needle electrode 420 and a ring electrode 430. In the depicted embodiment, the suction device is a syringe 410 having a piston 412 which is slidably with, and sealingly disposed about the injection needle electrode 420. As used herein, "sealingly disposed about" means that the piston is fitted around the needle closely enough that a partial vacuum can be created upon withdrawal of the piston. The close fit may be facilitated, for example, by providing a gasket, or the like. In this manner, when the piston 412 is retracted, or suction is otherwise generated, a partial vacuum is created in the syringe 410 and skin to which the device is applied is partially lifted up by action of the vacuum (FIG. 4B). This facilitates the penetration of the skin by the injection needle electrode 420. Substantially contemporaneously with the injection of an injection substance, voltage difference is applied between the needle electrode 420 and the ring electrode 430 so that electrical pulses can be generated, causing electroporation and augmented delivery of the injection substance to the target tissue.

FIGS. 5A and 5B show a needle applicator having a hollow needle 510 and two electrical wires 520A and 520B that are held in the hollow portion of the needle 510. Each wire (e.g., 520A) has an insulated portion (e.g., 522A) and an exposed tip portion (e.g., 522B). In operation, the needle 510 penetrates a tissue and then is withdrawn to "plant" the exposed tip portions of the two wires 520A and 520B in the tissue (FIG. 5B). Substantially contemporaneously with the injection of an injection substance, voltage difference is applied between the wires 520A and 520B such that electrical pulses can be generated, causing electroporation and augmented delivery of the injection substance to the target tissue.

FIG. 6 shows a pair of needle electrodes 610 and 620 that have substance-releasing sections 612 and 622 near the needle tips. The substance-releasing sections 612 and 622 are configured to have an injection substance (e.g., a selected DNA) associated therewith. The substance-releasing sections may be formed of any biocompatible suitably absorbent material or material to which injection substance will adhere. Materials contemplated for use as substance-releasing sections include lipids, cationic lipids, heparin, hyaluronic acid, and the like. When the needles are penetrated within a tissue, electrical pulses are applied to the needle electrodes 610 and 620 so that injection substance applied substantially contemporaneously therewith can be electroporated into the cells between the electrodes.

As used herein, "biocompatible" or "biocompatible material" means a material that is suitable for introduction into the human body for therapeutic purposes.

FIG. 7 shows a single needle applicator. A needle 710 has a hollow center portion and at least four holes 712A, 712B, 714A, and 714B on the side walls proximal to the needle tip. Paired holes (e.g., 712A and 712B) are preferably arranged relatively proximal and distal to the needle tip along the same side of the needle body. Holes 714A and 714B are similarly arranged along the needle body but are radially spaced from holes 712A and 712B. The needle 710 is either formed of an insulator or coated with an insulating layer. Two electrical wires 720 and 730 located in the hollow center portion of the needle respectively run through the holes 714A, 714B and 712A, 712B to so that wire sections 720A and 720B are exposed on the exterior of the needle body 710. Each wire is coated with an insulator layer except for the exposed section. Different electrical potentials are applied to the wires 720 and 730 to produce electrical pulses between the exposed sections 720A and 720B. Additional holes may be formed near the holes 712A, 712B, 714A, 714B for delivering an injection substance.

Figure 8:
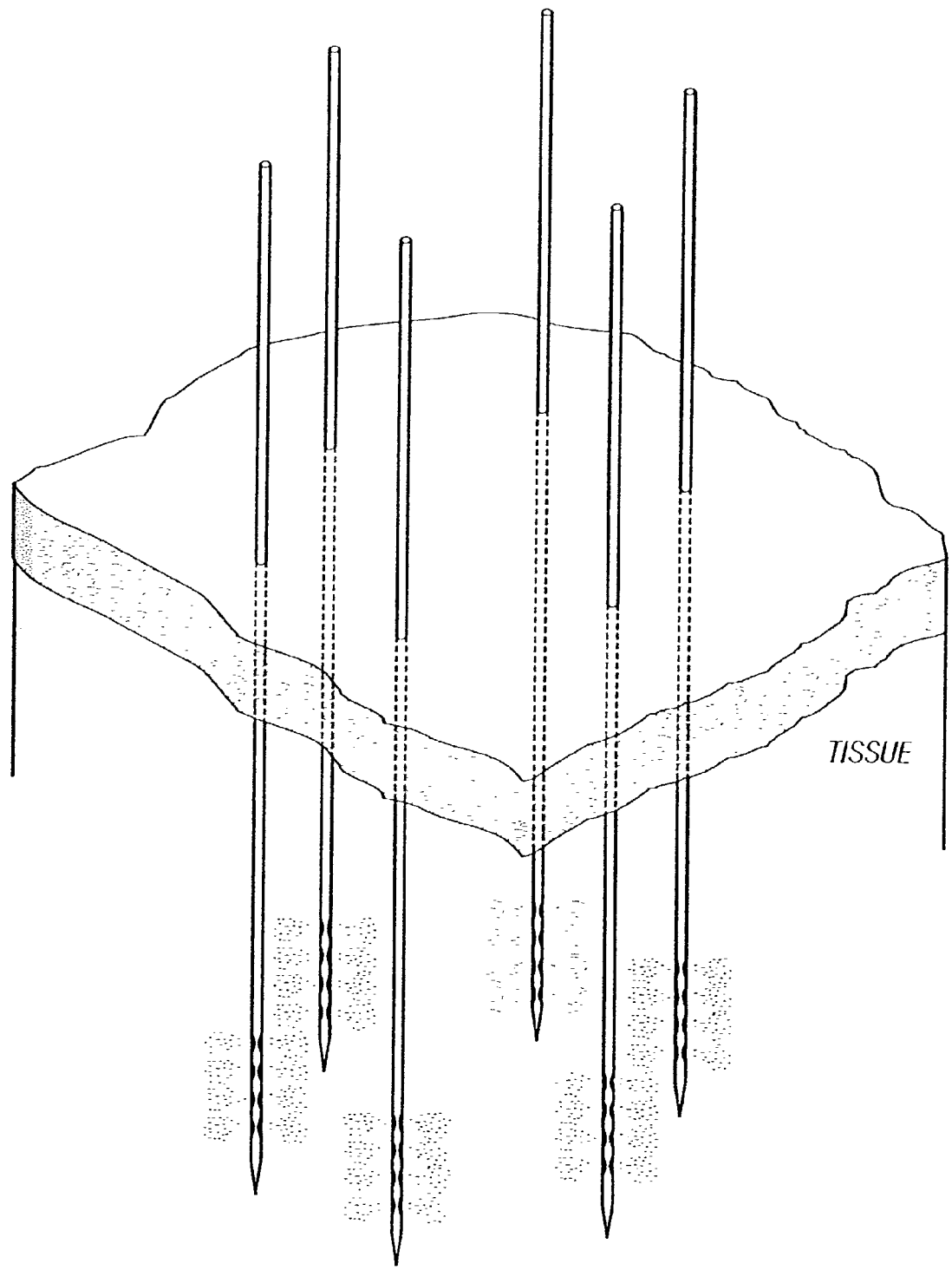
FIG. 8 shows an applicator having an array of 6 needle electrodes. Each needle electrode is used to apply both electrical pulses and a therapeutic agent.

FIG. 8 shows an applicator having an array of 6 needle electrodes. Each needle electrode is used to apply both electrical pulses and an injection substance. As illustrated, holes are formed on the side walls near the needle tip for releasing an injection substance into the tissue.

Figure 9:
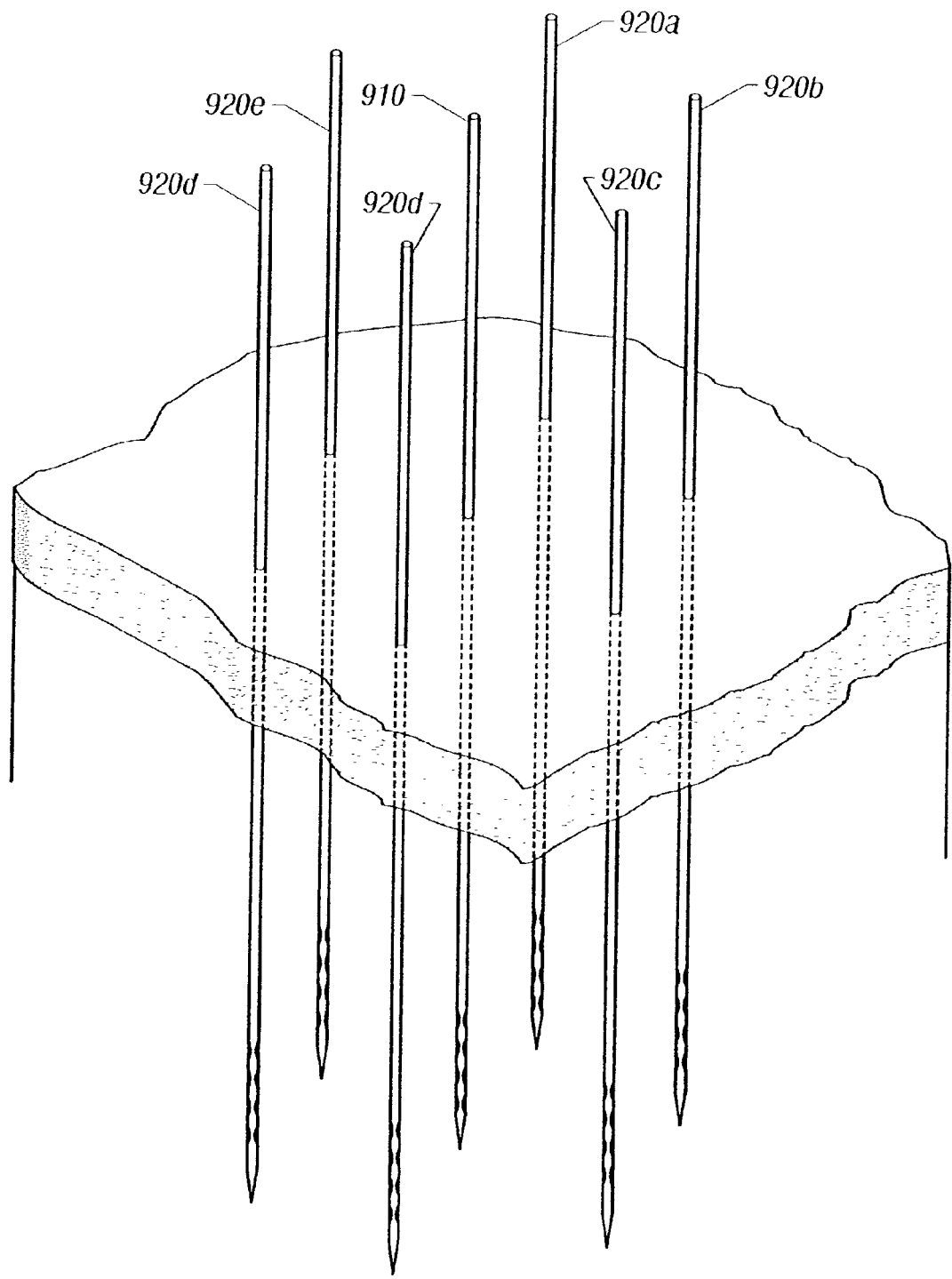
FIG. 9 shows another applicator having an array of needle electrodes (920A, 920B, etc.). A substance-releasing needle 910 is located in the center of the array and has holes near the needle tip for releasing a DNA.

FIG. 9 shows another applicator having an array of needle electrodes (920A, 920B, etc.). A substance-releasing needle 910 is located in the center of the array and has holes near the needle tip for releasing an injection substance. Substantially contemporaneously with the injection of an injection substance, voltage difference is applied between pairs of needles such that electrical pulses can be generated, causing electroporation and augmented delivery of the injection substance to the target tissue.

The needle 910 may be either electrically active to be pulsed against the surrounding needle electrodes or is electrically passive.

As used herein, "injection substance" means any therapeutic agent to be delivered to the target tissue. As described herein, therapeutic agents contemplated for use in the practice of the invention include nucleic acids, polypeptides, chemotherapeutic agents and the like.

Figure 10B:
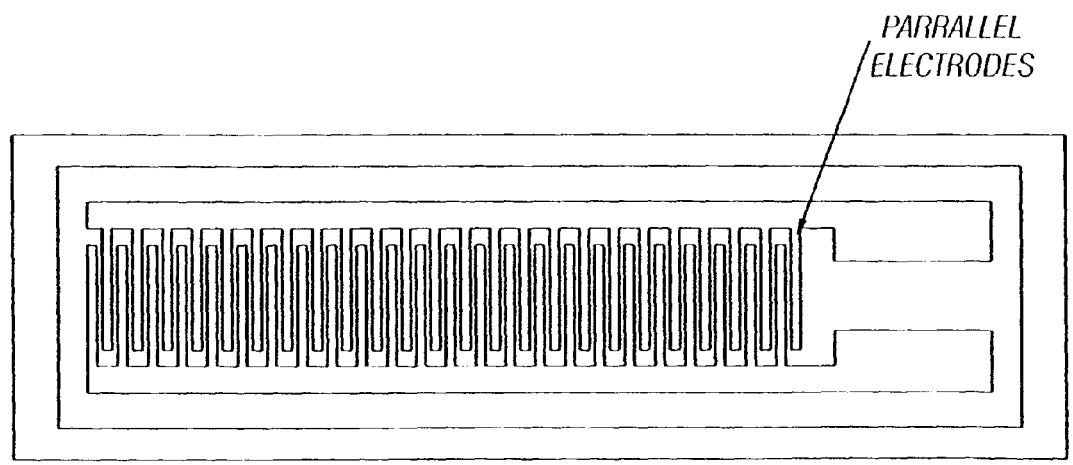
FIG. 10B depicts a meander electrode, comprising an array of interweaving electrode fingers. In this embodiment, the electrode finger width is about 2 mm and the electrode gap is about 0.2 mm.
Figure 11:
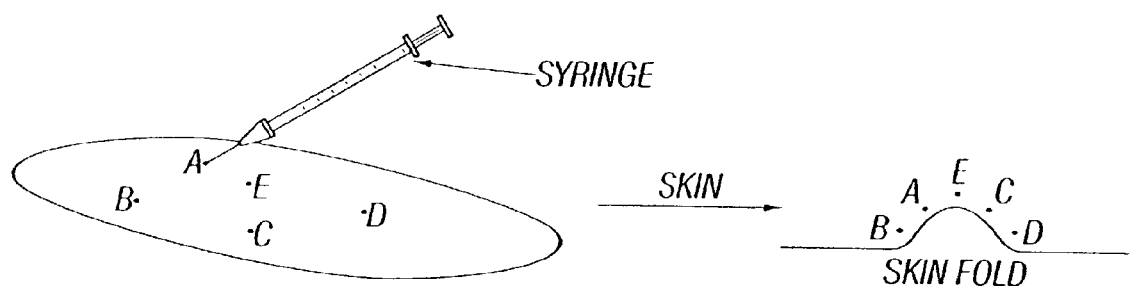
FIG. 11 depicts a method for introducing naked DNA into the skin comprising walk around intradermal injection of DNA into sites A–E, followed by electropulsing a thin fold of skin using a caliper electrode.
Figure 12:
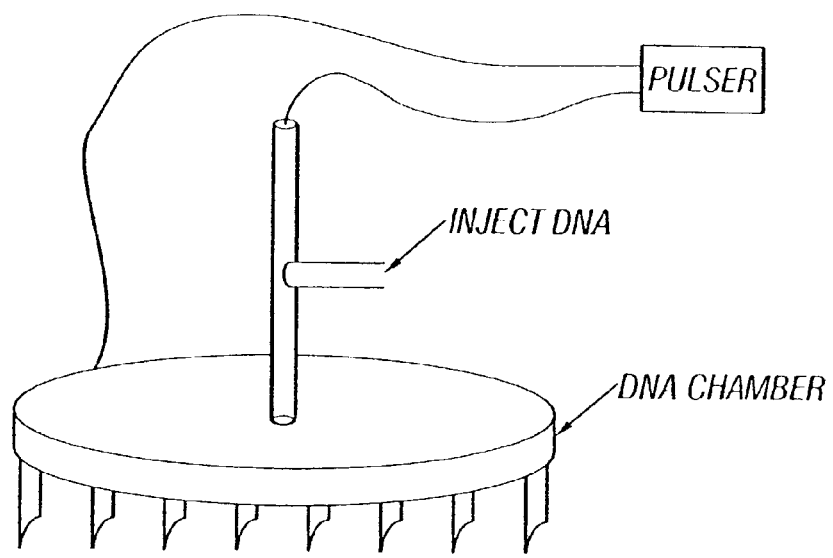
FIG. 12 depicts a microneedle electrode array with integrated container for therapeutic agent and therapeutic agent injector needle.
Figure 33:
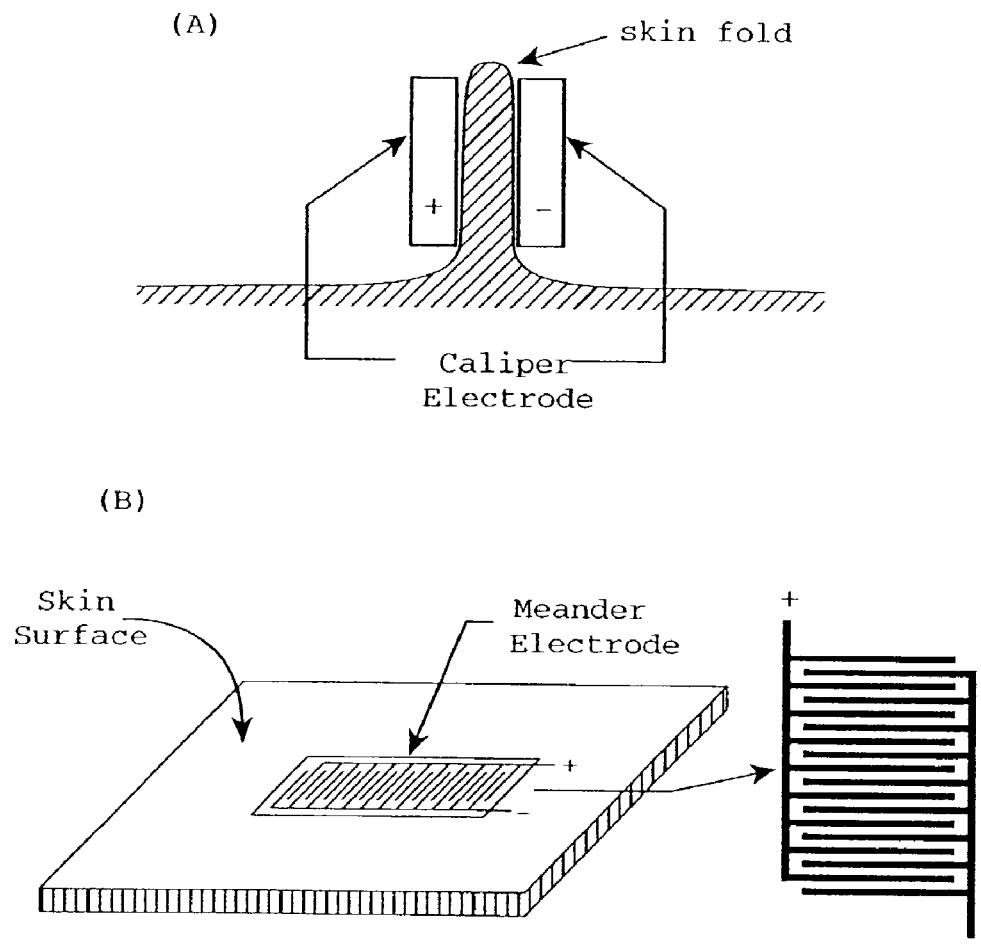
FIGS. 33A and 33B depict caliper and meander electrodes. Both electrodes are applied topically. The caliper electrode squeezes the skin between two metal plates, and the uniform electrical field is applied to this skin fold. The meander electrode is placed on the surface of the skin. The electrical field is generated between each positive and negative electrode, with a component of the filed penetrating the skin.

FIGS. 10 and 33, parts A and B, show non-invasive electrodes. A caliper electrode is shown in part A of FIGS. 10 and 33; a meander electrode is shown in part B of FIGS. 10 and 33. Such non-invasive electrodes are applied to the surface of the skin and, upon receipt of an electric charge, effect generation of an electric field under the skin surface. Non-invasive electrodes, such as a meander electrode, can be gentler, more patient-friendly, and more versatile than invasive electrodes or even caliper electrodes. The flat, flexible meander electrode can be made to adhere and conform to the specific shape and area of skin to be treated.

In accordance with another embodiment of the invention, there are provided electrode kits for use in conjunction with electroporation therapy, each kit containing the components of the electrodes described herein. For example, in one aspect, there is provided an electrode kit comprising a micropatch electrode, and an injection needle, optionally comprising one or more holes disposed along its length and proximal to the needle tip, wherein the holes are in fluid communication with the hollow interior of the injection needle.

With all of the above electroporation devices, a brief time of iontophoresis may be applied to distribute the DNA between the electrodes before pulsing for electroporation. The needles can be used for iontophoresis between two or among three or more needles. Iontophoresis can also be performed between any needle and other electrodes such as between the injection needle 120 and the ring electrode 210 in FIG. 2. Therefore, in accordance with another embodiment of the invention, there are provided methods for introducing therapeutic agents into skin cells of a subject, said method comprising employing an electroporation method as described herein in conjunction with iontophoresis and or electroincorporation.

Additional functional components that can be added to the invention electrical apparatus include, for example, an iontophoresis unit (IPH), which can be used in combination with an electrical impulse to transdermally introduce a greater amount of the composition into and/or across the skin than pulsing alone, or that can drive the composition deeper into the skin and/or muscle, if desired. A controlling means (e.g., a switching unit), such as an automated switch, optionally programmable, may be used to control any of the parameters of invention apparatus, including, for example, application of pulse alone, the time between applying the impulse and applying IPH, as well as optionally controlling the time during which IPH is applied. Each parameter will be determined by the composition introduced, the desired effect, the concentration etc. In one aspect of this embodiment, electrodes can be operated by an electroporation unit and an IPH unit respectively in a sequential manner. More specifically, two caliper electrodes can be disposed on either side of a skin fold (e.g., electrodes 1 and 2 on the left side and electrodes 3 and 4 on the right side). In electroporation mode electrode 1 is pulsed against electrode 2, likewise electrode 3 is pulsed against electrode 4. In IPH mode, electrode 1 is connected to electrode 2 (with either positive or negative polarity) while electrode 3 is connected to electrode 4 with an opposite polarity; then electrodes 1 and 2 will be pulsed against electrodes 3 and 4. Of course, these operation parameters can be set or programmed into the mini-generator.

A vibration unit also can optionally be included in the apparatus, which can be used in combination with an electrical impulse to transdermally introduce a composition into and/or across the skin, if desired. A phonophoresis unit, which can transdermally introduce a composition into the skin by means of ultrasound, also can optionally be included in the apparatus, if desired. Thus, by applying vibration or ultrasound before, after or during pulsing and/or iontophoresis, the composition can be driven deeper into the target tissue or a greater amount of the composition can be driven into the target tissue than pulsing alone. As above, a switching unit, such as an automated switch, optionally programmable, could be used to control the time between applying the impulse and applying vibration or ultrasound, as well as optionally controlling the time during which impulse, vibration or ultrasound is applied A means for administering a composition can optionally be included in the electrical apparatus, which can be used to administer the composition to the target tissue prior to, substantially contemporaneously with, or after applying an electric pulse, iontophoresis, vibration or ultrasound, in their various embodiments. Depending on the specific formulation, a composition can be incorporated into a patch reservoir (e.g., as a nicotine patch), which is then attached both to the electrode and the skin. Formulations employed for IPH are advantageously used in this manner.

As used in the above context, the term "substantially contemporaneously" means that the electric pulse and the composition are applied to the skin reasonably close together in time. Preferably, the composition is administered prior to or concurrently with electropulsing. When applying multiple electrical impulses, the composition can be administered before or after each of the pulses, or at any time between the electrical pulses. When applying any auxiliary electrically-based therapy (i.e., IPH, EI, and the like), vibration or ultrasound, the composition can be administered before or after each, and at any time between.

Although electrodes of the invention are designed to work with commercially available electroporation power supplies, the invention apparatus can have a variety of other functionalities in addition to the optional controlling means for applying an electric pulse, indicating means and fastening means. For example, the apparatus can have an indicating means for indicating apparatus ready, the various pulse parameter settings (e.g., voltage, capacitance, pulse duration, time delay between pulses, pulse wave type), pulse(s) applied, parameters of the applied pulse(s) (e.g., voltage, capacitance, pulse duration, pulse wave type, number of pulses) or a combination thereof. Such indicating means can be visual, audible, or a combination thereof. For example, a single audible "beep" can indicate that the "apparatus is ready," two audible "beeps" can indicate that a pulse has been correctly applied and three audible "beeps" can indicate a malfunction or that the pulse was not or was improperly applied. Visual indicating means include analog or digital alpha-numeric displays (e.g., LCD, LED and the like), as in watches, and further can include illuminating means for low light visualization, for example, by white light, electroluminescent backlighting for LCD or electroluminescent lamps (i.e., INDIGLO™), or by various fluorescent or radioactive illuminating compositions, and the like.

Additional "user friendly" functions include the aforementioned controlling means for applying an electric pulse (e.g., pushbutton, knob, lever switch, dial and the like) as well as means for adjusting parameters (e.g., pushbutton, knob, lever switch, dial and the like) including, for example, pulse duration, voltage, capacitance, field strength, number, wave type, and the like. Means for adjusting, setting, storing or retrieving one or more pulse parameters also are included herein. Such means include traditional mechanical electronic controls (e.g., a selector switch controlling each parameter in which the switch has a plurality of settings; exemplary pulse length settings, 5 ms, 10 ms, 25 ms, 35 ms, 50 ms, for example) as well as a chip control (e.g., silicon wafer types commonly used in the computer industry) which is controlled, for example, by a pushbutton interface, as in watches for example. A chip, optionally removable from the apparatus or, user and/or manufacturer programmable for control of the various pulse parameters set forth herein also is contemplated. Storage capacity of such a chip is sufficient to provide virtually unlimited fine control of the various parameters, as well as storing different pulse parameter settings for different compositions, users and the like. As each of the various electronic functionalities of the invention apparatus described herein can be controlled or managed by a computer chip, a chip affords the option of additionally incorporating software, if desired, said software optionally user programmable.

In addition to efficacy, both sensation and user safety are important. Thus, in another embodiment, the invention further provides an apparatus having means for preventing applying excess pulse voltage, duration, field strength and/or number. Any means which passively or actively interrupts or disrupts the electric circuit, including fuses, circuit breaker switches, and the like, or devices that actively monitor the various pulse parameters and interrupt or disrupt the electric circuit to prevent excess pulse voltage, duration, field strength, pulse number from being applied can be incorporated into the circuit path. Those skilled in the art of electrical devices will know of other protective elements that prevent applying excess pulse voltage, duration, field strength or number.

The electric pulse can be provided by any electronic device that provides an appropriate electric pulse or electric source sufficient for transdermally introducing a composition into skin and/or muscle. The nature of the electric field to be generated is determined by the nature of the tissue, the size of the selected tissue and its location. It is desirable that the field be as homogenous as possible and of the correct amplitude. Excessive field strength results in lysing of cells, whereas a low field strength results in reduced efficacy. The electrodes may be mounted and manipulated in many ways including but not limited to those in the parent application. The electrodes may be conveniently manipulated on and by forceps to internal position.

The waveform of the electrical signal provided by the pulse generator can be an exponentially decaying pulse, a square pulse, a unipolar oscillating pulse train, a bipolar oscillating pulse train, or a combination of any of these forms. The nominal electric field strength can be from about 10 V/cm to about 20 kV/cm (the nominal electric field strength is determined by computing the voltage between electrode needles divided by the distance between the needles). The pulse length can be about 10 $\mu$s to about 100 ms. There can be any desired number of pulses, typically one to 100 pulses per second. The wait between pulses sets can be any desired time, such as one second. The waveform, electric field strength and pulse duration may also depend upon the type of cells and the type of molecules that are to enter the cells via electroporation. Each pulse wave form has particular advantages; square wave form pulses provide increased efficiencies in transporting compounds into the cells in comparison to exponential decay wave form pulses, and the ease of optimization over a broad range of voltages, for example (Saunders, "Guide to Electroporation and Electrofusion," 1991, pp. 227–47). Preferably, the waveform used is an exponential or a square wave pulse.

The electric fields needed for in vivo cell electroporation are generally similar in magnitude to the fields required for cells in vitro. Presently preferred magnitudes are in the range of from 10 V/cm to about 1300 V/cm. The higher end of this range, over about 600 V/cm, has been verified by in vivo experiments of others reported in scientific publications.

The nominal electric field can be designated either "high" or "low". It is presently preferred that, when high fields are used, the nominal electric field is from about 700 V/cm to 1300 V/cm and more preferably from about 1000 V/cm to 1300 V/cm. It is presently preferred that, when low fields are used, the nominal electric field is from about 10 V/cm to 100 V/cm, and more preferably from about 25 V/cm to 75 V/cm. In a particular embodiment of the invention, it is presently preferred that when the electric field is low, the pulse length is long. For example, when the nominal electric field is about 25–75 V/cm, it is preferred that the pulse length is about 10 ms.

In one embodiment of the invention, the therapeutic methods of the invention are practiced using an invention electrode apparatus for the application of electroporation to a portion of the body of a patient comprising a support member, a plurality of needle electrodes mounted on said support member for insertion into tissue at selected positions and distances from one another, and means including a signal generator responsive to said distance signal for applying an electric signal to the electrodes proportionate to the distance between said electrodes for generating an electric field of a predetermined strength.

Alternatively, it is understood that other systems could be utilized in the therapeutic method of the invention (e.g., for low voltage, long pulse treatment), for example, a square wave pulse electroporation system. Exemplary pulse generators capable of generating a pulsed electric field include, for example, the ECM600, which can generate an exponential wave form, and the ElectroSquarePorator (T820), which can generate a square wave form, both of which are available from BTX, a division of Genetronics, Inc. (San Diego, Calif.). Square wave electroporation systems deliver controlled electric pulses that rise quickly to a set voltage, stay at that level for a set length of time (pulse length), and then quickly drop to zero. This type of system yields better transformation efficiency for the electroporation of plant protoplast and mammalian cell lines than an exponential decay system.

The ElectroSquarePorator (T820) is the first commercially available square wave electroporation system capable of generating up to 3000 Volts. The pulse length can be adjusted from 5 $\mu$sec to 99 ms. The square wave electroporation pulses have a gentler effect on the cells which results in higher cell viability.

The T820 ElectroSquarePorator is active in both the High Voltage Mode (HVM) (100–3000 Volts) and the Low Voltage Mode (LVM) (10–500 Volts). The pulse length for LVM is about 0.3 to 99 ms and for HVM, 5 to 99 $\mu$sec. The T820 has multiple pulsing capability from about 1 to 99 pulses.

Additional electroporation type apparatus are commercially available and can be used to generate the pulse for the invention apparatus and in practicing the invention methods.

It has further surprisingly been discovered that histopathological change resulting from introduction of an electric field into muscle tissue can be reduced by careful selection of pulsing parameters and that reduction in histopathological change in target tissue, especially histopathological change associated with the induction or amplification of an immune response not only is more comfortable for the subject, but provides additional therapeutic benefits as well when the invention methods are used to deliver a therapeutic agent into cells of the muscle tissue.

Common indicators of histopathological change in muscle tissue include such well known conditions as muscle inflammation, muscle necrosis and muscle fibrosis. Therefore, the term "change associated with the induction or amplification of an immune response" as used herein refers to at least one or more of such conditions as muscle inflammation, muscle necrosis, muscle fibrosis, and the like. Such histopathological changes are conveniently measured using techniques well known in the art, such as microscopic examination of thin tissue samples stained to highlight various features of interest. For example, Example 13 herein describes preparation of Hematoxylin and Eosin (H&E) stained tissue samples in which necrotic muscle fibers stain light compared to healthy fibers. A representative protocol for preparation of muscle sections using H &E staining of muscle tissue is as follows:

| 1.  | 100% alcohol              | 2 × 5 min.  |
|-----|---------------------------|-------------|
| 2.  | 95% alcohol               | 2 min.      |
| 3.  | Tap water                 | 5 min.      |
| 4.  | Harris' Hematoxylin       | 4 1/2 min.  |
| 5.  | Tap water                 | 5 min.      |
| 6.  | 1% acid alcohol           | 5 dips      |
| 7.  | Tap water                 | 5 min.      |
| 8.  | Lithium carbonate (sat.)  | 2 min.      |
| 9.  | Tap water                 | 5 min.      |
| 10. | Eosin Y & B Philoxine     | 2 min.      |
| 11. | Tap water                 | 10 dips     |
| 12. | 70% alcohol               | 10 dips     |
| 13. | 95% alcohol               | 15 dips     |
| 14. | 100% alcohol              | 2 × 2 min.  |
| 15. | Xylol                     | 2 × 2 min.  |
| 16. | Mount                     |             |

Those of skill in the art will be familiar with alternative procedures for performing staining of muscle tissue for histopathological evaluation.

Muscle biopsy is conveniently performed under local anesthesia. Muscle fibers are subdivided into two types which have different staining characteristics: Type 1 fibers (fatigue-resistant and rich in oxidative enzymes) and type 2 fibers (fast-contracting, fatigue-prone, and rich in glycolytic enzymes). Normal muscle has a random distribution of fibers of the two histochemical types.

The terms "muscle necrosis" and "necrosis" as used herein refer to a condition caused by damage of the sarcolemma of the muscle fiber, which allows entry of calcium at high extracellular concentration into the low-calcium environment of the sarcoplasm. Calcium entry activates a neutral protease, initiating proteolysis. Calcium also poisons mitochondrial function and can cause cell death. Invading macrophages phagocytize the muscle fibers. Thus, a diagnosis of muscle necrosis that identifies infiltrating macrophages, loss of mitochondrial function and/or cell death is an indicator of muscle necrosis. Necrotic muscle fibers are easily distinguished from regenerating muscle fibers produced by satellite cells, which proliferate and fuse to produce multinuclear myotubes leading to regeneration of the muscle fiber. Characteristically, regenerating fibers are small, and basophilic owing to an increased concentration of RNA, and have large vesicular internalized nuclei.

The terms "skeletal muscle fibrosis" "muscle fibrosis" and "fibrosis" as used herein refer to a phenomenon that frequently occurs in diseased or damaged muscle. It is characterized by the excessive growth of fibrous tissue, and impairs muscle function. The amount of muscle function loss generally increases with the extent of fibrosis. A number of methods are available to determine the state of skeletal muscle fibrosis in a muscle biopsy sample, including evaluating a muscle tissue biopsy from the subject by histochemical or immuno-histochemical stains that can detect fibrotic tissue. Examples of such histochemical stains include, for example, hematoxylin and eosin (H & E), trichrome and ATPase (at pH 4.3, 4.65 and 10.4). Representative antibodies that can be used to label muscle fibers for immuno-histochemical staining include, for example, those against myosin, type IV collagen, laminin, and fibronectin.

The terms "muscle inflammation" and "inflammation" as used herein refer to the inflammatory process at it applies to muscles, such as skeletal muscle. Inflammation is a fundamental pathologic process involving complex reactions that occur in the affected blood vessels and adjacent tissues in response to the procedures involved in generating an electric field in muscle tissue. An acute inflammatory response is characterized by changes that take place in the microvasculature (arterioles, capillaries, and venules) and the interstitial areas (fluid-filled regions between cells and tissues). These include changes in vascular flow and caliber, changes in vascular permeability, and leucocyte exudation. The first change involves vasodilation of the vessels and increased blood flow. The second change involves increased permeability of the blood vessels with a movement of fluid and proteins out of the vessels creating edema of the tissues. The final change occurs as white blood cells infiltrate and accumulate in the surrounding tissue.

The spread of the acute inflammatory response following injury to a small area of tissue suggests that chemical substances are released from injured tissues, spreading outwards into uninjured areas. These chemicals, called endogenous chemical mediators, cause vasodilation, emigration of neutrophils, chemotaxis and increased vascular permeability. Histamine is a chemical mediator in acute inflammation and causes vascular dilatation and vascular permeability. It is stored in mast cells, basophil and eosinophil leucocytes, and platelets. Histamine release is stimulated by complement components C3a and C5a and by lysosomal proteins released from neutrophils. Prostaglandins are a group of long-chain fatty acids derived from arachidonic acid. Such factors associated with the induction or amplification of an immune response increase vascular permeability, and platelet aggregation.

Muscle inflammation can be conveniently measured, for example, using commercially available computer imaging software to calculate the % area of mononuclear infiltrating cells in a standard 2.5 mm square sample of tissue.

Accordingly, in yet another embodiment, the invention provides methods for reducing inducement of histopathological change in a target muscle tissue site resulting from application of an electric field to a subject in need thereof, said method comprising generating an electric field at the target muscle tissue site of the subject by introducing from 1 to about 4 monopolar DC pulses, for example, 1 or 2 such pulses, each pulse having a duration of about 10 ms to about 100 ms, for example a duration of about 40 ms to about 60 ms, or of about 20 ms to about 60 ms. The DC pulses applied to the subject are used to generate a nominal electric field at the target muscle tissue site of about 100V/cm to about 300V/cm. For example nominal electric fields of about 100 V/cm to about 232 V/cm or of about about 100 V/cm to about 150 V are suitable for use in the invention methods to reduce inducement of histopathological change in the target tissue resulting from application of an electric field. The studies described in Example 13 below indicate that no more than two pulses used at each target muscle tissue site may be the most effective for reducing histopathological muscle change in the subject.

The invention methods for reducing the inducement of histopathological change in a target muscle tissue site resulting from application of an electric field to a subject can be used for introducing at least one therapeutic agent into the target muscle tissue site. As with other embodiments of the invention, the agent can be any type of drug, chemical, polypeptide or polynucleotide, especially those with a therapeutic or cosmetic purpose for the benefit of the subject. It has been discovered in this connection that the pulse parameters and nominal electric field strength described herein as effective for reducing inducement of histopathological change in muscle tissue are also effective for enhancing gene expression, for example in gene therapy applications. In this aspect of the invention, the isolated polypeptide is introduced at substantially the same time as the electric field is generated so as to result in the polynucleotide entering cells of the target muscle tissue for expression of the therapeutic polypeptide therein. The polynucleotide can advantageously be injected into muscle tissue at the treatment site at from 1 to about 20 locations.

Thus by introducing an effective amount of at least one isolated polynucleotide encoding a therapeutic polypeptide into a target muscle tissue and applying an electric field as described herein, expression of the encoded therapeutic polypeptide is greatly enhanced as compared to expression of the therapeutic polypeptide achieved by other methods for generating an electric field in the target muscle tissue. However, the invention pulse parameters described herein as effective for reducing inducement of histopathological change in muscle tissue are not effective in the case where the polynucleotide encodes an immunogenic peptide with the goal of inducing an immune response in the subject. For induction of an immune response, it may be beneficial to employ pulsing parameters other than those that reduce histopathological change in muscle tissue.

In one embodiment of the invention, to aid in reduction of histopathological response of muscle tissue to a process in which an electric field is generated therein, the electric field can optionally be generated by applying to the subject electroporation electrodes wherein a portion of the electrodes that contacts the subject is made of a non-toxic, biocompatible metal. The portion of the needle electrodes that contacts the healthy tissue can have a coating or plating over a shank of baser metal of the non-toxic, biocompatible metal. For example, the coating or plating can be of gold and have a mean thickness of at least 10 $\mu$m. Optionally, at least one of the electrodes used in the invention methods can be a hollow needle electrode so that a therapeutic agent, such as a polypeptide, small molecule or polynucleotide, can be introduced into the subject via the hollow needle electrode.

Although certain aspects of the invention are described with respect to the preferred use of gold needles, those of skill in the art will understand that needles fashioned from any metal or metal containing material having material properties similar to gold, such as electrical conductivity and the like, and which can be introduced into tissue without resulting in a toxic condition or causing discoloration of the tissue also are preferred for use as the needle electrodes in the place of the gold needles. The use of non-toxic, biocompatible metal for one or more of the electrodes, especially when needle electrodes are used, avoids the risk of depositing a contaminating metal or a contaminating amount of metal in the tissue, such as results when electrodes made of baser metals, such as stainless steel are used.

Relatively low pulse number, voltage and pulse length ease potential anxiety of patients and reduce pain and muscle contractions from the electrical pulse(s). Minimizing inflammation makes EP for gene therapy safer since it reduces the possibility of interfering with the corresponding protein therapy or generating as yet unspecified immune complications.

It has further been surprisingly discovered that in methods of delivering DNA, at concentrations from about 0.1 $\mu$g to about 10 $\mu$g, to skin tissue using noninvasive electrodes, application of one to about two electric pulses to the electrodes generally induces an appropriate electric field as effectively as does application of more than two electric pulses. Accordingly, in yet another embodiment, the invention provides in vivo methods for enhancing expression of a therapeutic polypeptide encoded by an isolated polynucleotide to be delivered into skin cells in vivo in a subject, by:
a) introducing about 0.05 $\mu$g to about 100 $\mu$g per skin tissue site of at least one isolated polynucleotide encoding a therapeutic polypeptide into one or more skin tissue sites of a subject;
b) applying at least two non-invasive electrodes to the skin tissue site;
c) generating a total charge transfer at the skin tissue site of about one mCoulomb (mC) to about 1000 mC per skin tissue site by introducing one or more electric pulses to generate said total charge transfer at the skin tissue site, at substantially the same time as the introduction of the polynucleotide so as to result in the polynucleotide entering cells of the skin tissue for expression of the therapeutic polypeptide therein;
thereby enhancing the expression of the therapeutic polypeptide as compared to expression of the therapeutic polypeptide achieved by other methods for generating an electric field in target skin tissue. For example the total charge transfer at the skin tissue site can be about 10 mC/cm$^2$ to about 20 mC/cm$^2$; wherein about 0.1 $\mu$g to about 10 $\mu$g per skin tissue site of the polynucleotide is introduced. In this method, when the electrodes are non-invasive electrodes, the preferred electroporation parameters are as follows:

For a meander electrode, for example one wherein distance between electrodes in the meander electrode is about 0.2 mm, the total charge transfer (O) is generated by applying the one or more electric pulses at a voltage of about 40 V to about 100 V to the electrodes. Each electric pulse is applied for a period of about 1 ms to about 100 ms and frequency of the electric pulses is about 1 to about 10 Hz.

For a caliper electrode, the total charge transfer is preferably generated by applying the one or more electric pulses so as to cause a nominal field strength in the skin site of about 200 V/cm to about 2500 V/cm. Each electric pulse is applied for a period of about 0.1 ms to about 100 ms and frequency of the electric pulses is about 1 Hz to about 10 Hz. From one to about 30 of the electric pulses are applied.

With either type of non-invasive electrode, resistance of the stratum corneum in the skin site can be reduced prior to generating the charge transfer at the skin tissue site by a procedure selected from laser treatment, tape stripping, electroporation, ultrasound, penetration enhancing chemicals, and any combination thereof, and wherein the isolated polynucleotide is applied topically to the skin tissue site.

As in other embodiments of the invention electroporation methods, in the methods for introducing DNA into skin, as described herein, the subject can be a mammal, for example, a human. The polynucleotide is selected from double stranded DNA, single-stranded DNA, complexed DNA, formulated DNA, encapsulated DNA, naked RNA, encapsulated RNA, and combinations thereof. The polynucleotide encoding the therapeutic polypeptide is optionally contained in a DNA vector and operably associated with a regulatory sequence for expression of the therapeutic polypeptide in cells, such as a promoter. Suitable promoters include CMV, RSV LTR, MPSV LTR, and SV40 promoters. A preferred promoter is skin cell specific. The polynucleotide may further encode a selectable marker polypeptide.

As shown in Example 14, a single electroporation (EP) pulse was sufficient to increase luciferase activity 340 times over DNA injection without EP (P<0.0005) and was as effective as multiple pulses. Meander and caliper electrodes yielded equivalent levels of luciferase expression under the conditions tested (P<0.11). However, flat meander electrodes are more patient-friendly for potential clinical applications compared to caliper-type electrodes, which require pinching of a skin-fold. Effective gene delivery to skin using fewer electric pulses than previously thought necessary, provides greater comfort to the subject and minimizes the potential for tissue damage, which is a risk that increases with increased application of electric charge to tissue.

It was discovered that efficient gene delivery can occur over a wide range of electroporation conditions so long as the total charge and electric field strength applied to skin tissue remain constant. Thus, the number and duration of electric pulses applied to electrodes in contact with skin can vary within a wide range so long as the conditions result in an effective total charge and electric field strength. Thus, as shown in Example 14 and Table 7, the voltage applied to non-invasive electrodes in contact with tissue to deliver DNA amounts of 0.1 or 10 $\mu$g per skin tissue target site was varied between 50 V and 100 V, the pulse length was varied between 2 and 30 ms, the number of pulses was varied between 3 and 30, and the frequency of pulse delivery was varied from 1 to 10 Hz. So long as the various combination of electroporation parameters resulted in the same charge transfer, Q, namely 12 mCoulomb (mC), efficient gene transfer could be achieved. The total charge (O) delivered by each EP protocol was calculated using equation (1):

$$Q = I \times t \times N = (V/R) \times t \times N \qquad (1)$$

where I is the current in Amps, V is the applied voltage in Volts, t is the pulse length in seconds, N is the number of pulses, and R is the skin impedance in Ohms during the electroporation.

A preferred protocol for use in electroporation-mediated delivery of nucleic acid to skin tissue using non-invasive electrodes is to introduce DNA, at amounts of about 0.1 $\mu$g to about 10 $\mu$g per delivery site into the tissue, apply non-invasive electrodes to skin, apply electric charge to the electrodes to achieve a total charge transfer of from about one mC to about 100 mC. In a preferred embodiment, the total charge transfer is about 10 mC to about 20 mC. Examples of electric charge parameters that can be used in the method of the invention include those parameters set forth in Table 7. An especially preferred set of parameters comprises application of 1–2 electric pulses to the electrodes, at 75 V, 10 Hz, with no reversal of polarity. Preferred electrodes for delivery of nucleic acid to skin are meander and caliper electrodes.

In one embodiment of the invention, prior to application of the charge to the skin, the skin is pretreated to reduce resistance of the stratum corneum using any method known in the art, for example, laser treatment, tape stripping, electroporation, ultrasound, penetration enhancing chemicals, and the like, and any combination thereof. This procedure is particularly beneficial when the polynucleotide is applied topically to the skin tissue site and the electroporation method is non-invasive as described herein. The invention will now be described in greater detail by reference to the following, non-limiting examples.

EXAMPLES

Example 1

Electroporation of LacZ DNA

LacZ DNA (40 μg DNA in 20 μl Tris-EDTA), wherein the lacZ gene is under control of the CMV promoter, was topically applied to the skin of six to seven-week-old SKH1 hairless mice (female) (Charles River Laboratories. Wilmington, Mass.). A caliper electrode (FIG. 10A) was then placed on both sides of a skin-fold at the dorsal region of the mouse and electrical pulses were delivered. Unpulsed mice were used as pressure-only and blank controls. The skin was harvested for X-gal staining 3 days after application of the lacZ DNA.

Pulse application and electrical measurements: Three exponential decay pulses of amplitude 120 V and pulse length of 10 ms or 20 ms were administered from a BTX ECM 600 pulse Generator within about 1 minute. Pressure was maintained with the caliper for up to 10 min. following pulsing. A caliper-type electrode (1 cm$^2$ each electrode) was applied on a mouse skin-fold of about 1 mm in thickness. Resistance of the skin was measured before, during and after pulsing. Expression of lacZ DNA was assayed by X-gal staining with 0.1% nuclear fast red. Standard histological analysis was then carried out.

Figure 14A:
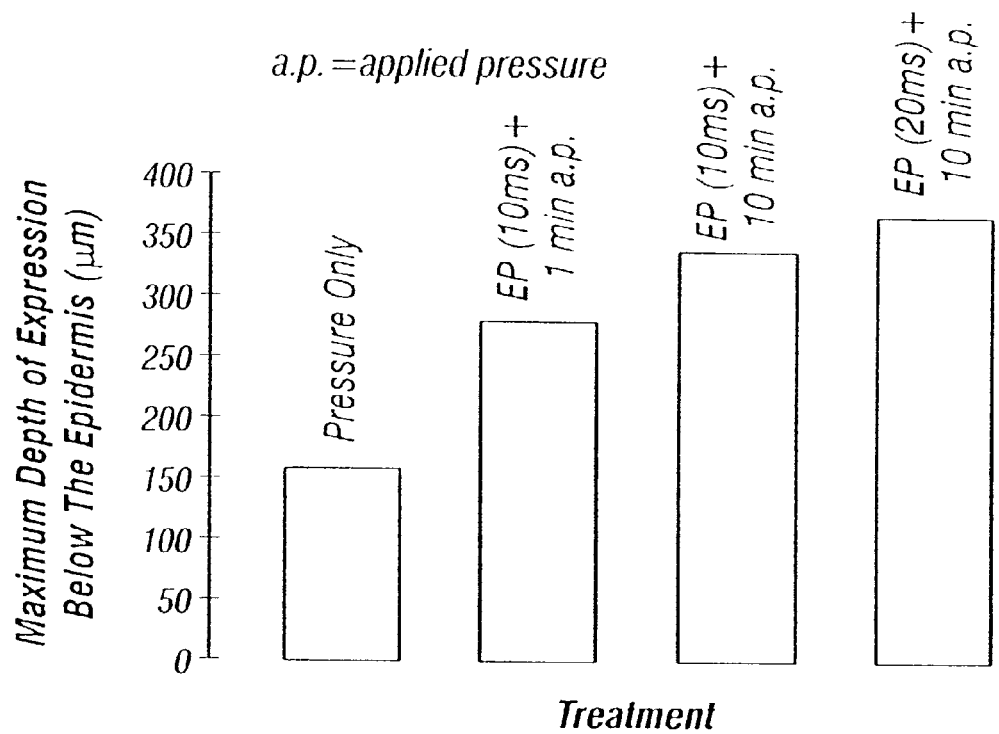
FIG. 14A graphically depicts the depth of lacZ gene expression under the experimental conditions described for FIG. 13 (a–d).
Figure 14B:
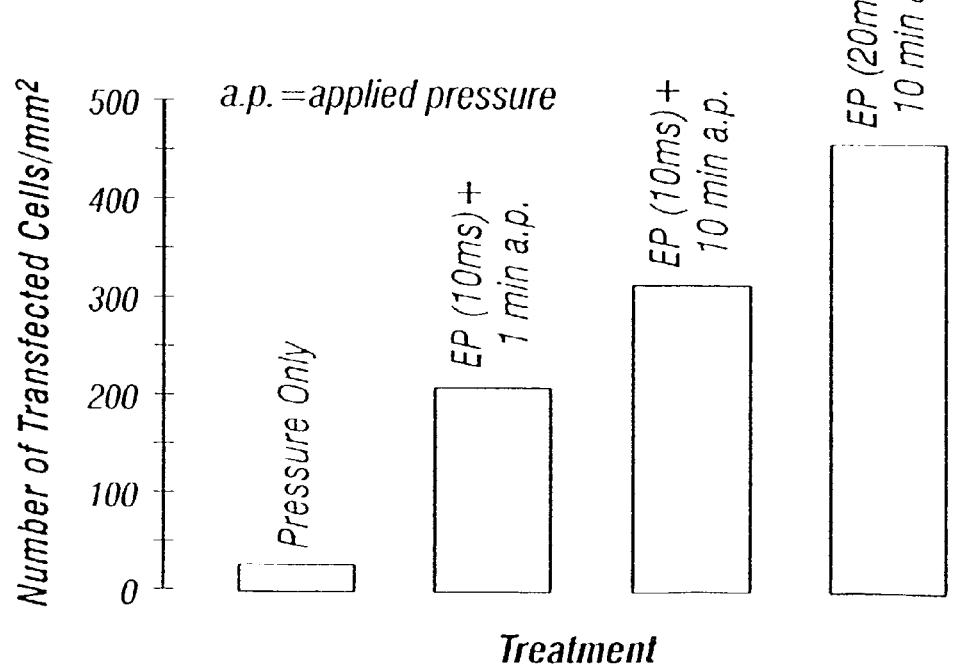
FIG. 14B graphically depicts the transfection efficiency of lacZ gene under the experimental conditions described for FIG. 13 (a–d).

Results: Typical results of gene expression after 3 days are shown in FIG. 13 (a–d). A cell that expresses the lacZ gene undergoes blue staining of its cytoplasm when exposed to X-gal. Efficient gene transfer and expression were found in the dermis by pulsing and pressure treatment for 1 min. (FIG. 13b, FIGS. 14A and B). In the case of control (pressure only by caliper electrode), gene expression appeared only around hair follicles in the very upper layers of the skin with light blue staining (FIG. 13a, FIGS. 14A and B). This indicates that the electrical pulse creates new pathways to permit passage of DNA through the epidermis. Pressure maintained after the pulses, increases the depth as well as the efficiency of gene expression in the dermis. See, for example FIG. 13c, wherein a pulse of 10 ms delivered over about 1 min. was followed by caliper pressure being maintained for about 10 min. The third bar on graphs 14 A and B show depth of penetration and efficiency of transfection, respectively, for the same parameters. A greater number of transfected cells and more intense lacZ gene expression were found with a 20 ms pulse length (FIG. 13d and FIGS. 14A and B, fourth bar, compared to 10 ms. The maximum depth of lacZ gene expression below the epidermis with pressure maintained for 10 minutes after pulsing was more than twofold that of the control in the hair follicles only.

The in vivo resistance measurements have demonstrated that the high resistance of the SC decreased dramatically during electroporation, and the recovery time (i.e., recovery of original resistance) depends on the electrical parameters. No β-gal activity was found in the control groups such as: no lacZ, pulse (i.e., electroporation); no pulse, lacz, no lacZ or pulse. There was no evidence of tissue injury in the pulsed skin by visual observation as well as in histological studies.

Example 2

Electroporation of GFP

Figure 15:
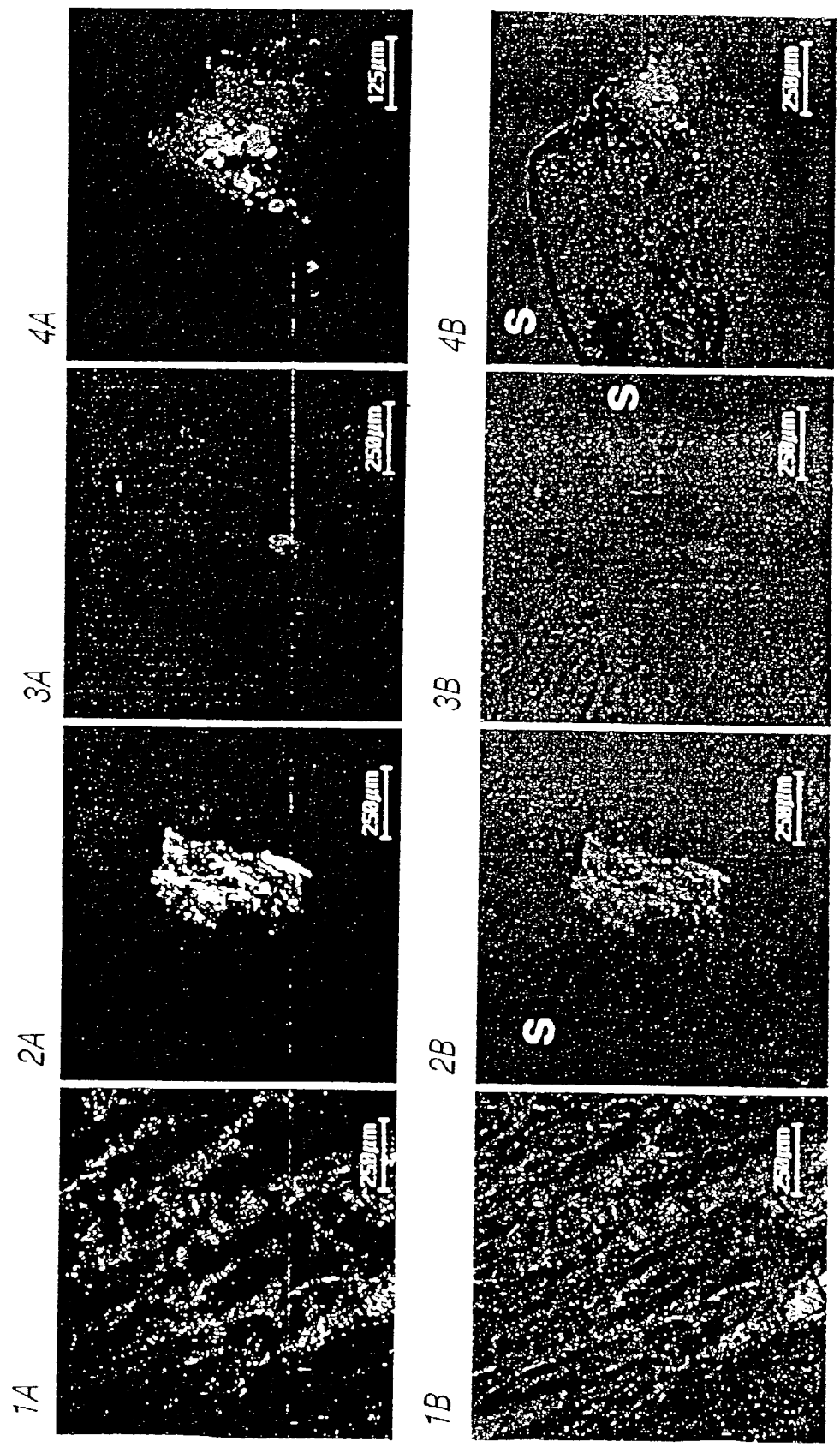
FIG. 15, panels 1 A/B–4 A/B show photomicrographs comparing integration and expression of GFP following application of plasmid DNA containing the GFP gene, followed by electroporation using meander or caliper type electrodes.

In vivo skin-targeted GFP gene delivery (FIG. 15): A procedure similar to that used in Example 1 was used for investigation the effectiveness of GFP expression in skin. Hairless mice were anesthetized with isoflurane inhalation and their dorsal hindquarter skin was swabbed with alcohol and air-dried. Fifty micrograms of a plasmid containing GFP and associated regulatory sequences (CMV promoter) was either applied topically or directly injected into the skin followed by electroporation with the caliper electrode or meander electrode. The animals were sacrificed three days later and skin of the treated area was excised and frozen. Frozen cross sections (12 μm) were immediately prepared. Viewing under a microscope with confocal fluorescent optics and FITC filtration, indicated GFP expression in the epidermal and dermal layers of the relatively thin murine skin (FIG. 15). The results of several different treatment regimens are depicted in FIG. 15. Panels 1A and 1B of FIG. 15 show photomicrographs of direct injection into abdominal muscle of plasmid. Panels 2 A/B and 3 A/B of FIG. 15 show the results of topical application of plasmid followed by three 100 V, 20 ms pulses applied using the BTX ECM 600 generator, using a caliper electrode (2 A/B) or a meander electrode (3 A/B). Panels 4 A/B of FIG. 15 show the results of subcutaneous injection of plasmid followed by three 120 V, 20 ms pulses applied using the BTX ECM 600 generator, using a caliper or meander electrode. Both the topical application and dermal injection of DNA gave detectable GFP expression with little apparent difference in the level of activity.

Example 3

In Vitro Electroporation Of Human Glioblastoma Cell Line SF-295

Figure 16A:
FIGS. 16A and 16B depict photomicrographs using confocal fluorescent optics and FITC filtration of SF-295 cells 24 hours post electroporation with 30 µg of unlabeled and 10 ug of TOTO-1 labeled plasmid, each encoding GFP.
Figure 16B:

To evaluate and track the delivery of plasmid DNA to target cells, a fluorescently labeled vector using TOTO-1 (Molecular Probes, Inc.) was developed. The TOTO-1 molecule is attached to the green fluorescent protein (GFP)-expressing vector pEGFP-C1 (Clonetech). Both the plasmid, and the plasmid product (GFP) fluoresce under the same FITC excitation and filtration, and are thus both observable simultaneously under a microscope with confocal fluorescent optics and FITC filtration. (FIG. 16). 30 μg of unlabeled and 10 ug of TOTO-1 labeled plasmid was electroporated into the SF-295 cells and 24 hours later GFP expression was assessed through an inverted fluorescent microscope. In FIG. 16A, (100× magnification, fluorescent light only) GFP expressing cells are visible as well as small green fluorescent dots that indicate TOTO-1 labeled plasmid within cells that are not expressing the plasmid. In FIG. 16B, (460× magnification) white light from a tungsten source was added to the fluorescent light to simultaneously illuminate the GFP positive and negative cells. This image shows the TOTO-1 labeled plasmid is aggregated into subcellular vesicles but the cells have not yet expressed GFP. Thus, the intracellular delivery and expression of a plasmid vector can be evaluated by this technique for in vivo skin applications.

Example 4

DNA Uptake in the Skin

DNA encoding the firefly luciferase gene was injected intradermally into skin of hairless mice (no shaving) or rats (after shaving of fur). DNA amounts shown in Table 1 were injected in 50 µl PBS as shallow as possible into the skin, using a 30 gauge needle. Electroporation was done with a caliper electrode (1 cm$^2$) or with a Micro-patch II flat electrode. Where indicated, three 120V, 20 ms. pulses were given, using a BTX T820 instrument (BTX, Inc., San Diego, Calif.). The site of DNA injection was marked and the skin was removed 24 hours after treatment. Skin flaps were minced by scissor in lysis buffer provided in the commercial luciferase assay kit and luciferase activity was measured following the kit protocol. The results shown in Table 1 indicate that electroporation dramatically increases gene expression after intra-dermal DNA delivery into mouse and rat

TABLE 1

EP Enhancement of Lucerifase Activity after Intra-Dermal DNA Delivery (RLU)

|  | i.d. | i.d. + pulse |
|---|---|---|
|  | 20 µg in 50 µl | |
| Mice | 38 | 156,995 (caliper) |
|  | 7229 | 211,636 (caliper) |
|  | 1831 | 116,725 (micro-patchII) |
|  | 415 | 1,704,558 (micro-patchII) |
| Rat | 57 | 194,398 (micro-patchII) |
|  | 5 µg in 50 µl | |
| Mice | 160 | 49,247 (caliper) |
|  | 9,021 | 57,134 (caliper) |
|  | 879 | 46,264 (micro-patchII) |
|  | 116 | 36,679 (micro-patchII) | background: <50, with or without pulse

Example 5

DNA Uptake in the Muscle

DNA encoding the firefly luciferase gene (20 µg in 50 µl PBS) was injected into the hind-limb muscle of hairless mice using a two needle electroporation array, where the injection needle also serves as negative electrode. The distance between the two electrodes was 2 mm. Where indicated, six pulses were given (20V per mm electrode distance, 50 ms., reversed polarity after 3 pulses; one pulse every 15 seconds) using the BTX T820 instrument. After 4 hours, the treated muscle was removed and minced by scissor for determination of luciferase activity using a commercial kit.

Genes encoding human growth hormone (hGH) or secreted alkaline phosphatase (SEAP) were injected into the hind limb muscle of rats using the same device as used in mice and (where indicated) electroporation was done as described for mouse muscle. Growth hormone was measured in muscle tissue and serum using a commercial kit, SEAP activity was measured in serum using a commercial kit 24 hours after treatment. The results shown in Table 2 indicate that electroporation dramatically increases gene expression after intra-r muscular DNA delivery in mice and rats.

TABLE 2

EP Enhancement of Gene Expression in Muscle

|  | i.m. | i.m. + pulse |
|---|---|---|
| hGH in rats (20 µg in 50 µl) (RLU) | | |
|  | 3,341 | 41,465 |
|  | 3,462 | 27,540 |
| Serum | 1,027 | 1,449 |
| Background: muscle: | 3,242 | |
|  | 3,397 | |
| serum: | 952 | |
| Luciferase in mice (20 µg in 50 µl) (RLU) | | |
|  | 576 | 27,441 |
|  | 140 | 74,637 |
| Background: 50, 62 | | |
| SEAP in rats (20 µg in 50 µl) (RLU in serum) | | |
|  | 5,009 | 191,398 |
| Background: 2143 | | |

Example 6

Immune Responses After Intramuscular DNA Delivery

An example of a model antigen is the Hepatitis B Virus surface Antigen (HBsAg). The gene encoding this antigen was cloned into an eukaryotic expression vector so that expression of the sAg gene is driven by the human elongation factor I promoter. Expression was verified by transient expression in B16 cells.

DNA was injected into the gracialis muscle of the hind limbs of Balb/c mice: 50 µg DNA in 50 µl PBS, both hind limbs were injected. One cohort of four animals was injected only (animals #1–4 in Table 3), one other cohort was treated with a two needle electrode array and pulsed: 20V per mm needle distance, 2×3 pulses at 50 ms. with polarity reversion after the first set of three pulses (animals #5–8 in Table 3). Two weeks after DNA delivery, 1 out of 4 mice was anti-HBSAG positive in the non-EP treated cohort. All mice in the treated group were positive, pointing towards a positive effect of EP on the generation of an immune response. All mice were boosted four weeks post prime and tested again for antibody titers. The geometric mean titer (GMT) in the treated group was 193 mIU/ml, with ¾ mice having reached protective antibody levels. The GMT in the untreated group was 3.2 mIU/ml, with only one out of four mice reaching protective antibody titers. DNA immunization into the tibialis anterior muscle confirmed the above results: mice #1–4 in Table 4, untreated, GMT: 2.6 mIU/ml; mice #13-1 to 13-1, Table 3, EP treated, GMT: 13,547. In addition to showing the significant improvement of EP treatment on an immune response after DNA immunization, these data also show the superiority of the tibialis muscle for DNA immunization in mice.

Example 7

DNA Titration

To test whether electroporation could increase the efficiency of DNA vaccination after i.m. injection by allowing the use of lower DNA doses, DNA titration studies were performed. The need for extremely large doses of DNA is a major obstacle that has yet to be overcome in the DNA vaccination of larger animals than mice, and electroporation helps to overcome this problem. Except as otherwise noted, the experimental portions of this Example are as in Example 6.

Figure 17:
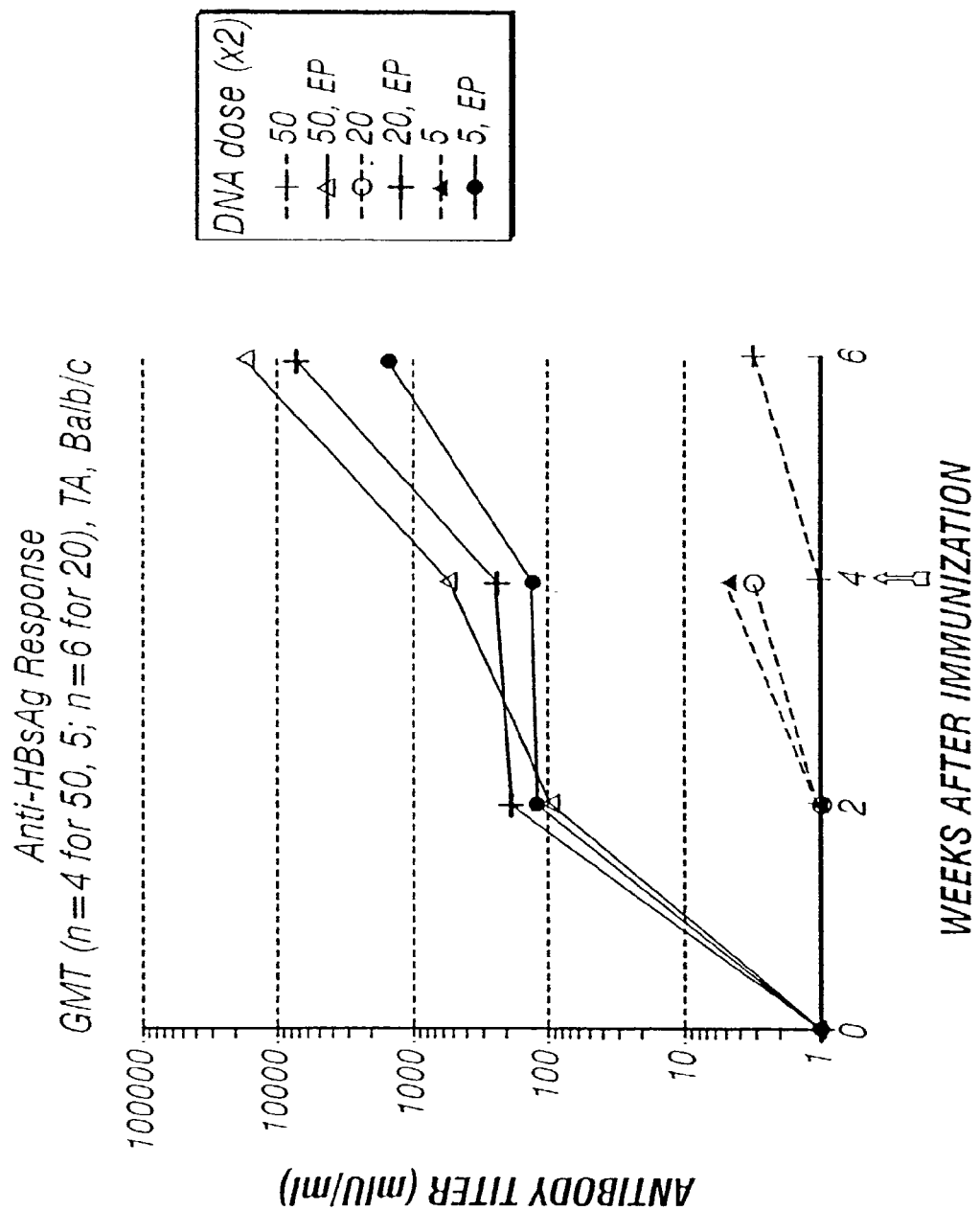
FIG. 17 graphically depicts the results of DNA immunization using 5 µg, 20 µg, and 50 µg in tibialis muscle of mice.

DNA immunizations with 5 μg, 20 μg, or 50 μg gave strong and consistent antibody responses two weeks after prime, which showed strongly boosted secondary responses after a booster immunization. These responses were achieved only with electroporation. (Mice #5–14, Table 4, #11, 12, Table 5, #13-1–13-4, Table 3). Down titration of the DNA amount used to immunize showed the consistent primary responses could be achieved with 3 μ of DNA. With this amount, a booster immunization was necessary to give better than protective levels in all animals of this cohort. Mice #1–5, Table 6). One microgram or less DNA was found to be insufficient to induce antibody responses, even after electroporation. (Mice #6–20, Table 6). Untreated cohorts receiving 20 μg or 5 μg of DNA showed GMTs of <10 mIU/ml (mice #1–10, Table 5). The results of DNA immunization using 5 μg, 20 μg, and 50 μg in tibialis muscle are summarized in FIG. 17.

TABLE 3

| cage 6–13 | | | | primary | | secondary |
|---|---|---|---|---|---|---|
| cage # | animal | μg DNA | pulse | 2 week | 4 week | 9 week |
| 6 | 1 | 50 | − | 300 | ∀ | 115 |
|   | 2 | 50 | − | 0 | 0 | 0 |
|   | 3 | 50 | − | 0 | 0 | 0 |
|   | 4 | 50 | − | 0 | 0 | 0 |
| 8 | 5 | 50 | + | 150 | 200 | 1680 |
|   | 6 | 50 | + | 40 | 0 | 0 |
|   | 7 | 50 | + | 140 | 120 | 581 |
|   | 8 | 50 | + | 280 | 560 | 1442 |
| 7 | 9 | 50 | ++ | 0 | 0 | 0 |
|   | 10 | 50 | ++ | 0 | 0 | 27 |
|   | 11 | 50 | ++ | 0 | 0 | 13 |
|   | 12 | 50 | ++ | 0 | 0 | 0 |
| 13 | 1 | 50 | + | 120 | 200 | 3868 |
|   | 2 | 50 | + | 310 | >>1000 | >>57000 |
|   | 3 | 50 | + | 40 | 240 | 17087 |
|   | 4 | 50 | + | 50 | 1000 | 8941 |

TABLE 4

| cage 14–17 | | | | primary | | secondary |
|---|---|---|---|---|---|---|
| cage # | animal | μg DNA | pulse | 2 week | 4 week | 6–8 week |
| 14 | 1 | 50 | − | 0 | 0 | 0 |
|   | 2 | 50 | − | 0 | 0 | 0 |
|   | 3 | 50 | − | 0 | ∀ | 0 |
|   | 4 | 50 | − | 0 | 0 | 50 |
| 15 | 5 | 50 | + | 200 | >>300 | 16000 |
|   | 6 | 20 | + | 105 | 80 | 2000 |
|   | 7 | 20 | + | 160 | >300 | 7800 |
|   | 8 | 20 | + | 160 | 320 | 2700 |
| 16 | 9 | 20 | + | 180 | 160 | 1800 |
|   | 10 | 20 | + | >300 | 300 | 23800 |
| 17 | 11 | 5 | + | 80 | 200 | 1500 |
|   | 12 | 5 | + | >300 | 140 | 1450 |
|   | 13 | 5 | + | 60 | 60 | 1100 |
|   | 14 | 5 | + | >300 | 120 | 900 |

TABLE 5

| cage 24–26 | | | | primary | | |
|---|---|---|---|---|---|---|
| cage # | animal | μg DNA | pulse | 2 week | 7 week | secondary |
| 24 | 1 | 20 | − | 0 | 0 |   |
|   | 2 | 20 | − | ∀ | 0 |   |
|   | 3 | 20 | − | ∀ | 55 |   |
|   | 4 | 20 | − | 0 | 0 |   |
| 25 | 5 | 20 | − | 0 | 0 |   |
|   | 6 | 20 | − | 0 | 0 |   |
|   | 7 | 5 | − | 0 | 22 |   |
|   | 8 | 5 | − | 0 | 10 |   |
| 26 | 9 | 5 | − | 0 | 0 |   |
|   | 10 | 5 | − | 0 | 0 |   |
|   | 11 | 5 | + | 160 | 315 |   |
|   | 12 | 5 | + | 170 | 154 |   |

TABLE 6

| DNA titration | | | | primary | | secondary |
|---|---|---|---|---|---|---|
| Cage # | animal | μg DNA | pulse | 2 week | 4 week | 5 week |
| 27 | 1 | 3 | + | 300 | 120 | 336 |
|   | 2 | 3 | + | 0 | 70 | 13.2 |
|   | 3 | 3 | + | 0 | 0 | 51 |
|   | 4 | 3 | + | 200 | 0 | 81.5 |
| 28 | 5 | 3 | + | 30 | 0 | 771 |
|   | 6 | 1 | + | 0 | 0 | 0 |
|   | 7 | 1 | + | 0 | 0 | 0 |
|   | 8 | 1 | + | 0 | 0 | 0 |
| 29 | 9 | 1 | + | 0 | 0 | 0 |
|   | 10 | 1 | + | 0 | 0 | 0 |
|   | 11 | 0.5 | + | 0 | 0 | <10 |
|   | 12 | 0.5 | + | 0 | 0 | <10 |
| 30 | 13 | 0.5 | + | 0 | 0 | 0 |
|   | 14 | 0.5 | + | 0 | 0 | 0 |
|   | 15 | 0.5 | + | 0 | 0 | <10 |
|   | 16 | 0.1 | + | 0 | 0 | 0 |
| 31 | 17 | 0.1 | + | 0 | 0 | 0 |
|   | 18 | 0.1 | + | 0 | 0 | 0 |
|   | 19 | 0.1 | + | 0 | 0 | 0 |
|   | 20 | 0.1 | + | 0 | 0 | 0 |

Example 8

Systemic Delivery of SEAP Plasmid DNA Via Electroporation to Nude Mouse Skin

Figure 18:
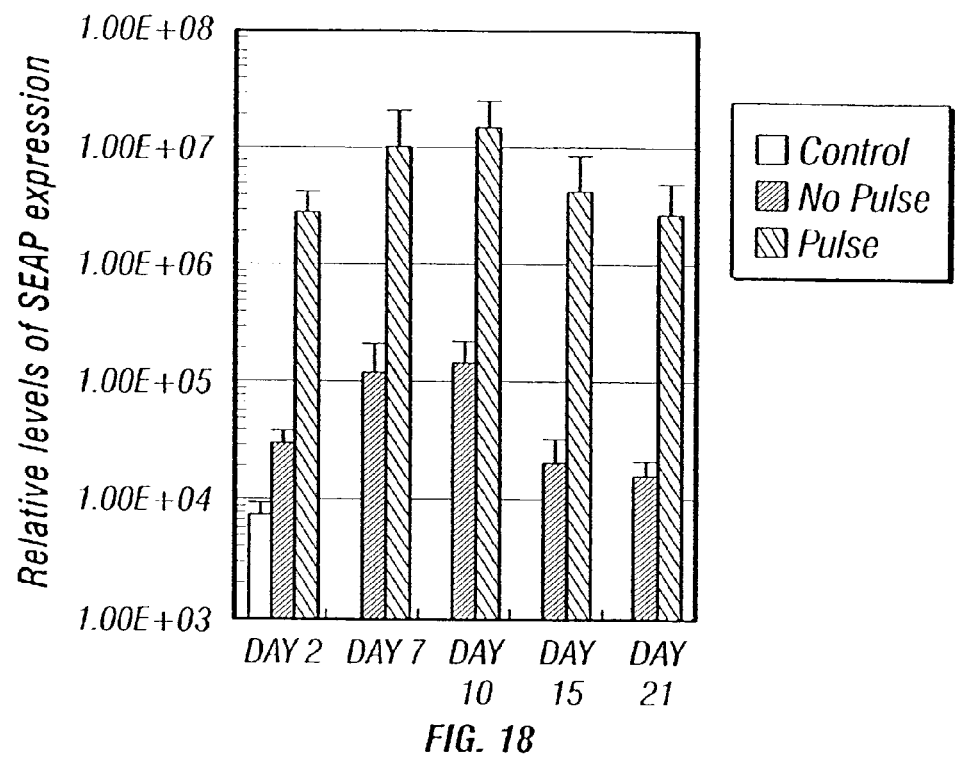
FIG. 18 depicts the dramatic increase in SEAP expression in blood obtained by combining electroporation with i.d. injection of plasmid encoding SEAP.

In order to demonstrate that naked DNA can be transfected into skin cells with resulting expression and systemic delivery of gene product, fifty micrograms of SEAP DNA (plasmid DNA wherein SEAP is driven by CMV promoter) in 1× PBS was injected i.d. into mouse flank followed by either electroporation or no electroporation. A square wave pulse at settings of 100V, 20 ms was applied using a meander electrode. Six pulses were applied with the polarity reversed after the first three pulses, and an interval of 100 ms between pulses. FIG. 18 shows that there is a dramatic increase in SEAP expression in blood that is greater than two logs. The length of expression is still high after 21 days in the nude mouse that is immune compromised.

Example 9

Figure 19:
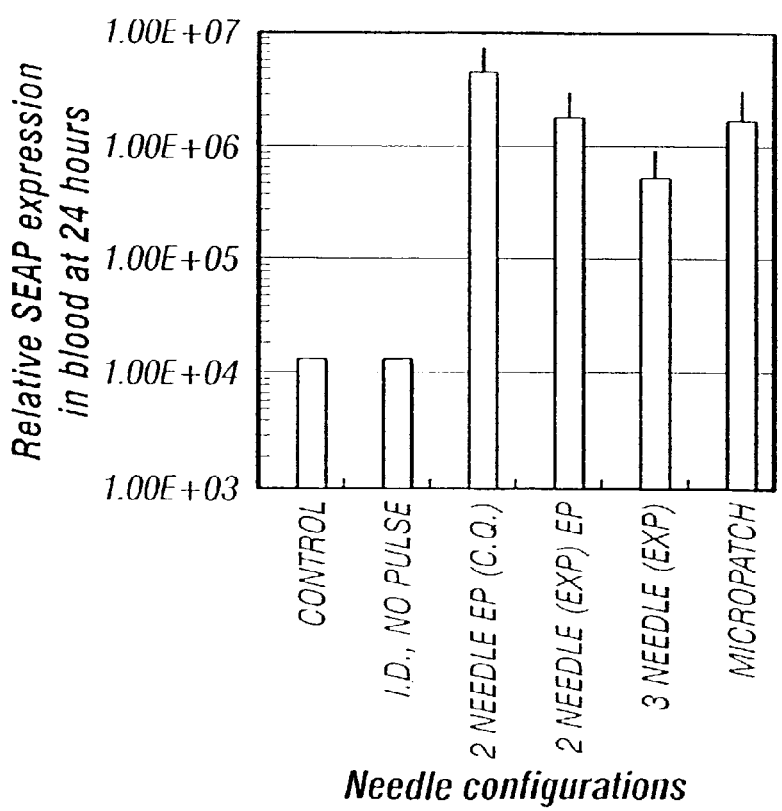
FIG. 19 graphically depicts the dramatic increases in SEAP expression in blood by using different configuration of shallow needle arrays when combining electroporation with i.d. injection of plasmid encoding SEAP.

Shallow Needle Array and Micropatch Deliver SEAP Plasmid DNA to Nude Mouse Skin In order to test the effectiveness of different electrode types, electroporation experiments were conducted using the shallow needle array depicted in FIG. 20 and the micropatch array described in U.S. patent application Ser. No. 08/905,240. Experimental conditions were as described in Example 8. FIG. 19 shows the dramatic increases in SEAP expression in blood by using different configurations of shallow needle arrays as well as the micropatch surface-type electrode. Square wave pulses were used with micropatch electrodes and 2-needle array (the higher bar in FIG. 19). The exponential pulses were used for 2- or 3 needle arrays (100 V, 20 ms, with polarity reversed after first three pulses). N=3 for micropatch and i.d. alone; n=2 for needle arrays; n=1 for control. Overall, electroporation again gave a two order of magnitude increase for SEAP expression. In the case of needle arrays (3 bars), only one needle injected DNA. However, DNA may be injected by more than one needle from the array.

Example 10

Figure 21:
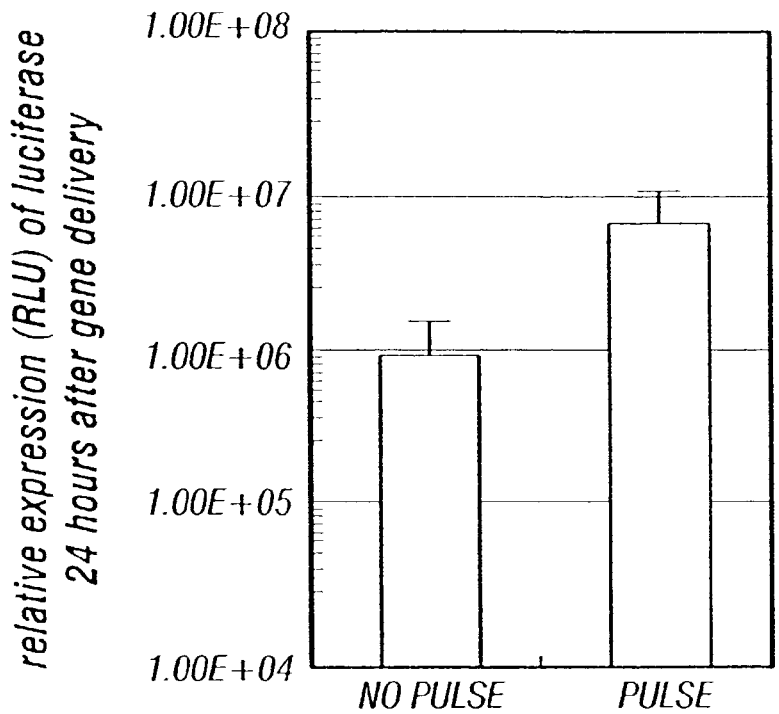
FIG. 21 shows the relative expression of luciferase (RLU) 24 hours after gene delivery to human skin xenografted onto nude mice, plus and minus electroporation.

Use of Caliper Electrodes to Deliver CMV-Luciferase Plasmid DNA to Human Skin Xenografted Nude Mice In order to demonstrate the capability of caliper electrode-based EPT to augment transfection of naked DNA into human skin (much thicker than murine skin), fifty micrograms of naked plasmid DNA containing the luciferase gene driven by the CMV promoter was i.d. injected into human skin xenografted onto nude mice. Luciferase expression was assayed 24 hours post DNA injection, plus and minus electroporation. Electroporation was as described in Example 8, employing a caliper electrode. The human skin grafts were excised from nude mice. The enzyme activity was measured by the spectrophotometer after homogenization and extraction. FIG. 21 shows the relative expression of luciferase (RLU) 24 hours after gene delivery. There was 7-fold increase for RLU in the pulsed group compared to i.d. injection alone.

Example 11

Comparison of Caliper vs. Meander Electrodes to Deliver CMV-Luciferase Plasmid DNA to Hairless Mouse Skin In order to evaluate the relative effectiveness of caliper v. meander type electrodes, each was tested as follows.

Mice were anesthetized by isoflurane inhalation, weighed, numbered with permanent ink, and swabbed with alcohol at the site of electroporation. The skin area treated by caliper electrodes was about 2 cm$^2$. 50 µg of naked plasmid DNA containing the reporter gene (luciferase driven by CMV promoter), at a concentration of 3.5 mg/ml in water, was administered onto the mouse skin. The DNA in solution, being slightly viscous, was moderately adsorbed by the skin and stayed in place. The electrode was then positioned at the site of DNA application, followed by electroporation, under the same electroporation conditions as described for Example 8. Luciferase gene expression was assayed at day 1 (24 hrs) after gene delivery.

Figure 22:
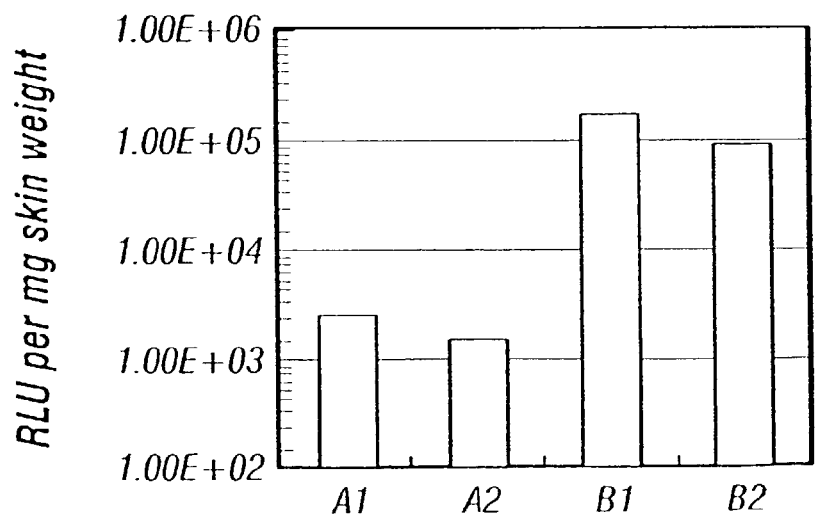
FIG. 22 depicts results obtained from the comparison of caliper vs. meander electrodes in delivering CMV-luciferase plasmid DNA to hairless mouse skin.

In order to investigate the location of gene expression in the skin layers, frozen sections of excised mouse skin were processed so that the full thickness skin (0.5 mm) was divided into two parts. The top part that was taken from outer most 150 um regions of the skin, the bottom part was the remainder of the skin. The enzyme activity was measured by the spectrophotometer after homogenization and extraction. The results were corrected for skin sample weight and the results are indicated graphically in FIG. 22. Bars A1 and A2 show meander electrode results, while bars B1 and B2 show caliper electrode results. A1 and B1 results were obtained from the outer 150 microns of skin, while A2 and B2 results were obtained from the remainder of the skin. Use of meander electrodes for electroporation resulted in much greater incorporation/expression of luciferase (i.e., two orders of magnitude). FIG. 22 further indicates that (1) a significant amount of luciferase DNA are delivered and expressed in the upper layers of the skin.

Example 12

Meander Electrodes Deliver CMV Beta-Gal and Involucrin Beta-Gal DNA in Nude Mice and Hairless Mice In order to test the relative expression achieved in mouse skin using genes driven by a CMV promoter as compared to the human involucrin promoter, the following experiment was conducted.

Fifty micrograms of plasmid DNA was administered to the skin via i.d. injection. Two sets of plasmids were used, containing the beta-galactosidase gene either driven by the CMV promoter or the human involucrin promoter. Pulsed (DNA (+) EP (+) and DNA (−) EP (+)) skin, and non-pulsed skin (DNA (+) EP (−)) was excised 24 hours after gene delivery. Electroporation was conducted as described in Example 8. Untreated skin (DNA (−) EP (−)) was also excised as a control. X-gal histochemical staining was used to illustrate the beta-galactosidase gene product.

Photomicrographs of skin cross sections were taken under the light microscope and intensive beta-galactosidase staining was observed with CMV beta-gal DNA delivery (i.d. injection+pulsing). It was distributed from epidermis to dermis. The expression of beta-gal DNA driven by the involucrin promoter was much weaker than with CMV promoter, and it was mostly located in the epidermal and upper dermal regions. No gene expression was observed with untreated skin, i.d. DNA injection alone, and pulsing without DNA.

These results demonstrate that it is feasible to target skin with a skin-specific promoter (i.e., involucrin). However, the involucrin promoter is much weaker than the CMV promoter.

Example 13

Improving Electroporation-Enhanced in vivo Gene Delivery to Skeletal Muscle

The goal of this series of experiments was to systematically determine the effect of different electroporation parameters on gene expression as well as on histological changes in the target tissue in small (rats) and large (pigs) animals, with the intent to identify EP conditions that enhance gene expession while reducing histopathological changes of the electroporated tissue and induction of an immune response related to such changes.

EP protocols

Plasmid DNA containing (i) the luciferase gene driven by the SV40 promoter (Clontech, Palo Alto, Calif.) and (ii) secreted alkaline phosphatase (SEAP) gene driven by the CMV enhancer/promoter (Valentis, Inc., The Woodlands, Tex.) were used for injection into (i) the semimembranosus muscle of Yorkshire pigs (10–30 kg), and (ii) the gracilis muscle of the hind legs of Sprague Dawley rats (approx. 400 g). For the pigs, 100 µg of the luciferase plasmid DNA in 500 µl of PBS was injected per injection site. For rats, 50 µg of SEAP plasmid DNA in 100 µl PBS per injection was introduced into both hind legs.

(a) Single vs. Six Auto Pulses for Delivering Luciferase or SEAP Plasmid DNA Into Porcine Semimembranosus Muscle by Electroporation A first set of experiments (represented by the results shown in FIGS. 23, 24 and 25) utilized two different electroporation protocols to compare the effect of different electroporation parameters upon gene expression. In one protocol, a single electric pulse was delivered to the injection site via a six-stainless steel needle array electrode at voltages that ranged from 150 V to 200 V (nominal field strength of about 174 to 232 V/cm, respectively) and for durations that ranged from 20 ms to 60 ms. Although this was a six-needle array, only two needle pairs were energized in delivering the single pulse For the other protocol, also using a six-stainless steel needle array six electric pulses at 4 Hz were delivered to the injection site at 200 V (nominal field strength of about 232 V/cm) and for durations of from 20 ms to 60 ms. A six-stainless-needle array electrode (diameter 1 cm, needle length 1 cm, Genetronics, Inc., described in U.S. Pat. No. 5,993,434, the disclosure of which is incorporated herein by reference in its entirety) with 0.86 cm distance between a pair of pulsing needles was used. An auto-switcher, as published in the biomedical literature, was connected between the needle array electrode and a square wave pulse generator ECM830 (Genetronics, Inc.). During the delivery of multiple pulses, four out of six electrodes were active per pulse, with sequential field rotation (60 degree) after every two pulses. A more detailed description of the pulse pattern can be found in U.S. Pat. No. 5,993,434. The six-needle array/autopulser/ECM 830 combination was also used in obtaining the multi-pulse results shown in FIGS. 29 and 32. The second pulse of each pair of pulses was of the opposite polarity relative to the first pulse. The results of these studies are summarized in FIGS. 23 and 24.

(b) Four-Gold-Needle Array Electrodes and Dual Pulses (4 Hz) Protocol to Study EP Conditions (Voltage, Pulse Duration) on the Level of Gene Expression and the Tissue Changes Over Time To study the effect of voltage escalation and pulse duration escalation on gene expression and histological tissue characteristics, a second set of experiments (represented by the results shown in FIGS. 26–31) compared the effect of the following electroporation parameters applied to porcine muscle: dual pulses (4 Hz) of either 50 V, 100V, or 200 V of 60 ms each were compared to each other. In addition, dual pulses of 100V with a duration of either 20 ms, 40 ms or 60 ms were evaluated, as well as dual pulses of 40 ms at 200 V. Dual pulses instead of single pulses were used in order to enhance the reproducibility of results. Because of variabilities from animal to animal and variabilities in investigator performance, two pulses tend to compensate for such variabilities to a higher degree than a single pulse.

In this set of experiments, four-gold-needle array electrodes were used to reduce toxic metal solubilization off stainless steel electrodes during electroporation (EP) and, thus, make the EP procedure more biocompatible. In addition, toxic metals in tissue may contribute to histopathological changes and thus enhance immune responses. The needle length was 1 cm, and the distance between each pair of pulsing needles was 0.86 cm. The geometry of the four-needle array was identical to the geometry of the subset of two active needle pairs in a six-needle array (see above). The DNA was injected via a 26-G needle with 0.8 cm of the needle tip inserted into the porcine muscle. Three minutes post DNA injection, the four-needle-array electrode was inserted. One minute later the pulses were delivered for the stated duration. The treatment sites were marked by India ink with a 1 cm diameter mark when DNA encoding non-secreted luciferase was used. On day 2 or day 7, muscle biopsies were taken using 8-mm punchers after euthanasia of the pigs. The biopsies were either sent for histology (Hematoxylin and Eosin staining) or luciferase assay.

Assays

Assays of luciferase expression were conducted as described above in Example 10, except that porcine muscle biopsies were taken at either day 2 or day 7 post DNA delivery. Luciferase activity of 50 µl of tissue/cell extract was measured in relative light units (RLU). Luciferase activity slightly decreased for both the EP cohort and non-EP cohort at day 7 compared to day 2, although the relative levels of gene expression in the non-EP and EP-treated animals remained consistent on days 2 and 7, i.e., gene expression was higher in the EP-treated animals as compared to the non-EP-treated animals on both days 2 and 7. SEAP antigen levels in serum were measured via an assay kit (Roche) with a luminometer using known methods. Pigs were bled at days 1, 3, 7, 14, and 21 post DNA delivery. Rats were bled at day 5 post treatment.

Samples of target porcine muscle were collected for pathological evaluation to determine the extent of tissue changes resulting from the various EP protocols. At days 4 and 14, biopsies were taken for Hematoxylin and Eosin staining. Three muscle samples from three pigs were harvested for each EP condition as well as for the DNA only (no EP) cohort. Three to four histology sections per biopsy were evaluated. Therefore, pathological evaluation on tissue histological changes was from at least 9 sections. Hematoxylin and Eosin stained histological samples were analyzed (blinded) by a pathologist according to the scale defined in FIG. 31.

Figure 23:
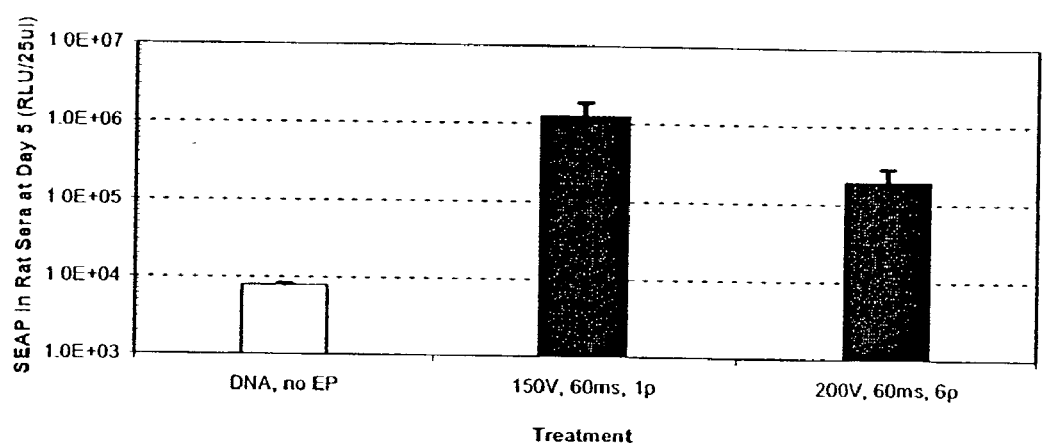
FIG. 23 is a graph showing SEAP expression (RLU) in rat muscle obtained from injection of DNA alone without electroporation and from electroporation enhanced SEAP plasmid DNA delivery (0.1 mg via 2 injection sites) using one or six auto-pulses (6-stainless steel needle array electrode, n=8.).
Figure 29:
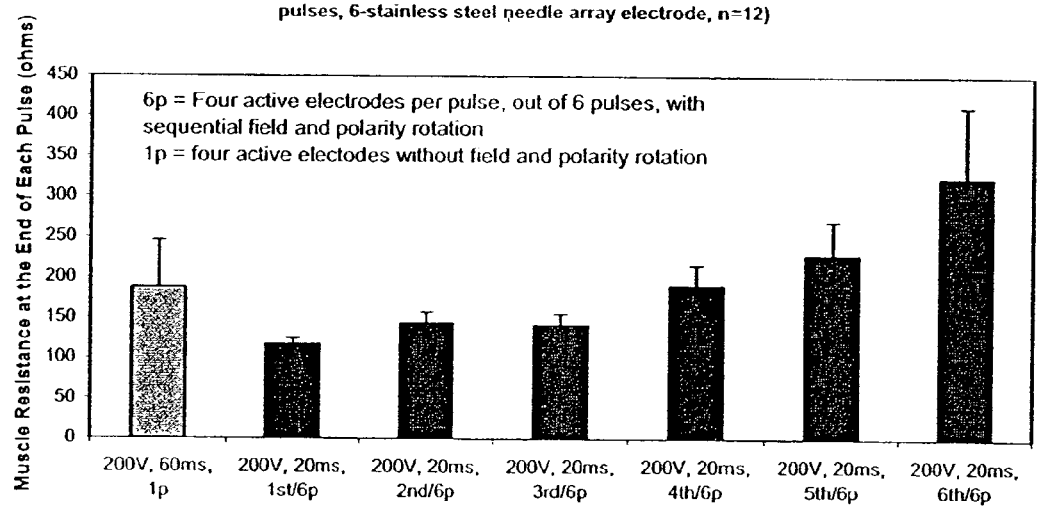
FIG. 29 is a graph showing porcine muscle resistance (ohms) at the end of each pulse for one electroporation pulse of 200 V for 60 ms or a train of six electroporation pulses of 200 V for 20 ms each (6-stainless steel needle array electrode, n=12).
Figure 30:
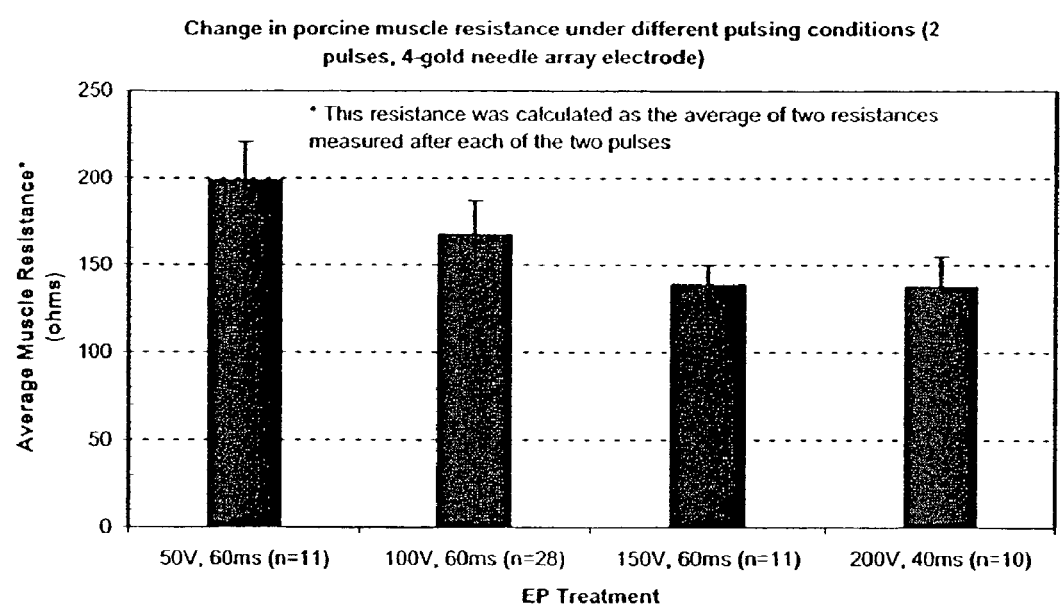
FIG. 30 is a graph showing average porcine muscle resistance (ohms) under different pulsing conditions (2 pulses, 4-gold needle array electrode).

For the above tests, current and voltage profiles of electroporation pulses across muscle tissue were monitored via oscilloscope and muscle resistance at the end of each pulse was determined. The results of these tests for porcine muscle are shown in FIGS. 29 and 30. Results FIG. 23 shows the result of comparing the effect of one pulse versus six pulses on the expression of SEAP in rat hind leg muscle as measured by SEAP levels in serum on day 5 after a one-time administration of SEAP plasmid DNA, with and without subsequent EP. SEAP levels were increased over 100-fold compared with DNA injection alone when a single pulse was delivered at 150V for 60 ms. However, SEAP levels increased only about 20-fold when six pulses were delivered, each at 200 V and 60 ms. In both cases (single and six pulses) a 6-needle array electrode was used. Pulses were generated by an ECM 830 square wave generator and routed to the 6-needle array via an autopulser. The autopulser energizes 4 needles each per pulse (see above). Thus, in the case where one pulse was delivered, the configuration of the four needles energized during the pulse is identical with the configuration of the standard 4-needle array electrodes used in most other experiments described in this Example. For the electroporation pattern that applies when 6 pulses are delivered, see above. The conclusion we draw from this experiment is that the delivery of six pulses yields a lower enhancement of SEAP expression than occurs when the SEAP encoding plasmid is delivered with one pulse. The histopathological changes in the target muscle tissue site associated with six pulses are significantly more severe than those resulting from one pulse (data not shown). Therefore, one pulse is superior to six pulses both in terms of high gene expression and low histological changes.

Figure 24:
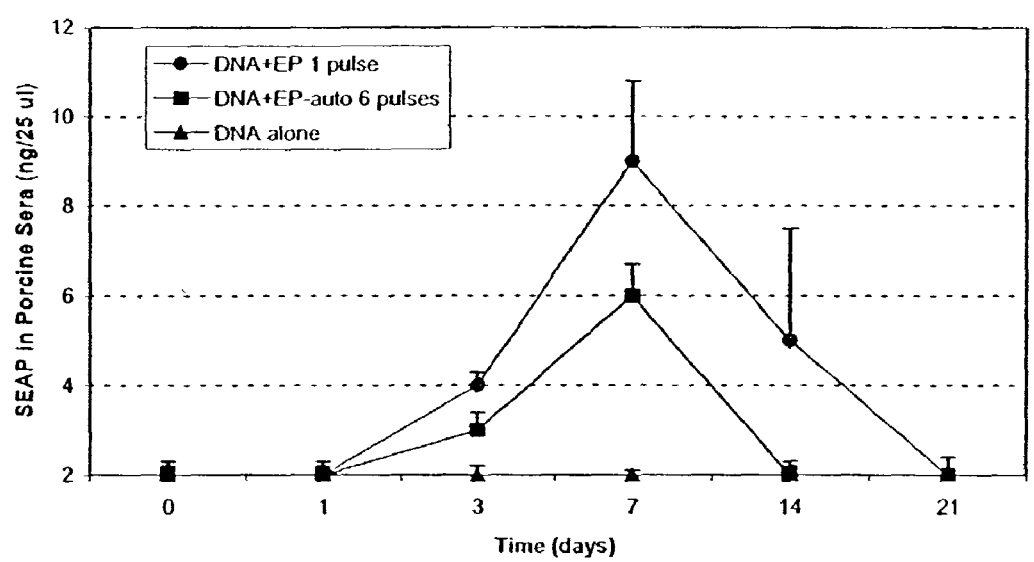
FIG. 24 is a graph showing SEAP expression (RLU) in pig muscle over three weeks obtained from injection of DNA alone without electroporation and from electroporation enhanced SEAP plasmid DNA delivery (1 mg via 4 injections) (200 V, 60 ms, 6-stainless steel needle array electrode, n=4).
Figure 26:
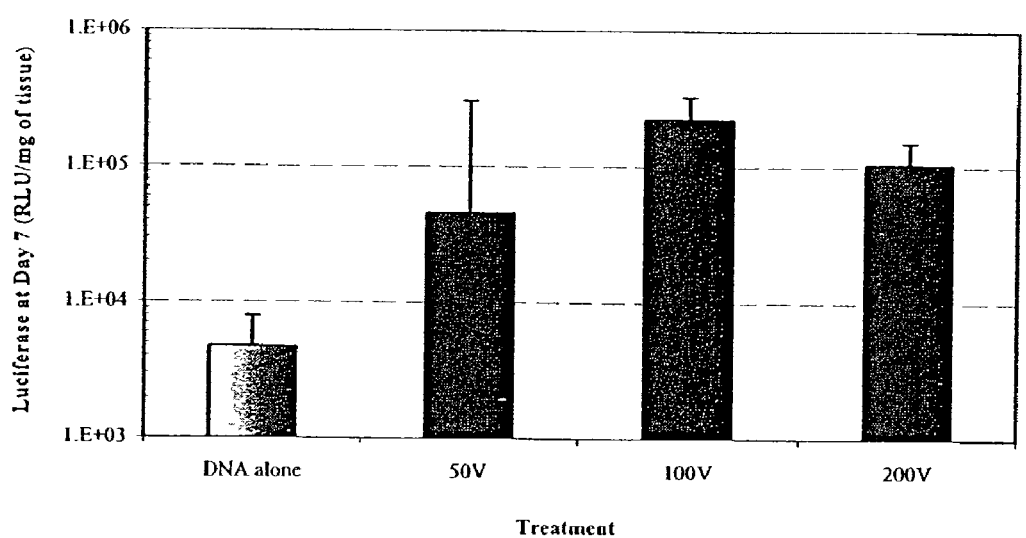
FIG. 26 is a graph showing luciferase expression (RLU) at day 7 post treatment achieved in porcine muscle by DNA alone without electroporation or electroporation enhanced plasmid DNA delivery over a range of electroporation voltages (4-gold needle array electrode, 60 ms, 2 pulses, n=5).

Although one pulse was delivered at 150 V and the six pulses were delivered at 200 V, it can be seen from FIG. 26 that the increase in gene expression due to EP at the same number of pulses (two) only varies by a factor of two. Therefore, the difference in serum levels in FIG. 23 can be largely attributed to the number of pulses rather than to the difference in voltage. This interpretation is supported by the results shown in FIG. 24 and pulse length (60 ms) conditions where one pulse was compared with 6 pulses under identical voltage (200 V). FIG. 24 shows a time course of SEAP expression in porcine muscle as measured by SEAP concentrations in serum, both for a single pulse regimen and a six-auto-pulse regimen, as described for FIG. 23. Again, the six-pulse regimen results in lower levels of transgene expression than the one-pulse regimen. For both the one-pulse and the six-pulse regimens, maximal SEAP levels were observed at day 7 after treatment.

Figure 25:
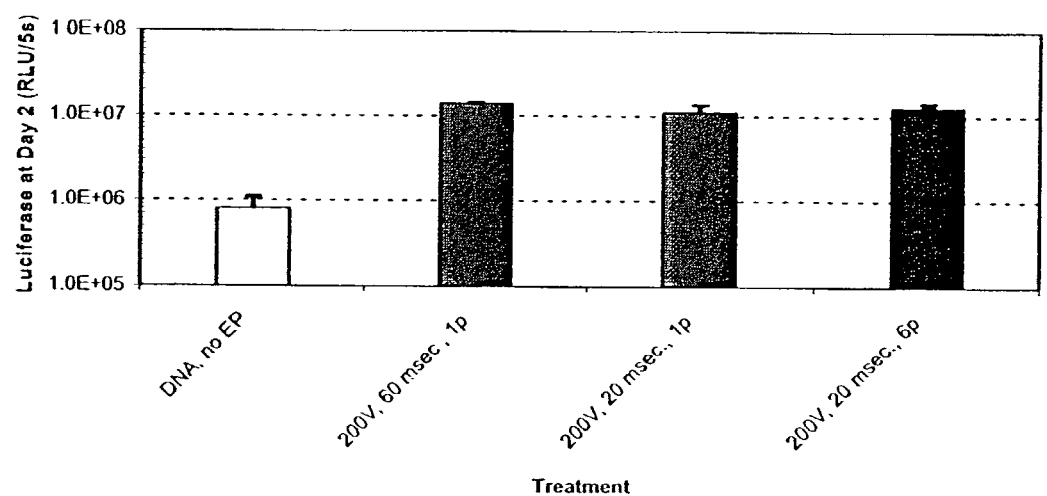
FIG. 25 is a graph showing luciferase expression (RLU) at day 2 post treatment achieved in porcine muscle using DNA alone without electroporation or electroporation enhanced plasmid DNA delivery at one pulse at 200 V for 60 ms or 20 ms or 6 pulses at 200 V for 20 ms.

FIG. 25 compares the level of luciferase expression at day 2 post treatment in porcine muscle using one pulse at 200 V for 60 ms or 20 ms vs. 6 pulses at 200 V for 20 ms. A six needle array as described for FIG. 23 was used. The single pulse protocol at either duration achieved an expression level comparable to that achieved using the 6-pulse protocol. In this experiment (FIG. 25) luciferase activity was measured in the muscle, as opposed to SEAP protein measured in serum (FIGS. 23 and 24). Contrary to SEAP, which is secreted from the muscle cells into the blood stream, luciferase is not secreted and remains in the cells where it is produced.

The results of the voltage escalation study in porcine muscle, FIG. 26, show the level of luciferase expression in porcine muscle at day 7 post treatment. Luciferase activity was highest when the electroporation voltage was 100 V as compared to 50 V or 200 V. Two pulses of 60 ms were applied using a 4-needle array with gold-coated needles.

Figure 27:
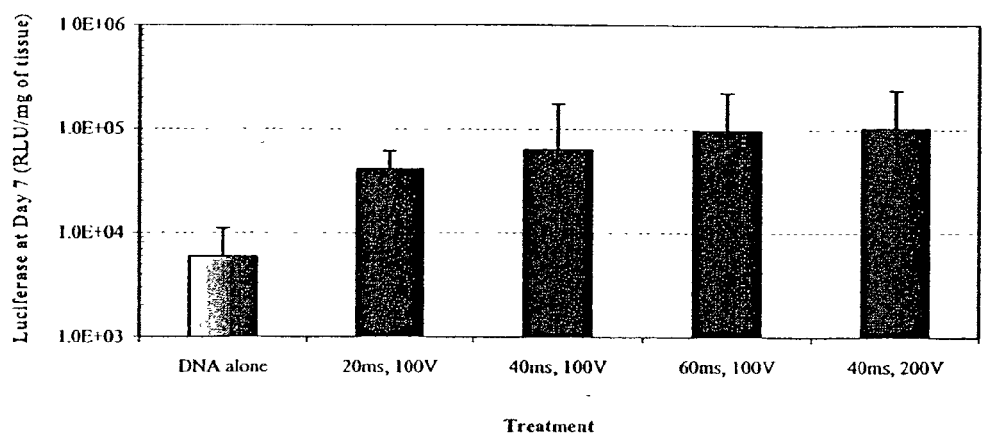
FIG. 27 is a graph showing luciferase expression (RLU) at day 7 post treatment achieved in porcine muscle by DNA alone without electroporation or electroporation enhanced plasmid DNA delivery over a range of electroporation pulse durations (4-gold needle array electrode, 2 pulses, n=6).

The results of the pulse duration escalation study in porcine muscle, FIG. 27, shows the level of luciferase expression in porcine muscle at day 7 post treatment. When 100 V pulses were applied, increasing the pulse duration from 20 ms to 40 ms to 60 ms resulted in a slight increase in luciferase activity. Increasing the voltage to 200 V for a duration of 40 ms per pulse yielded the same luciferase activity as was achieved with 100 V and 60 ms.

Figure 28:
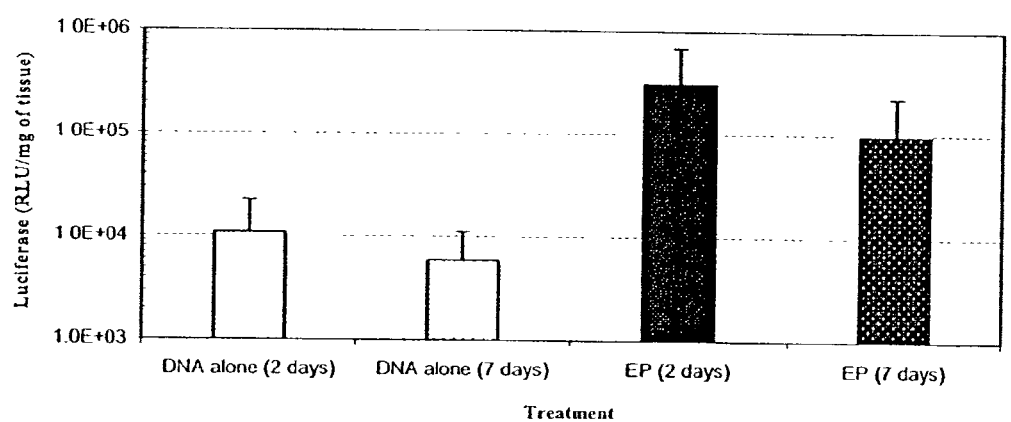
FIG. 28 is a graph comparing luciferase expression (RLU) in porcine muscle at 2 days and 7 days post treatment for DNA alone without electroporation and for electroporation enhanced DNA plasmid delivery (EP) (100 V, 60 ms, 2 pulses, 4-gold needle array electrode, n=6).

As shown in FIG. 28, expression of luciferase at 2 days post plasmid delivery (100V, 60 ms, 2 pulses, gold 4-needle array) to porcine muscle was roughly 40-times greater when enhanced by electroporation than for plasmid delivery without electroporation. On day 7 post plasmid delivery, the enhancement due to EP was only about 17-fold.

FIG. 29 shows the muscle resistance at the end of each pulse, measured between the needle electrodes that had delivered the pulse or pulses. For example, $3^{rd}/6p$ means that the resistance was measured after the third pulse within a 6-pulse series. Resistance increases only slightly after the first three pulses but increases at a faster rate after the fourth, fifth and sixth pulse. One pulse of 200 V, 60 ms results in about the same resistance as after the fourth pulse of 200 V, 20 ms. The resistance probably reflects both changes in the electrode/tissue interphase and in the muscle tissue between the electrodes. The higher the resistance change, the higher the probable changes occurring in the tissue. Therefore, in order to keep tissue changes low, both the number of pulses and the pulse duration should be kept low.

FIG. 30 shows muscle resistance as a function of applied voltage, using dual pulses of 60 ms each. Surprisingly, muscle resistance decreases with increasing voltage. Pulses of 150 V, 60 ms yield about the same resistance as pulses of 200 V, 40 ms. This may indicate that voltage has a less dramatic effect on tissue changes than does the number of pulses, at least within the ranges investigated in the experiments reflected in FIGS. 29 and 30. The results also indicate that the effect of higher voltage (200 V compared to 150 V) can be compensated by shorter pulse duration (40 ms vs. 60 ms).

Figure 31:
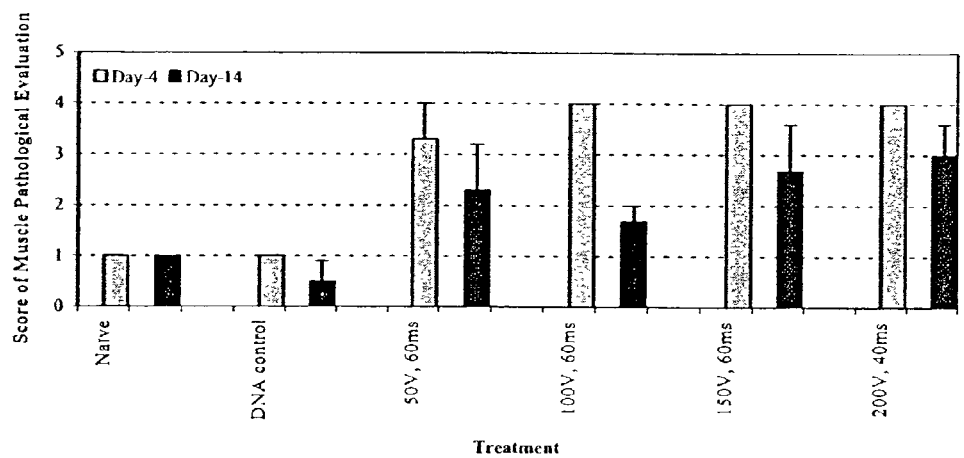
FIG. 31 is a graph showing the change of inflammation (on a scale of 1 to 5) in porcine muscle for naïve muscle and from day 4 to day 14 post treatment of luciferase DNA without electroporation and after electroporation enhanced delivery of luciferase plasmid DNA using various pulsing conditions (4-gold needle array electrode, n=9). Scale: 0=no change, 1–5=increasing severity of change.

As shown in FIG. 31, acute porcine muscle inflammation induced by electroporation at different voltages and pulse durations (2 pulses each, delivered at 4 Hz) subsides significantly by day 14 and subsides further at later times, as shown in a separate experiment, the results of which are summarized in FIG. 32. In separate studies the improved electroporation protocol, keeping the number of pulses, voltage and pulse length to a minimum, also was shown to reduce inducement of histopathological changes associated with necrosis and fibrosis.

The initial inflammatory response at day 4 was lower at lower voltages, with the exception of the 50 V pulses. The results also show about equal four-day and 14-day inflammatory responses for 150 V, 60 ms and 200 V, 40 ms, suggesting that the effect of higher voltages can be offset by shorter pulse duration. Inflammatory responses, especially early responses, may trigger or enhance an immune response against the therapeutic gene product and therefore should be kept at a minimum.

From the results shown here and results from other experiments, those of skill in the art can design electroporation conditions that will minimize histopathological changes and, consequently, immune response to the therapeutic gene product coded for by the delivered transgene. The EP conditions disclosed herein include low pulse number, low applied voltage, and low pulse length. Low pulse number ideally means one pulse, but requires using instrumentation that precisely delivers DNA into muscle and applies EP under defined 3-dimensional conditions that reproducibly yield equal levels of intracellular DNA delivery and gene expression. Low voltage under the conditions described in Example 13 means 100 V. However, the decisive factor in EP delivery of polynucleotides is field strength (V/cm) and, therefore, lower voltages can be applied when the spacing of the electrodes is narrower. The voltage can also be reduced if pulse length is increased, within the limits disclosed herein.

Low pulse length under the conditions described in Example 13 means 40 ms. However, it is conceivable that shorter pulses may be used if the field strength is increased accordingly. The actual combination of pulse number, applied voltage and pulse length will depend on the specific gene therapy application it will be designed for. For example, if only a relatively low level of transgene product is required, the transfection efficiency required does not have to be maximized and, therefore, pulse number, applied voltage and pulse length can be kept lower than when transfection efficiency has to be maximized. Furthermore, low pulse number, low applied voltage and short pulses will more likely suffice when multiple transfection sites in a target muscle or in a subject are used rather than one transfection site. These factors will flow into the design of the actual EP conditions to be used in a particular situation. The benefits derived from the improved EP conditions have been found to include high levels of gene expression (e.g., one pulse yields better gene expression than six pulses), reduced histopathological changes (both acute and longer term), and, thus, a lower probability of an immune response against the transgene product.

The improved electroporation protocol described herein was effective in both rats and pigs (i.e. large animals). Optimal gene expression levels and minimal tissue changes could be achieved using single or dual pulses of appropriate parameters. Use of larger numbers of pulses at higher voltages with polarity reversal results in a lower level of gene expression (for both secreted and non-secreted protein), higher muscle resistance, and longer recovery time compared to single or dual pulse mode of EP disclosed in this invention.

Besides making electroporation more readily acceptable to patients, the results indicate that reducing transient inflammation by selection of electroporation parameters as described herein has a positive effect on the capacity for gene expression derived from electroporation-enhanced DNA delivery, for example for gene therapy.

Example 14

Delivery of Nucleic Acids to Skin Using Non-Invasive Electrodes

Plasmid DNA: pCMVbeta encoding the lacZ gene (beta-galactosidase) driven by the CMV IE promoter was purchased from Clontech (Palo Alto, Calif.). The plasmid containing the luciferase gene driven by the CMV enhancer/promoter ("luciferase plasmid DNA") was a gift of Valentis, Inc. (The Woodlands, Tex.). Concentrated DNA solutions were diluted with 1×PBS from Irvine Scientific (Irvine, Calif.).

Animals: SKH1 female hairless mice, 8–12 weeks of age, were purchased (Charles River Laboratories, Wilmington, Mass.) and housed at Genetronics, Inc. (San Diego, Calif.). CD1 nude mice used for human skin xenograft transplantation experiments were purchased from Charles River Laboratories and housed at AntiCancer, Inc. (San Diego, Calif.). All mice were humanely euthanized by $CO_2$ asphyxiation at the end of the experiments. These studies were approved by the Institutional Animal Care and Use Committees (IACUC) of the study sites and performed in accordance with the Guide for the Care and Use of Laboratory Animals.

Human skin transplantation onto nude mice: Fresh human skin from breast surgery was purchased from the National Disease Research Interchange (NDRI) (Philadelphia, Pa.) and tested by an independent laboratory for the absence of pathogens (The Children's Hospital of Philadelphia, Pa.). Mice were anesthetized using isoflurane inhalation. For each graft, a full-layer patch of skin from the mouse's back, about 2×2 cm, was removed. Each human skin flap was prepared by removing subcutaneous tissue and cutting the patch to the same size as the exposed area on the mouse. 6-0 Silk sutures were used to affix the human skin flap onto the mouse's back. The surgical area was protected by a gauze pad and Tegaderm® (3M, St. Paul, Minn.), a transparent dressing film. Each mouse was housed individually in a cage under sterile conditions. The animals were monitored for several weeks to confirm acceptance of the skin grafts. In vivo gene delivery with electroporation ("EP") did not begin until 8 to 10 weeks later when the grafts were fully healed.

Luciferase assays: In all but the time course experiments, mice were sacrificed 48 hours after intradermal injection of DNA. Uniform skin specimens were immediately sampled using a 6 mm biopsy puncher (Miltex, Lake Success, N.Y.), and frozen at −70° C. until processed for measuring luciferase activity. Luciferase activity was measured using a luciferase assay kit (Roche, Indianapolis, Ind.). Skin specimens were thawed, then homogenized in an Eppendorf tube containing 300 microliters of lysis buffer, using fine surgical scissors (Roboz, Gaithersburg, Md.), and a pestle (Nalge Nunc Intnl., Naperville, Ill.). The samples were centrifuged for 5 minutes at 10,000 rpm, 50 microliters of supernatant was transferred to a new microfuge tube and mixed with 100 microliters of the luciferase assay reagent. Luciferase activity was measured for 5 seconds with a luminometer (MGM Instruments, Hamden, Conn.). Relative light units (RLUs) were normalized over milligrams of protein, as determined from a separate aliquot of supernatant with a non-interfering protein assay kit (Geno-Tech, St. Louis, Mo.). Optical density readouts for the protein assay were obtained using a spectrophotometer (Packard, Downers Grove, Ill.). The luciferase expression level was recorded as RLUs/mg protein.

X-gal histochemistry: Skin samples were excised at 24 hours post DNA injection and immediately fixed in 2% formaldehyde/PBS (10:1) for 15–60 minutes. Tissue was rinsed thoroughly for 15 minutes in PBS, incubated in the X-gal staining solution at 37° C. for 24 hours, fixed in 10% formalin, and embedded in paraffin. Sections of 5 micrometer thickness were counter stained with 0.1% nuclear fast red.

Statistical analysis: The significance of the results obtained with EP and non-EP groups was determined by an unpaired t-test. The data in the graphs are presented as the mean±standard error.

Intradermal DNA injection and in vivo electroporation: Mice were anesthetized using isoflurane inhalation. Plasmid DNA (25 microliters per site, at concentrations noted for individual experiments) was intradermally injected with a 28-gauge needle into the lower dorsal side or into the human skin xenograft, respectively. To minimize variability, the same skilled operator performed all injections. The area around the injection site was dried before applying the electrodes. A 20- to 30-second time interval lapsed between injection and initiation of EP. The in vivo electroporation system (Genetronics, Inc.) consisted of a square wave pulse generator (ECM 830) and either a caliper or a meander electrode, both of which were applied topically. The caliper electrode (P/N 384) consists of two brass plate electrodes, measuring 1×1 cm, which squeeze the skin fold to be electroporated (FIG. 33(A)). The distance between the two electrodes depends on the thickness of the skin fold (~1 mm for mouse skin, 3 to 4 mm for human skin), and can be measured using the caliper scale. The meander electrode consists of an array of interweaving electrode fingers of alternating polarity (FIG. 33(B)). The width of each electrode is 2 mm and the gap between electrode fingers is 0.2 mm; the gaps are filled with insulation material. Under some EP protocols, a polarity switching box (Genetronics, Inc.)

was used to reverse the polarity of the pulses. The applied voltage across the skin fold between caliper electrodes, and the current passing through the skin before and during electroporation, respectively, were measured using voltage and current probes connected to a digital oscilloscope. The skin impedance prior to electroporation was measured using alternating current (sine wave, $V_O$=1.5 V, 1 kHz) produced by a function generator. The electroporated area was marked with a surgical marker at the end of each experiment, and a skin biopsy was taken at each appropriate time point.

(a) Effect of DNA dose on transgene expression.

Five mice per each of five DNA doses (a total of 25 mice) were injected intradermally at multiple dorsal sites with 25 microliters of DNA solution containing 2, 5, 10, 50, or 100 micrograms of luciferase plasmid DNA, respectively. EP was performed on half of the injected sites using caliper electrodes (6 pulses of 20 ms each, 75 V, 10 Hz, polarity reversal after 3 pulses). The other half of the injected sites served as controls (no EP). Luciferase expression was measured as described below.

Figure 34:
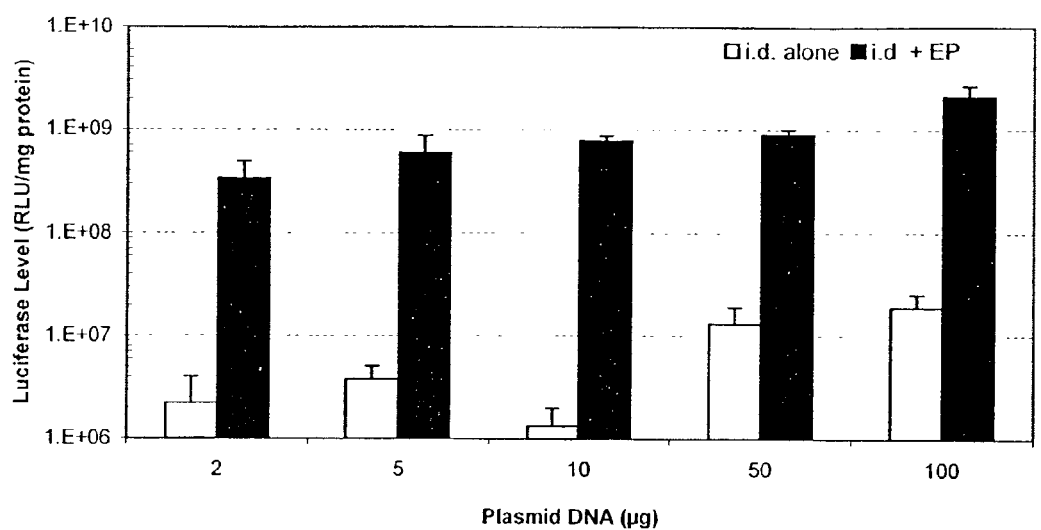
FIG. 34 is a graph of transgenic luciferase expression in mouse skin. Indicated various amounts of DNA were injected intradermally in volumes of 25 µl each. The average background luciferase activity, measured in naïve mice, was $1.4 \times 10^4$ RLU/mg protein. All electroporated groups showed statistically significant increases in gene expression over their controls without EP. Error bars represent S.E. M. (n=5), i.d.=intradermal injection.

Both with and without EP, luciferase expression increased with the amount of DNA injected intradermally (FIG. 34). Relative to controls, in which DNA was injected without electroporation, the injection of genes with EP elevated gene expression on average more than 200-fold across the range of DNA doses injected (P<0.02). The increase in gene expression in response to raising the DNA dose from 2 to 100 micrograms was less than 7-fold in the presence of EP, and approximately 10-fold in the absence of EP. The increase in gene expression was not proportional to the amount of DNA injected. To ensure that this was not due to a DNA saturation effect, an independent set of experiments was performed using DNA doses of 0.1 to 2.0 micrograms. Even using these low amounts of DNA, the increase in gene expression seen with EP vs. that seen without EP was not proportional to the amount of DNA, but displayed about the same rate of increase as seen in FIG. 34 (results not shown).

(b) Time course of Transgene Expression

Five mice per each experimental time point were injected intradermally with 10 micrograms luciferase plasmid DNA in 25 microliters at multiple dorsal sites. Sites in the left dorsal area received EP, whereas sites in the right dorsal area served as controls and were not electroporated. Luciferase activity was measured at 6 and 12 hours, and on days 1, 7, and 15 after DNA injection.

Figure 35:
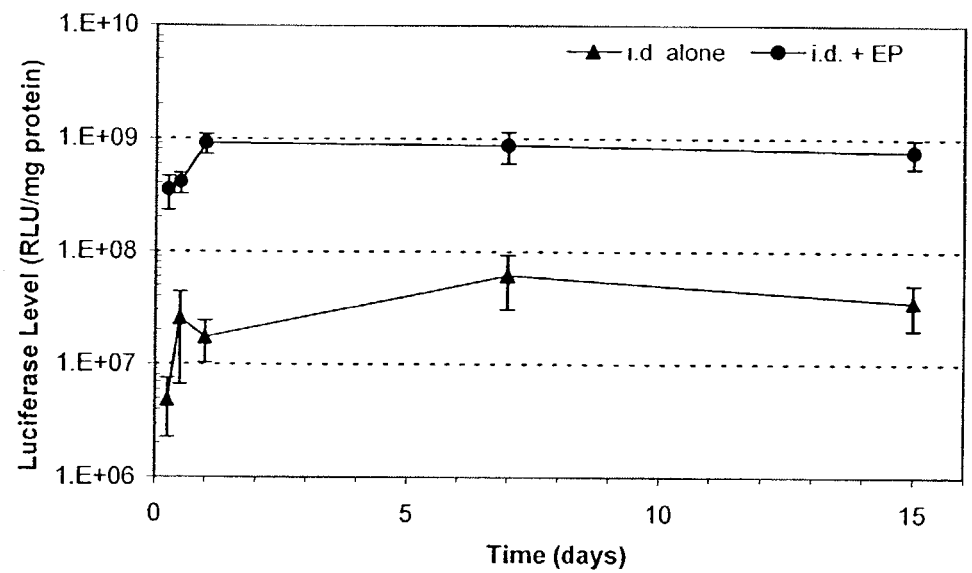
FIG. 35 is a graph of time course of transgenic luciferase expression in mouse skin. Luciferase-encoding DNA (10 µg/25 µl) was injected intradermally, either followed by EP or without subsequent EP. Gene expression was significantly increased by EP at all time points, relative to controls without EP (p<0.02 at 6 h, p<0.003 at 12 h, p<0.003 at 24 h, and p<0.04 at 7 and 15 days). Error bars represent S.E. M. (n=5)

The time course data indicate a rapid increase of luciferase activity after transfection, both in the presence and absence of EP (FIG. 35). At the first time point measured (6 hours), the increase was already more than 8 orders of magnitude above background with EP, and more than 6 orders of magnitude above background without EP. Of course, the important finding is that electroporation stimulated the amount of luciferase by about a factor of one hundred. Both curves plateaued at about 24 hours and that level was more or less sustained for at least 15 days. The standard error margins were consistently lower in the presence of EP as compared to those calculated in the absence of EP, a feature that has also been observed by others (Mir et al., *PNAS* 96:4262–4267; 1999).

(c) Effect of Various Electroporation Conditions on Transgene Expression

The effect of pulse number, pulse polarity, and type of electrode were investigated. Five to seven mice per EP condition to be evaluated were injected intradermally with 10 micrograms of luciferase plasmid DNA in 25 microliters. With the exception of the control group (four mice, no EP), all groups were electroporated with pulses of 20 ms at 75 V and 10 Hz.

Six different groups received pulses with caliper electrodes as follows: Either 1, 3, or 6 pulses without polarity reversal; or 2, 6, or 12 pulses with polarity reversal after half the number of pulses were delivered. One group was electroporated with meander electrodes instead of caliper electrodes (6 pulses as described above, with polarity reversal after the first 3 pulses).

Figure 36:
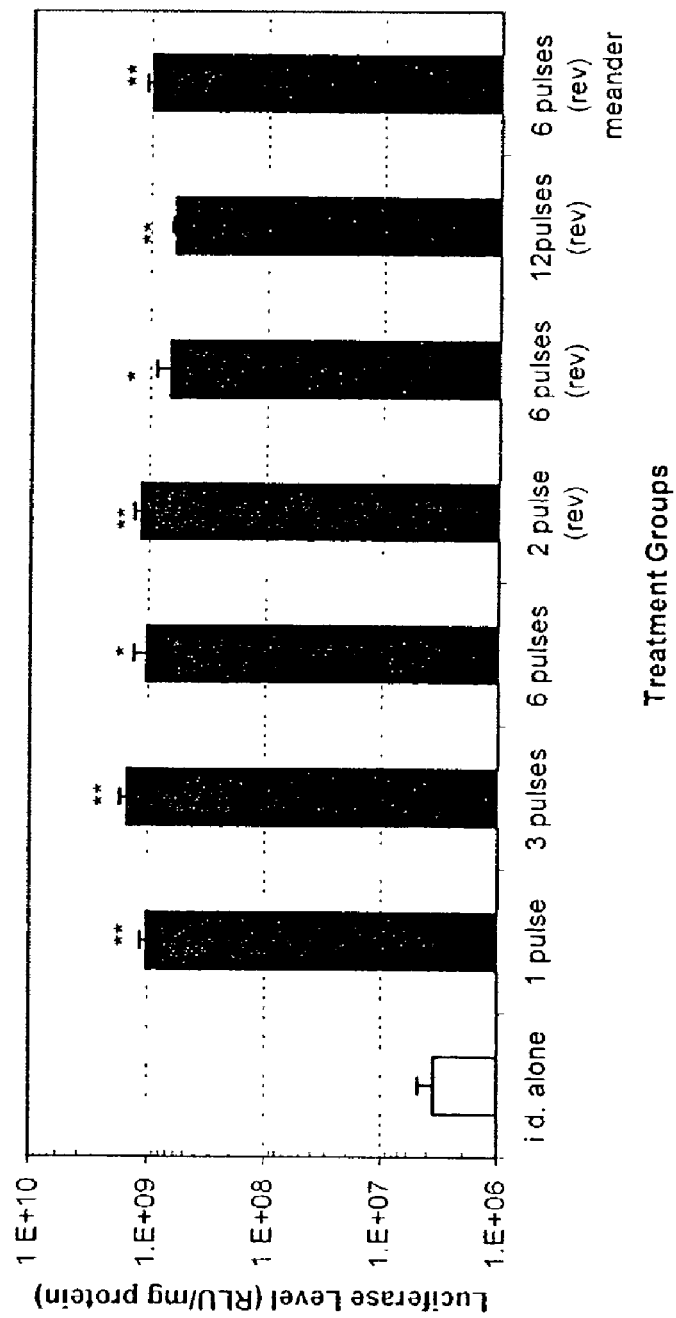
FIG. 36 is a graph of luciferase gene expression in response to different modes of EP. Variables include the number of pulses, type of electrode, and reversal of polarity (rev). Luciferase-encoding plasmid DNA (10 µg in 25 µl) was injected into mouse skin, followed by EP, except for the control group, which was not electroporated. EP pulses (75 V, 25 ms, 10 Hz) were delivered in the numbers indicated, using caliper electrodes unless stated differently. Multiple pulses were either of the same polarity or polarity was reversed (rev) after half the number of pulses indicated. Error bars represent S.E. M. (n=5). The level of statistical significance of expression enhancement by EP over the non-EP control is indicated by *(p<0.02) and **(p<0.001), respectively.

When various pulsing modes were assessed, EP significantly elevated luciferase gene expression between 200 and 430-fold over the control value obtained in the absence of EP (P<0.02) (FIG. 36). A single EP pulse was sufficient to increase luciferase activity 340 times over DNA injection without EP (P<0.0005) and was as effective as multiple pulses. In these experiments, reversal of polarity did not positively impact gene expression efficiency. In fact, three pulses without polarity reversal resulted in better expression levels than three pulses of one polarity followed by three more pulses of opposite polarity (P<0.002). In addition, 6 pulses without polarity reversal also appeared slightly superior to 6 pulses with polarity reversal. Meander and caliper electrodes, which are both non-invasive, resulted in equivalent levels of luciferase expression under the conditions tested (P<0.11).

(d) Electroporation-Mediated Transfer of Nucleic Acid to Human Skin

LacZ plasmid DNA (25 micrograms in 25 microliters) was injected into grafted human skin and mouse skin, respectively, in different animals. EP consisted of 60 pulses of 2 ms duration each, delivered by caliper electrodes at 100V, 10 Hz, and reversal of polarity after 30 pulses. Mouse skin was also electroporated with 6 pulses of 20 ms duration, and otherwise identical pulse parameters.

Figure 37:
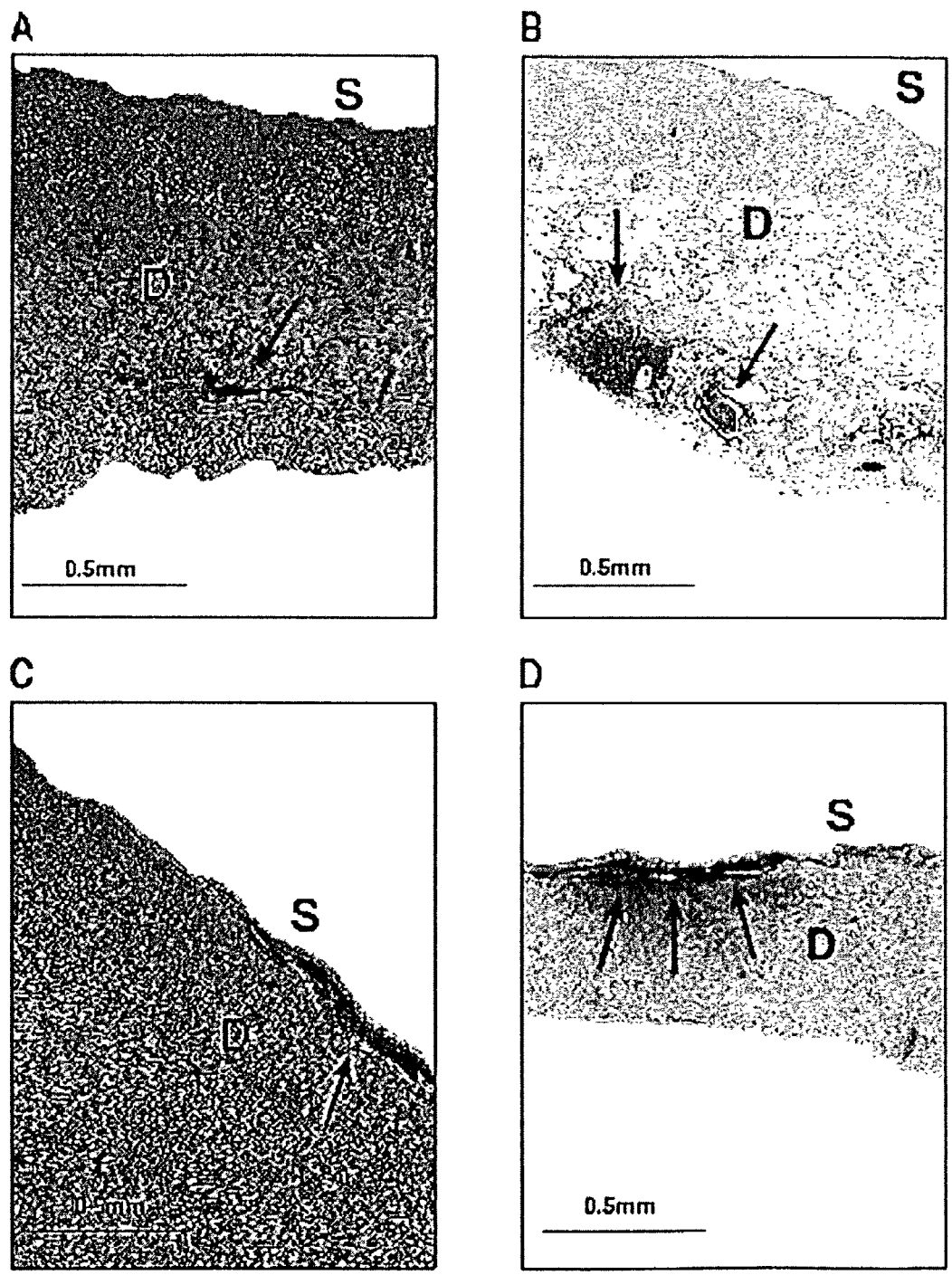
FIG. 37A, FIG. 37B, FIG. 37C, and FIG. 37D depict gene expression in mouse skin and xenografted human skin. PCMVbeta DNA (25 µg in 25 µl) was injected intradermally into mouse skin and human xenograft as shallowly as possible, followed by EP where applicable (caliper electrode, 60 pulses, 2 ms, 100V, 10 Hz, polarity reversal after 30 pulses). Biopsies were taken from treatment sites 24 h post-DNA delivery. Representative X-gal stained skin cross sections are shown in pictures A–D. The upper panels represent beta-galactosidase expression (arrows) in mouse skin after intradermal injection without EP (A), and intradermal injection with EP (B). The lower panels show beta-galactosidase expression in human skin after intradermal injection without EP (C), and after intradermal injection with EP (D). Most of the gene expression occurred in the dermis of the mouse skin, and in the epidermal region of the human skin graft. S=surface of the skin, D=dermis of the skin.

The goal of this experiment was two-fold: (i) to determine whether the stimulation of gene expression observed in mouse skin can also be achieved in the structurally different and much thicker human skin; and (ii) to evaluate the distribution of gene expression across the skin layers. Beta-galactosidase expression was compared in mouse skin and human xenografted skin by injecting LacZ plasmid DNA with and without subsequent electroporation. In half the animals DNA injection was followed by electroporation of the injection site, while the other half did not receive electroporation. Beta-galactosidase as marker enzyme provides the advantage that the location of gene expression can be determined, which is difficult to achieve with luciferase. FIG. 37 shows representative samples of X-gal stained skin sections of mouse skin (upper panels) and human skin (lower panels). Beta-galactosidase activity primarily appeared in the lower dermis of mouse skin and in the epidermis and epidermal/dermal junction of human skin. Electroporation significantly enhanced beta-galactosidase activity in mouse as well as human skin (FIG. 37, panels B and D), although the degree of enhancement is difficult to quantify. A similar result as shown in panels A and B of FIG. 37 was obtained when the same experiment was performed under different electroporation conditions (6 pulses of 20 ms each instead of 60 pulses of 2 ms each) resulting in the same total charge transfer. This finding corroborates the conclusion drawn from the experiment reported in part (e) below, that the number and duration of pulses can be changed within a wide range as long as the total charge and the electric field strength (E) remain constant.

(e) Effect of Different Pulse Conditions Delivering the Same Total Charge on Transgene Expression In order to better understand the influence of the different pulse parameters on the resulting level of gene expression, various pulse conditions were examined while keeping the total charge transfer constant. The applied voltage was varied between 50 and 100 V, the pulse length was varied between 2 and 30 ms, the number of pulses was varied between 3 and 30, and the frequency of pulse delivery was varied from 1 to 10 Hz. The combinations of pulse conditions shown in Table 7 were chosen such that each combination resulted in the same charge transfer, Q, namely 12 mCoulomb (mC) under the experimental conditions used. This value was calculated from measurements of the applied voltage and current during EP pulses, using equation (1) given below.

Four mice per EP condition to be tested were injected intradermally with 25 microliters containing either 0.1 or 10.0 micrograms of luciferase plasmid DNA (a total of 12 mice, 4 sites per mouse). Each of the EP protocols resulted in the same total charge transfer, Q. Electroporation pulses as indicated in Table 7 were delivered with caliper electrodes. The total charge (Q) and energy (W) delivered by each EP protocol were calculated using equations (1) and (2):

$$Q = I \times t \times N = (V/R) \times t \times N \times \quad (1)$$

$$W = I \times V \times t \times N = (V^2/R) \times t \times N \quad (2)$$

where I is the current in Amps, V is the applied voltage in Volts, t is the pulse length in seconds, N is the number of pulses, and R is the skin resistance in Ohms during the electroporation. The gene expression efficiencies of the different EP protocols shown in Table 7 were calculated according to equation (3) and normalized to the expression efficiencies obtained with protocol C:

$$\text{Efficiency} = (RLU/\text{mg protein})/Q \quad (3)$$

As known, skin resistance changes during the course of EP due to the breakdown ("poration") of the stratum corneum [Weaver, J. Cell. Biochem. 51:426–435; 1993]. An average impedance of 70 kOhms was calculated for mouse skin-fold prior to electroporation. During the first and third EP pulses measured (75 V, 25 ms, and 10 Hz), the average skin impedance decreased to 375 Ohms, a 187-fold drop.

The results of comparing the different pulse conditions under constant charge are summarized in Table 7. The efficiencies of gene expression were normalized to $9 \times 10^8$ and $15 \times 10^8$ RLU/mg protein for the 0.1 and 10 microgram doses of DNA, respectively. At the low DNA dose (0.1 micrograms) the efficiency of luciferase expression increases in a statistically significant manner with higher voltages (protocols A, B and C). Increasing the number of pulses while decreasing the pulse length at constant voltage and pulse frequency resulted in higher average gene expression efficiency (protocol B vs. D). Changing the pulse frequency did not result in a statistically significant difference (protocol B vs. E). Interestingly, at a higher but still relatively small DNA dose (10 micrograms), the differences in relative efficiency are smaller than at the low DNA dose and none of the changes is statistically significant (protocols A–E). At constant charge, the different pulse conditions shown in Table 7 resulted in total energies between 0.6 and 1.2 J.

When 10 micrograms of DNA were injected, followed by EP, none of the different parameters examined affected gene expression in a significant way within the range of parameters tested. However, when a one-hundred-fold lesser amount of DNA was injected, the differences evoked by the different pulse conditions were more pronounced, with the most significant influence seen with increasing voltage (and a corresponding decrease in pulse length), which resulted in higher transgene expression efficiency. Increasing the number of pulses (with a corresponding reduction in pulse length) also caused an increase in gene expression efficiency, but this difference was statistically not significant; neither was the change observed in response to varying the pulse frequency. While not wishing to be bound by theory, the reason why different pulse parameters affect expression efficiency more strongly at the lower DNA dose than at the higher DNA dose may be related to saturation and/or toxicity effects similar to those discussed below in the context of DNA dose effects on the level of gene expression.

(f) Summary Comments

Cutaneous transfection by plasmid DNA injection and EP has a number of advantages over other viral and nonviral methods, including safety and high efficacy. In addition, because of its simplicity, the method is readily applicable in clinical settings, is economically advantageous, and may receive relatively quick regulatory approval. Skin irritation from EP in rats and mice is mild and transient. Skin electroporation with meander-type electrodes was also well tolerated by patients and healthy volunteers in clinical studies, without significant pain or other side effects.

The design of the electrodes used for skin EP is important in several aspects. Electrodes must deliver an electrical field of sufficient strength and appropriate three-dimensional distribution to exert effective electroporation while keeping potential tissue damage to a minimum. Preferably, electrodes should also be easy to apply, be patient-friendly, hygienic, and inexpensive. Noninvasive electrodes have the advantage of being more readily accepted by the patient (no fear of needles, no pain of insertion), and provide less opportunity for infection. A potential shortcoming of these electrodes is their dependence on uniform skin contact as well as the requirement of effective electroporation of the stratum corneum. However, with proper design and application, these electrodes can be successfully used, as shown by the experiments described in this and previous studies. Among the noninvasive electrodes, meander-type electrodes may be the most desirable for future clinical use.

Noninvasive electroporation with caliper as well as meander electrodes is very effective without causing visible side effects on the skin. On average, a more than 100-fold improvement in gene expression with EP over DNA injection alone was observed using relatively long pulses at low field strength (LP/LV) conditions. The stimulatory effect of EP on gene expression is more pronounced at low DNA doses (at the microgram and sub-microgram level) than at high DNA concentrations in the 50–100 microgram range. A similar trend was also reported by Drabick et al. in porcine skin using short needle electrodes and different pulse conditions [Drabick et al., Mol. Ther. 2:140–146; 2001]. The reason for this nonlinear effect is not clear. Without wishing to be bound by theory, the effect may be related to saturation of the capacity for DNA uptake by the cells located in the relatively small tissue volume into which the DNA is injected, or to a cytotoxic effect caused by the large quantities of DNA delivered into the cells. Alternatively, the cellular machinery for RNA and protein synthesis may simply be overwhelmed by the amount of DNA template available.

The appearance of transgene product after DNA injection is rapid, both in the absence and presence of EP. At the earliest time measured, 6 hours after DNA injection, luciferase activity was already several orders of magnitude above background (about $10^8$-fold with EP, and $10^6$-fold without EP). Expression plateaus were reached at approximately 24 hours and persisted for at least 15 days. Since mouse epidermis is completely renewed approximately every seven days [Potten, *Int. Rev. Cytol.* 69:271–318; 1981], the relatively long duration of luciferase expression observed suggests that the bulk of transgene expression occurs in the dermis rather than the epidermis. This interpretation is supported by histological evidence showing that lacZ expression indeed takes place primarily in the mouse dermal layer under the experimental conditions used.

The number of pulses as well as pulse polarity appeared to have little influence on the level of stimulation of gene expression. One pulse and six pulses resulted in the same level of gene expression. Even the highest and lowest levels of gene expression observed between a set of 3 pulses and a set of 12 pulses with polarity reversal after 6 pulses was at best 3-fold. Since the potential for tissue damage increases with the amount of energy applied, there may be advantages to use one or a small number of pulses to minimize damage while still obtaining high levels of gene expression.

DNA expression in the epidermis is potentially advantageous for applications where short-term gene expression is sufficient, e.g., in DNA vaccination, in the treatment of temporarily anemic patients undergoing chemotherapy, in cytokine therapies, or in the acceleration of wound healing. Since the epidermis is constantly being renewed and old cells are being eliminated, the transgenic DNA will be eliminated together with the epidermal cells. This elimination process may help to reduce the real or perceived risk connected with the sustained presence of foreign DNA in tissues subjected to gene therapy or DNA vaccination. In the experiments reported here, transgene expression was confined largely to the human epidermis upon intradermal injection and non-invasive EP. If necessary, confinement of gene expression can be further increased by making use of specific promoters that are only active in specific cells, e.g., in keratinocytes [Wang et al., *PNAS* 94:219–226; 1997]. In contrast to the results obtained with human skin xenografts, transgene expression was not specifically targeted to mouse epidermis. This finding is consistent with previous findings by Hengge et al. who studied transgene expression in various skin types in the absence of electroporation and found that for unknown reasons intradermal injection of DNA results in transgene expression primarily in the epidermis of pig and human skin, yet primarily in the dermal region of mouse skin [Hengge et al., *J. Clin. Invest.* 97:2911–2916; 1996].

Although the invention has been described with reference to the presently preferred embodiment, it should be understood that various modifications can be made without departing from the spirit of the invention. Accordingly, the invention is limited only by the following claims.

What is claimed is:

1. An in vivo method for enhancing expression of a therapeutic polypeptide encoded by an isolated polynucleotide to be delivered into skin cells in vivo in a subject, said method comprising:
    a) introducing about 0.05 $\mu$g to about 100 $\mu$g per skin tissue site of at least one isolated polynucleotide encoding a therapeutic polypeptide into one or more skin tissue sites of a subject;
    b) applying at least two non-invasive electrodes to the skin tissue site;
    c) generating a total charge transfer at the skin tissue site of about one mCoulomb (mC) to about 1000 mC per skin tissue site by introducing one or more electric pulses to generate said total charge transfer at the skin tissue site, at substantially the same time as the introduction of the polynucleotide so as to result in the polynucleotide entering cells of the skin tissue for expression of the therapeutic polypeptide therein;

thereby enhancing the expression of the therapeutic polypeptide as compared to expression of the therapeutic polypeptide achieved by other methods for generating an electric field in target skin tissue.

2. The method of claim 1, wherein the total charge transfer at the skin tissue site is about 10 mC/cm to about 20 mC/cm$^2$.

3. The method of claim 1, wherein about 0.1 $\mu$g to about 10 $\mu$g per skin tissue site of the polynucleotide is introduced.

4. The method of claim 1, wherein the electrodes are the non-invasive electrodes.

5. The method of claim 4, further comprising reducing resistance of the stratum corneum in the skin site prior to generating the charge transfer at the skin tissue site by a procedure selected from laser treatment, tape stripping, electroporation, ultrasound, penetration enhancing chemicals, and any combination thereof, and wherein the isolated polynucleotide is applied topically to the skin tissue site.

6. The method of claim 4, wherein the non-invasive electrodes are contained in a meander electrode.

7. The method of claim 6, wherein distance between electrodes in the meander electrode is about 0.2 mm.

8. The method of claim 7, wherein the charge transfer is generated by applying the one or more electric pulses at a voltage of about 40 V to about 100 V to the electrodes.

9. The method of claim 7, wherein each electric pulse is applied for a period of about 1 ms to about 100 ms.

10. The method of claim 7, wherein the frequency of the electric pulses is about 1 to about 10 Hz.

11. The method of claim 4, wherein the non-invasive electrodes are caliper electrodes.

12. The method of claim 11, wherein the charge transfer is generated by applying the one or more electric pulses so as to cause a nominal field strength in the skin site of about 200 V/cm to about 2500 V/cm.

13. The method of claim 12, wherein each electric pulse is applied for a period of about 0.1 ms to about 100 ms.

14. The method of claim 12, wherein the frequency of the electric pulses is about 1 Hz to about 10 Hz.

15. The method of claim 12, wherein from one to about 30 of the electric pulses are applied.

16. The method of claim 1, wherein the subject is a mammal.

17. The method of claim 1, wherein the subject is a human.

18. The method of claim 1, wherein the polynucleotide is selected from double stranded DNA, single-stranded DNA, complexed DNA, formulated DNA, encapsulated DNA, naked RNA, encapsulated RNA, and combinations thereof.

19. The method of claim 1, wherein the polynucleotide encoding the therapeutic polypeptide is contained in a DNA vector.

20. The method of claim 19, wherein the polynucleotide is operably associated with a regulatory sequence for expression of the therapeutic polypeptide in cells.

21. The method of claim 20, wherein the polynucleotide further encodes a selectable marker polypeptide.

22. The method of claim 20, wherein the regulatory sequence comprises a promoter.

23. The method of claim 22, wherein the promoter is selected from CMV, RSV LTR, MPSV LTR, and SV40 promoters.

24. The method of claim 22, wherein said promoter is skin cell specific.

* * * * *

UNITED STATES PATENT AND TRADEMARK OFFICE
CERTIFICATE OF CORRECTION

PATENT NO. : 6,972,013 B1
APPLICATION NO. : 10/233007
DATED : December 6, 2005
INVENTOR(S) : Lei Zhang Page 1 of 1

It is certified that error appears in the above-identified patent and that said Letters Patent is hereby corrected as shown below:

Column 46, line 8, Claim 2, after the formula 10 mC/cm insert --$^2$--. Claim should read as follows:

2. The method of claim 1, wherein the total charge transfer at the skin tissue site is about 10 mC/cm$^2$ to about 20 mC/cm$^2$.

Signed and Sealed this

Eighth Day of January, 2008

JON W. DUDAS
*Director of the United States Patent and Trademark Office*